United States Patent
Halley et al.

(10) Patent No.: US 7,566,736 B2
(45) Date of Patent: Jul. 28, 2009

(54) SUBSTITUTED INDOLES, COMPOSITIONS CONTAINING THEM, METHOD FOR THE PRODUCTION THEREOF AND THEIR USE

(75) Inventors: Frank Halley, Chaville (FR); Catherine Souaille, Choisy le Roi (FR); Michel Tabart, La Norville (FR); Eric Bacque, Gif sur Yvette (FR); Fabrice Viviani, Louvres (FR); Baptiste Ronan, Clamart (FR); Jean-Philippe Letallec, Paris (FR); Bruno Filoche-Rommé, Creteil (FR)

(73) Assignee: Aventis Pharma S.A., Antony (FR)

( * ) Notice: Subject to any disclaimer, the term of this patent is extended or adjusted under 35 U.S.C. 154(b) by 106 days.

(21) Appl. No.: 11/757,613

(22) Filed: Jun. 4, 2007

(65) Prior Publication Data

US 2007/0259910 A1 Nov. 8, 2007

Related U.S. Application Data

(63) Continuation of application No. PCT/FR2005/003003, filed on Dec. 2, 2005.

(60) Provisional application No. 60/650,465, filed on Feb. 7, 2005.

(30) Foreign Application Priority Data

Dec. 6, 2004 (FR) .................. 04 12966

(51) Int. Cl.
*A61K 31/4045* (2006.01)
*C07D 209/04* (2006.01)
(52) U.S. Cl. .................. 514/419; 548/469; 548/492; 514/415
(58) Field of Classification Search .......... 548/469, 548/492; 514/415, 419
See application file for complete search history.

(56) References Cited

U.S. PATENT DOCUMENTS

2004/0142947 A1   7/2004  Cox et al.
2005/0026989 A1   2/2005  Kleemann

FOREIGN PATENT DOCUMENTS

| JP | 2004-149429 | 5/2004 |
| WO | WO 96/40115 | 12/1996 |
| WO | WO 99/40091 | 8/1999 |
| WO | WO 01/21589 A2 | 3/2001 |
| WO | WO 03/000695 A1 | 1/2003 |
| WO | WO 03/035621 A1 | 5/2003 |
| WO | WO 04/000831 A1 | 12/2003 |
| WO | WO 2004/007480 | 1/2004 |
| WO | WO 2005/007085 A2 | 1/2005 |
| WO | WO 2006/075152 A1 | 7/2006 |
| WO | WO 2007/010964 A1 | 1/2007 |

OTHER PUBLICATIONS

Brehm, Derivatives of Indole-2-carboxylic Acid, JACS, vol. 71, 1949, 3541-3542.
Britten et al, Beilstein Database Abstract, Chem. Ind.; 1973; 278.
Freter, Synthesis and Reactions of 3-Indolyl Beta Ketones, J.Org. Chem., vol. 37, No. 12, 1972, 2010-2015.
Frydman et al, Synthesis of Substituted 4- and 6-Azaindoles, J.Org. Chem., vol. 33, No. 10, 1968, 3762-3766.
Maddirala et al, Fischer Indolisation of 2,6-dialkyl and 2,4,6-trialkylphenylhydrazones of Diketones and Ketoesters, Tetrahedron Letters 44, 2003, 5665-5668.
Monnet et al, Synthesis of Chiral NADH Model Compounds in the Pyrrolo[3,2-b]pyridine series: Models with a Chiral Group on the Pyrrole Nitrogen or on the Carboxamide Side Chain, Tetrahedron, vol. 49, No. 26, 1993, 5831-5844.
Murakami et al, A Novel Method for the Debenzylation of Protected Indole Nitrogen, Synthesis, 1984, 738-740.
Rodrigues-Salvador et al, Beilstein Database Abstract, Synthesis Communication; 27; 8; 1997; 1439-1448.
Watanabe et al, Preparation of indoles as inhibitors against aspartate protease, .beta.-secretase, and amyloid .beta. protein for treatment of nerve disorders and myopathy, Chem. Abstracts No. 2004:429913 and JP 2004-149429.
Wislicenus et al, Beilstein Database Abstract, Justus Liebigs Ann. Chem; 436; 1924; 60.
Yakhontov et al, Beilstein Database Abstract, Russian Patent SU253068; 1970.

*Primary Examiner*—Golam M Shameem
(74) *Attorney, Agent, or Firm*—Kelly L. Bender

(57) ABSTRACT

Compounds of formula (I):

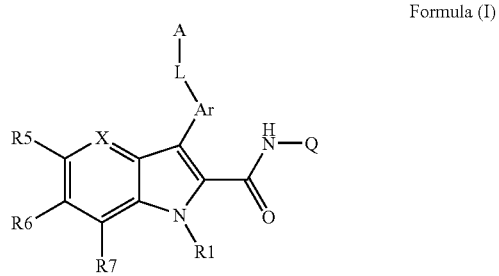

Formula (I)

wherein R1, R5, R6, R7, Ar, L, A, and Q are as defined in the description, and to salts thereof, to compositions containing them, to the process for preparing them, and to their use as medicinal products, in particular as anticancer agents.

20 Claims, No Drawings

SUBSTITUTED INDOLES, COMPOSITIONS CONTAINING THEM, METHOD FOR THE PRODUCTION THEREOF AND THEIR USE

The present invention relates in particular to novel chemical compounds, particularly to novel substituted indoles, to the compositions containing them, and to their use as medicinal products.

More particularly, the invention relates to novel specific indoles and 4-azaindoles exhibiting anticancer activity via modulation of the activity of certain kinases.

To date, most of the commercial compounds used in chemotherapy pose considerable problems of side effects and of tolerance for the patients. These effects could be limited if the medicinal products used acted selectively on the cancer cells, with the exclusion of the normal cells. One of the solutions for limiting the adverse effects of a chemotherapy could therefore consist of the use of medicinal products that act on metabolic pathways or elements constituting these pathways, expressed mainly in cancer cells, and which would be expressed very little or not at all in normal cells.

Protein kinases are a family of enzymes which catalyze the phosphorylation of hydroxyl groups of specific residues of proteins, such as tyrosine, serine or threonine residues. Such phosphorylations can greatly modify the function of the proteins; thus, protein kinases play an important role in the regulation of a large variety of cell processes, including in particular metabolism, cell proliferation, cell differentiation, cell migration or cell survival. Among the various cell functions in which the activity of a protein kinase is involved, some represent attractive targets for treating cancer-related diseases and also other diseases.

Thus, one of the objects of the present invention is to provide compositions that have anticancer activity by acting in particular with respect to certain kinases. Among the kinases for which a modulation of activity is sought, KDR and Tie2 are preferred.

The products which are the subject of the present invention correspond to formula (I) below:

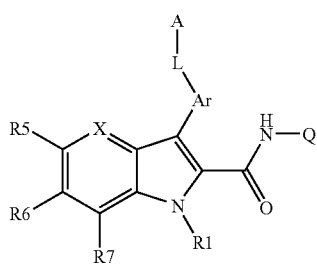

Formula (I)

in which:
a) A and Ar are independently selected from the group consisting of: aryl, heteroaryl, substituted aryl, substituted heteroaryl;
b) R1 is H or alkyl, optionally substituted;
c) X is N or N oxide or CR12;
d) L is selected from the group consisting of: bond, CO, NH, CO—NH, NH—CO, NH—SO, SO—NH, NH—SO$_2$, SO$_2$—NH, NH—CH$_2$, CH$_2$—NH, CH$_2$—CO—NH, NH—CO—CH$_2$, NH—CH$_2$—CO, CO—CH$_2$—NH, NH—CO—NH, NH—CS—NH, NH—CO—O, O—CO—NH;
e) R5, R6, R7 and R12 are each independently selected from the group consisting of: H, halogen, CF$_3$, NO$_2$, R2, CN, O(R2), OC(O)(R2), OC(O)N(R2)(R3), OS(O$_2$)(R2), N(R2)(R3), N=C(R2)(R3), N(R2)C(O)(R3), N(R2)C(O)O(R3), N(R4)C(O)N(R2)(R3), N(R2)C(O)R3N(R4)$_2$, NHC(O)R2N(R3)(R4), N(R4)C(S)N(R2)(R3), N(R2)C(S)R3N(R4)$_2$, NHC(S)R2N(R3)(R4), N(R2)S(O$_2$)(R3), OS(O$_2$)(R3), C(O) (R2), C(O)O(R2), C(O)N(R2)(R3), C(=N(R3))(R2), C(=N(OR3))(R2), S(R2), S(O)(R2), S(O$_2$)(R2), S(O$_2$)O(R2), S(O$_2$)N(R2)(R3); in which each R2, R3, R4 is independently selected from the group consisting of H, alkyl, alkylene, alkynyl, aryl, alkylaryl, heteroaryl, alkylheteroaryl, cycloalkyl, alkylcycloalkyl, heterocyclyl, alkylheterocyclyl, substituted alkyl, substituted alkylene, substituted alkynyl, substituted aryl, substituted heteroaryl, substituted cycloalkyl, substituted heterocyclyl; in which, when R2 and R3 are simultaneously present on one of R5, R6, R7 and R12, they can be linked to one another so as to form a ring comprising from 0 to 3 hetero atoms chosen from O, N and S;
f) Q is chosen from H, CH$_3$ and cyclopropyl.

Preferred products of formula (I) correspond to the definition below:

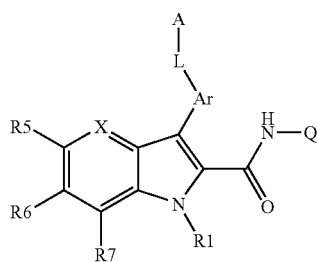

Formula (I)

in which:
a) A and R are as defined above;
b) R1 is as defined above;
c) X is N or CR12;
d) L is as defined above;
e) R5, R6, R7 and R12 are each independently selected from the group consisting of: H, halogen, CF$_3$, NO$_2$, R2, CN, O(R2), OC(O)(R2), OC(O)N(R2)(R3), OS(O$_2$)(R2), N(R2)(R3), N=C(R2)(R3), N(R2)C(O)(R3), N(R2)C(O)O(R3), N(R4)C(O)N(R2)(R3), N(R4)C(S)N(R2)(R3), N(R2)S(O$_2$)(R3), OS(O$_2$)(R3), C(O)(R2), C(O)O(R2), C(O)N(R2)(R3), C(=N(R3))(R2), C(=N(OR3))(R2), S(R2), S(O)(R2), S(O$_2$)(R2), S(O$_2$)O(R2), S(O$_2$)N(R2)(R3); in which each R2, R3, R4 is as defined above;
f) Q is as defined above.

Products of formula (I) that are more preferred correspond to the definition below:

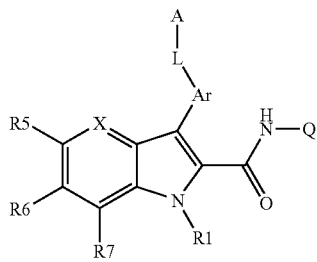

Formula (I)

in which
a) A and Ar are independently selected from the group consisting of: aryl, heteroaryl, substituted aryl, substituted heteroaryl;
b) R1 is H;
c) X is CH or N;
d) L is chosen from NH—SO$_2$ and NH—CO—NH;
e) R5, R6, R7 and R12 are each independently selected from the group consisting of: H, halogen, CF$_3$, NO$_2$, R2, CN, O(R2), OC(O)(R2), OC(O)N(R2)(R3), OS(O$_2$)(R2), N(R2)(R3), N=C(R2)(R3), N(R2)C(O)(R3), N(R2)C(O)O(R3), N(R4)C(O)N(R2)(R3), N(R4)C(S)N(R2)(R3), N(R2)S(O$_2$)(R3), OS(O$_2$)(R3), C(O)(R2), C(O)O(R2), C(O)N(R2)(R3), C(=N(R3))(R2), C(=N(OR3))(R2), S(R2), S(O)(R2), S(O$_2$)(R2), S(O$_2$)O(R2), S(O$_2$)N(R2)(R3); in which each R2, R3, R4 is independently selected from the group consisting of H, alkyl, alkylene, alkynyl, aryl, alkylaryl, heteroaryl, alkylheteroaryl, cycloalkyl, alkylcycloalkyl, heterocyclyl, alkylheterocyclyl, substituted alkyl, substituted alkylene, substituted alkynyl, substituted aryl, substituted heteroaryl, substituted cycloalkyl, substituted heterocyclyl; in which, when R2 and R3 are simultaneously present on one of R5, R6, R7 and R12, they can be linked to one another so as to form a ring which can optionally contain one or more hetero atoms chosen from O, N and S;
f) Q is H.

The products according to the invention have a substituent Q, which is preferably H.

In the products of formula (I), Ar-L-A is advantageously:

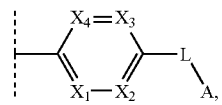

in which each X1, X2, X3 and X4 is independently chosen from N and C—R11, in which R11 is selected from the group consisting of H, halogen, NO$_2$, R2, CN, O(R2), OC(O)(R2), OC(O)N(R2)(R3), OS(O$_2$)(R2), N(R2)(R3), N=C(R2)(R3), N(R2)C(O)(R3), N(R2)C(O)O(R3), N(R4)C(O)N(R2)(R3), N(R4)C(S)N(R2)(R3), N(R2)S(O$_2$)(R3), C(O)(R2), C(O)O(R2), C(O)N(R2)(R3), C(=N(R3))(R2), C(=N(OR3))(R2), S(R2), S(O)(R2), S(O$_2$)(R2), S(O$_2$)O(R2), S(O$_2$)N(R2)(R3).

Preferred substituents R11 are selected from the group consisting of H, F, Cl, methyl, NH$_2$, OCF$_3$ and CONH$_2$.

Preferred substituents R5, R6, R7 and R8 are each independently selected from the group consisting of H, halogen, methyl, OCH$_3$, OCF$_3$, OH, NH$_2$, NH(CH$_2$)$_2$OH, NH(CH$_2$)$_2$OCH$_3$, O(CH$_2$)COOH, O(CH$_2$)$_2$COOH, O(CH$_2$)$_2$NH(CH$_2$)$_2$OCH$_3$, O(CH$_2$)$_2$NH(CH$_2$)$_2$OH, pyridin-3-ylcarbonylamino-, 2-(N,N-di-ethylamino)ethoxy, 3-(N,N-diethylamino)propoxy, 2-(pyrrolidin-1-yl)ethoxy, 3-(pyrrolidin-1-yl)propoxy, 2-(piperidin-1-yl)ethoxy, 3-(piperidin-1-yl)propoxy, 2-(4-methylpiperazin-1-yl)ethoxy, 3-(4-methylpiperazin-1-yl)propoxy, 2-(morpholin-4-yl)ethoxy and 3-(morpholin-4-yl)propoxy.

R5 and R7 are advantageously selected from H and F.
R6 is preferably H.
Preferred substituents L-A are chosen from NH—CO—NH-A, NH—SO$_2$-A and NH—CO—CH$_2$-A. A particularly effective combination is obtained when L-A is NHCONH-A.

Products in accordance with the invention preferably have a substituent A which is selected from the group consisting of phenyl, pyridyl, pyrimidyl, pyridazinyl, pyrazinyl, thienyl, furyl, pyrrolyl, oxazolyl, thiazolyl, isoxazolyl, isothiazolyl, pyrazolyl, imidazolyl, indolyl, indazolyl, benzimidazolyl, benzoxazolyl and benzothiazolyl, optionally substituted.

More preferably, A is chosen from phenyl, pyrazolyl and isoxazolyl, optionally substituted.

The substituent A is very advantageously substituted with a first substituent selected from the group consisting of alkyl, halogenated alkyl, alkylene, alkynyl, aryl, O-alkyl, O-cycloalkyl, O-aryl, O-heteroaryl, S-alkyl, S-cycloalkyl, S-aryl and S-heteroaryl, each being optionally substituted with a substituent chosen from (C$_1$-C$_3$)alkyl, halogen and O—(C$_1$-C$_3$)alkyl. The substituent A is preferably substituted with a second substituent selected from the group consisting of F, Cl, Br, I, OH, SO$_3$M, COOM, CN, NO$_2$, CON(R8)(R9), N(R8)CO(R9), (C$_1$-C$_3$)alkyl-OH, (C$_1$-C$_3$)alkyl-N(R8)(R9), (C$_1$-C$_3$)alkyl-(R10), (C$_1$-C$_3$)alkyl-COOH, N(R8)(R9) and O—(C$_2$-C$_4$)alkyl-NR8R9; in which R8 and R9 are independently chosen from H, (C$_1$-C$_3$)alkyl, (C$_1$-C$_3$)alkyl-OH, (C$_1$-C$_3$)alkyl-NH$_2$, (C$_1$-C$_3$)alkyl-COOM and (C$_1$-C$_3$)alkyl-SO$_3$M; in which, when R8 and R9 are simultaneously different from H, they can be linked so as to form a ring which contains from 0 to 3 hetero atoms chosen from N, S and O; in which M is H or an alkali metal cation chosen from Li, Na and K; and in which R10 is H or an optionally substituted nonaromatic heterocycle comprising 2 to 7 carbon atoms and 1 to 3 hetero atoms chosen from N, O and S.

Particularly preferred substituents A are chosen from phenyl, pyrazolyl and isoxazolyl, said substituents A being preferably substituted with halogen (in particular F), (C$_1$-C$_4$)alkyl, halogenated (C$_1$-C$_3$)alkyl (in particular CF$_3$), O—(C$_1$-C$_4$)alkyl, O-cycloalkyl, S—(C$_1$-C$_4$)alkyl, S-cycloalkyl, halogenated O—(C$_1$-C$_4$)alkyl, and halogenated S—(C$_1$-C$_4$) alkyl.

A preferred substituent A is a phenyl substituted with 0, 1, 2, 3, 4 or 5 substituents selected from the group consisting of alkyl, halogenated alkyl, alkylene, alkynyl, aryl, O-alkyl, O-cycloalkyl, O-aryl, O-heteroaryl, S-alkyl, S-cycloalykl, S-aryl, S-heteroaryl; each being optionally substituted with a substituent chosen from (C$_1$-C$_3$)alkyl, halogen, O—(C$_1$-C$_3$)alkyl; and F, Cl, Br, I, OH, SO$_3$M, COOM, CN, NO$_2$, CON(R8)(R9), N(R8)CO(R9), (C$_1$-C$_3$)alkyl-OH, (C$_1$-C$_3$)alkyl-N(R8)(R9), (C$_1$-C$_3$)alkyl-(R10), (C$_1$-C$_3$)alkyl-COOH, N(R8)(R9), O—(C$_2$-C$_4$)alkyl-N(R8)(R9); in which R8 and R9 are independently chosen from H, (C$_1$-C$_3$)alkyl, (C$_1$-C$_3$)alkyl-OH, (C$_1$-C$_3$)alkyl-NH$_2$, (C$_1$-C$_3$)alkyl-COOM, (C$_1$-C$_3$)alkyl-SO$_3$M; in which, when R8 and R9 are simultaneously different from H, they can be linked so as to form a ring comprising from 0 to 3 hetero atoms chosen from O, N and S; in which M is H or an alkali metal cation chosen from Li, Na and K; and in which R10 is H or an optionally substituted nonaromatic heterocycle comprising 2 to 7 carbon atoms and 1 to 3 hetero atoms chosen from N, O and S.

The products of examples 1 to 104 are advantageously the subject of the present invention.

A product in accordance with the invention may be in any one of the following forms:
1) nonchiral, or
2) racemic, or
3) enriched in a stereoisomer, or
4) enriched in an enantiomer;

and may be optionally salified.

A product in accordance with the invention may be used for producing a medicinal product that is useful for treating a pathological state, in particular a cancer, or a disease related to a deregulation of angiogenesis such as psoriasis, chronic inflammation, age-related macular degeneration, rheumatoid arthritis, diabetic retinopathy, Kaposi's sarcoma or infantile hemangioma.

The present invention also relates to the therapeutic compositions comprising a product according to the invention, in combination with a pharmaceutically acceptable excipient according to the chosen mode of administration. The pharmaceutical composition may be in solid or liquid form or in the form of liposomes.

Among the solid compositions, mention may be made of powders, gelatin capsules and tablets. Solid forms that are protected with respect to the acid medium of the stomach may also be included among the oral forms. The carriers used for the solid forms consist in particular of mineral carriers such as phosphates or carbonates, or of organic carriers such as lactose, celluloses, starch or polymers. The liquid forms consist of solutions, of suspensions or of dispersions. They contain, as dispersive carrier, either water or an organic solvent (ethanol, NMP or the like) or mixtures of surfactants and of solvents or of complexing agents and of solvents.

The liquid forms will preferably be injectable and, as a result, will have a formulation that is acceptable for such a use.

Acceptable routes of administration by injection include intravenous, intraperitoneal, intramuscular and subcutaneous routes, the intravenous route usually being preferred.

The administered dose of the compounds of the invention will be adjusted by the practitioner according to the route of administration to the patient and to the condition of the latter.

The compounds of the present invention may be administered alone or as a mixture with other anticancer agents. Among the possible combinations, mention may be made of:

alkylating agents, and in particular cyclophosphamide, melphalan, ifosfamide, chlorambucil, busulfan, thiotepa, prednimustine, carmustine, lomustine, semustine, streptozotocin, decarbazine, temozolomide, procarbazine and hexamethylmelamine;

platinum derivatives, such as in particular cisplatin, carboplatin or oxaliplatin;

antibiotics, such as in particular bleomycin, mitomycin or dactinomycin;

antimicrotubule agents, such as in particular vinblastine, vincristine, vindesine, vinorelbine or the taxoids (paclitaxel and docetaxel);

anthracyclines, such as in particular doxorubicin, daunorubicin, idarubicin, epirubicin, mitoxantrone or losoxantrone;

inhibitors of group I and II topoisomerases, such as etoposide, teniposide, amsacrine, irinotecan, topotecan and tomudex;

fluoropyrimidines such as 5-fluorouracil, UFT or floxuridine;

cytidine analogs such as 5-azacytidine, cytarabine, gemcitabine, 6-mercaptomurine or 6-thioguanine;

adenosine analogs such as pentostatin, cytarabine or fludarabine phosphate;

methotrexate and folinic acid;

various enzymes and compounds such as L-asparaginase, hydroxyurea, trans-retinoic acid, suramin, dexrazoxane, amifostine, herceptin and also estrogenic and androgenic hormones;

antivascular agents such as derivatives of combretastatin or of colchicine, and prodrugs thereof.

It is also possible to combine radiation treatment with the compounds of the present invention. These treatments can be administered simultaneously, separately or sequentially. The treatment will be adjusted by the practitioner according to the disease to be treated.

The products of the invention are useful as agents for inhibiting certain kinases. KDR, Tie2, Auroral, Aurora2, FAK, PDGFR, FLT1, FGFR and VEGF-R3 are kinases for which the products of the invention will be particularly useful as inhibitors. Among these kinases, KDR and Tie2 are preferred. Among the products of the invention, the products of general formula (I) in which X is a nitrogen atom are preferred as inhibitors of KDR, Tie2 and FAK.

The reasons for which the latter kinases are chosen are given below:

KDR

KDR (Kinase insert Domain Receptor), also called VEGF-R2 (Vascular Endothelial Growth Factor Receptor 2), is expressed essentially in endothelial cells. This receptor binds the angiogenic growth factor VEGF, and thus serves as a transduction signal mediator by the activation of its intracellular kinase domain. Direct inhibition of the kinase activity of VEGF-R2 makes it possible to decrease the phenomenon of angiogenesis in the presence of exogenous VEGF (Vascular Endothelial Growth Factor) (Strawn et al., *Cancer Research*, 1996, vol. 56, p. 3540-3545). This process was demonstrated in particular using VEGF-R2 mutants (Millauer et al., *Cancer Research*, 1996, vol. 56, p. 1615-1620). The VEGF-R2 receptor appears to have no function in adults other than that related to the angiogenic activity of VEGF. Consequently, a selective inhibitor of the kinase activity of VEGF-R2 should show only slight toxicity.

In addition to this central role in the dynamic angiogenic process, recent results suggest that the expression of VEGF contributes to the survival of tumor cells after chemotherapy and radiotherapy, underlining the potential synergy of KDR inhibitors with other agents (Lee et al., *Cancer Research*, 2000, vol. 60, p. 5565-5570).

Tie2

Tie-2 (TEK) is a member of a tyrosine kinase receptor family, that is expressed essentially in endothelial cells. Tie2 is the first receptor with tyrosine kinase activity for which both the agonist (angiopoietin 1 or Ang1) which stimulates autophosphorylation of the receptor and the cell signaling [S. Davis et al. (1996) *Cell* 87, 1161-1169] and the antagonist (angiopoietin 2 or Ang2) [P. C. Maisonpierre et al. (1997) *Science* 227, 55-60] are known. Angiopoietin 1 can synergize with VEGF in the final stages of neoangiogenesis [Asahara T. *Circ. Res.* (1998) 233-240]. Knock-out experiments and transgenic manipulations of Tie2 expression or Ang1 expression result in animals which exhibit vascularization deficiencies [D. J. Dumont et al. (1994) *Genes Dev.* 8, 1897-1909 and C. Suri (1996) *Cell* 87, 1171-1180]. The binding of Ang1 to its receptor results in autophosphorylation of the kinase domain of Tie2, which is essential for neovascularization and also for the recruitment and interaction of the vessels with pericytes and smooth muscle cells; these phenomena contribute to the maturation and the stability of the newly formed vessels [P. C. Maisonpierre et al. (1997) *Science* 227, 55-60]. Lin et al. (1997) *J. Clin. Invest.* 100, 8: 2072-2078 and Lin P. (1998) *PNAS* 95, 8829-8834, have shown an inhibition of tumor growth and vascularization and also a decrease in lung metastases in adenoviral infections or injections of the extracellular domain of Tie-2 (Tek) in breast tumor and melanoma xenograph models.

Tie2 inhibitors can be used in situations where neovascularization occurs inappropriately (i.e. in diabetic retinopathy, chronic inflammation, psoriasis, Kaposi's sarcoma, chronic neovascularization due to macular degeneration, rheumatoid arthritis, infantile hemangioma and cancers).

FAK

FAK (Focal Adhesion Kinase) is a cytoplasmic tyrosine kinase that plays an important role in the signal transduction transmitted by integrins, a family of heterodimeric cell adhesion receptors. FAK and the integrins are colocalized in perimembrane structures called adhesion plaques. It has been shown, in many cell types, that the activation of FAK and phosphorylation thereof on tyrosine residues, and in particular autophosphorylation thereof on tyrosine 397, is dependent on the binding of integrins to their extracellular ligands and therefore induced during cell adhesion [Kornberg L, et al. J. Biol. Chem. 267(33): 23439-442. (1992)]. The autophosphorylation on tyrosine 397 of FAK represents a binding site for another tyrosine kinase, Src, via its SH2 domain (Schaller et al. Mol. Cell. Biol. 14: 1680-1688, 1994; Xing et al. Mol. Cell. Biol. 5: 413-421, 1994]. Src can then phosphorylate FAK on tyrosine 925, thus recruiting the Grb2 adaptor protein and inducing, in certain cells, activation of the ras and MAP kinase pathway involved in the control of cell proliferation [Schlaepfer et al. Nature; 372: 786-791, 1994; Schlaepfer et al. Prog. Biophy. Mol. Biol. 71: 435-478, 1999; Schlaepfer and Hunter, J. Biol. Chem. 272: 13189-13195, 1997]. The activation of FAK can also induce the jun $NH_2$-terminal kinase (JNK) signaling pathway and result in the progression of cells to phase G1 of the cell cycle [Otkay et al. J. Cell. Biol. 145: 1461-1469, 1999]. Phosphatidylinositol-3-OH kinase (PI3-kinase) also binds to FAK on tyrosine 397, and this interaction could be necessary for the activation of PI3-kinase [Chen and Guan, Proc. Nat. Acad. Sci. USA 91: 10148-10152, 1994; Ling et al. J. Cell, Biochem. 73: 533-544, 1999]. The FAK/Src complex phosphorylates various substrates such as paxillin and p130CAS in fibroblasts [Vuori et al. Mol. Cell. Biol. 16: 2606-2613, 1996].

The results of many studies support the hypothesis that FAK inhibitors could be useful in the treatment of cancer. Studies have suggested that FAK may play an important role in cell proliferation and/or survival in vitro. For example, in CHO cells, certain authors have demonstrated that overexpression of p125FAK results in an acceleration of G1 to S transition, suggesting that p125FAK promotes cell proliferation [Zhao J.-H et al. J. Cell. Biol. 143: 1997-2008, 1998]. Other authors have shown that tumor cells treated with FAK antisense oligonucleotides lose their adhesion and enter into apoptosis (Xu et al. Cell Growth Differ. 4: 413-418, 1996). It has also been demonstrated that FAK promotes cell migration in vitro. Thus, fibroblasts deficient for FAK expression (FAK "knockout" mice) exhibit a rounded morphology, and deficiencies in cell migration in response to chemotactic signals, and these defects are eliminated by reexpression of FAK [D J. Sieg et al., J. Cell, Science. 112: 2677-91, 1999]. Overexpression of the C-terminal domain of FAK (FRNK) blocks the elongation of adherent cells and reduces cell migration in vitro [Richardson A. and Parsons J. T. Nature. 380: 538-540, 1996]. Overexpression of FAK in CHO or COS cells or in human astrocytoma cells promotes migration of the cells. Involvement of FAK in the promotion of cell proliferation and migration in many cell types, in vitro, suggests that FAK has a potential role in neoplastic processes. A recent study has effectively demonstrated an increase in the proliferation of tumor cells in vivo after induction of FAK expression in human astrocytoma cells [Cary L. A. et al. J. Cell Sci. 109: 1787-94, 1996; Wang D et al. J. Cell Sci. 113: 4221-4230, 2000]. In addition, immunohistochemical studies of human biopsies have demonstrated that FAK is overexpressed in prostate cancers, breast cancers, thyroid cancers, colon cancers, melanoma cancers, brain cancers and lung cancers, the level of FAK expression being directly correlated with tumors exhibiting the most aggressive phenotype [Weiner T M, et al. Lancet. 342 (8878): 1024-1025, 1993; Owens et al. Cancer Research. 55: 2752-2755, 1995; Maung K. et al. Oncogene. 18: 6824-6828, 1999; Wang D et al. J. Cell Sci. 113: 4221-4230, 2000].

Definitions

The term "halogen" refers to an element chosen from F, Cl, Br and I.

The term "alkyl" refers to a linear or branched, saturated hydrocarbon-based substituent having from 1 to 12 carbon atoms. The methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 1-ethylbutyl, 2-ethylbutyl, 3,3-dimethylbutyl, heptyl, 1-ethylpentyl, octyl, nonyl, decyl, undecyl and dodecyl substituents are examples of an alkyl substituent.

The term "alkylene" refers to a linear or branched hydrocarbon-based substituent having one or more unsaturations and having from 2 to 12 carbon atoms. The ethylenyl, 1-methylethylenyl, prop-1-enyl, prop-2-enyl, Z-1-methylprop-1-enyl, E-1-methylprop-1-enyl, Z-1,2-dimethylprop-1-enyl, E-1,2-dimethylprop-1-enyl, but-1,3-dienyl, 1-methylidenylprop-2-enyl, Z-2-methyl-but-1,3-dienyl, E-2-methylbut-1,3-dienyl, 2-methyl-1-methylidenylprop-2-enyl, undec-1-enyl and undec-10-enyl substituents are examples of an alkylene substituent.

The term "alkynyl" refers to a linear or branched hydrocarbon-based substituent having at least two unsaturations carried by a pair of vicinal carbon atoms, and having from 2 to 12 carbon atoms. The ethynyl, prop-1-ynyl, prop-2-ynyl and but-1-ynyl substituents are examples of an alkynyl substituent.

The term "aryl" refers to a mono- or polycyclic aromatic substituent having from 6 to 14 carbon atoms. The phenyl, naphth-1-yl, naphth-2-yl, anthracen-9-yl, 1,2,3,4-tetrahydronaphth-5-yl and 1,2,3,4-tetrahydronaphth-6-yl substituents are examples of an aryl substituent.

The term "heteroaryl" refers to a mono- or polycyclic heteroaromatic substituent having from 1 to 13 carbon atoms and from 1 to 4 hetero atoms. The pyrrol-1-yl, pyrrol-2-yl, pyrrol-3-yl, furyl, thienyl, imidazolyl, oxazolyl, thiazolyl, isoxazolyl, isothiazolyl, 1,2,4-triazolyl, oxadiazolyl, thiadiazolyl, tetrazolyl, pyridyl, pyrimidyl, pyrazinyl, 1,3,5-triazinyl, indolyl, benzo[b]furyl, benzo[b]thienyl, indazolyl, benzimidazolyl, azaindolyl, quinolyl, isoquinolyl, carbazolyl and acridyl substituents are examples of a heteroaryl substituent.

The term "hetero atom" refers here to an at least divalent atom other than carbon. N, O, S and Se are examples of a hetero atom.

The term "cycloalkyl" refers to a saturated or partially unsaturated, cyclic hydrocarbon-based substituent having from 3 to 12 carbon atoms. The cyclopropyl, cyclobutyl, cyclopentyl, cyclopentenyl, cyclopentadienyl, cyclohexyl, cyclohexenyl, cycloheptyl, bicyclo[2.2.1]heptyl, cyclooctyl, bicyclo-[2.2.2]octyl, adamantyl and perhydronaphthyl substituents are examples of a cycloalkyl substituent.

The term "heterocyclyl" refers to a saturated or partially unsaturated, cyclic hydrocarbon-based substituent having from 1 to 13 carbon atoms and from 1 to 4 hetero atoms. Preferably, the saturated or partially unsaturated, cyclic hydrocarbon-based substituent will be monocyclic and will comprise 4 or 5 carbon atoms and 1 to 3 hetero atoms.

The term "substituted" refers to a substituent other than H, for example halogen, alkyl, aryl, heteroaryl, cycloalkyl, heterocyclyl, alkylene, alkynyl, OH, O-alkyl, O-alkylene, O-aryl, O-heteroaryl, $NH_2$, NH-alkyl, NH-aryl, NH-heteroaryl, SH, S-alkyl, S-aryl, $S(O_2)$ H, $S(O_2)$-alkyl, $S(O_2)$-aryl, $SO_3H$, $SO_3$-alkyl, $SO_3$-aryl, CHO, C(O)-alkyl, C(O)-aryl, C(O)OH, C(O)O-alkyl, C(O)O-aryl, OC(O)-alkyl, OC(O)-aryl, $C(O)NH_2$, C(O)NH-alkyl, C(O)NH-aryl, NHCHO, NHC(O)-alkyl, NHC(O)-aryl, NH-cycloalkyl or NH-heterocyclyl.

The products according to the invention can be prepared using conventional methods of organic chemistry. Schemes 1 and 2 below illustrate two methods used for the preparation of the following examples. In this respect, they cannot constitute a limitation of the scope of the invention as regards the methods for preparing the compounds claimed.

Method a:

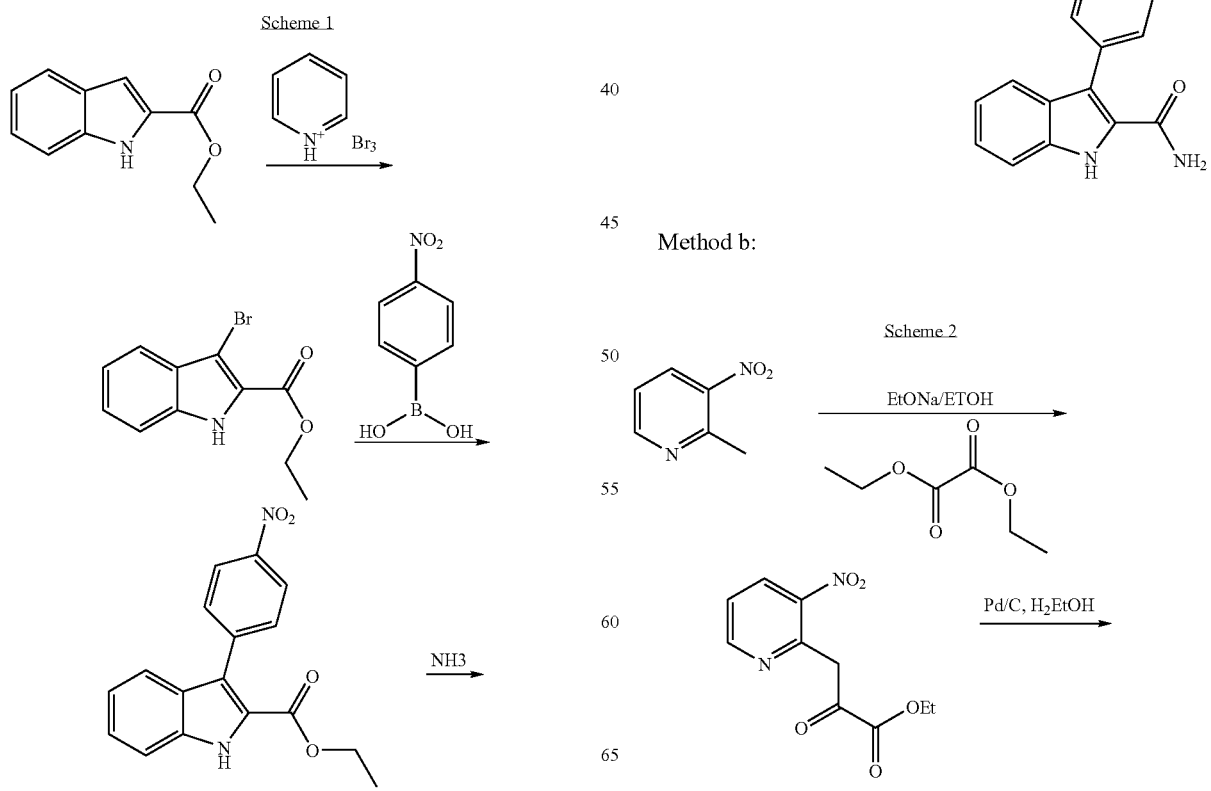

Method b:

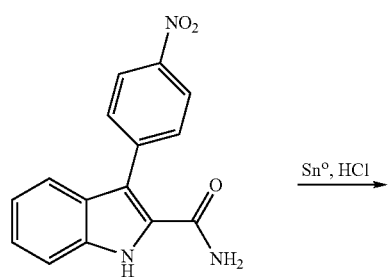

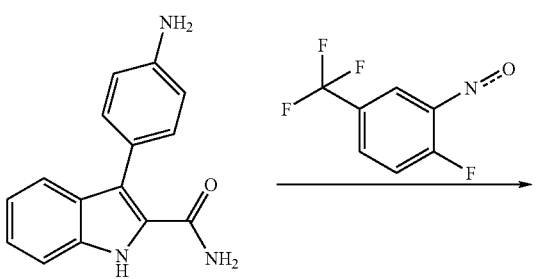

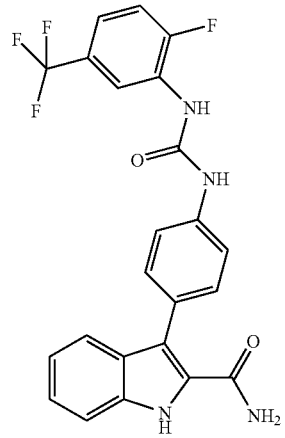

-continued

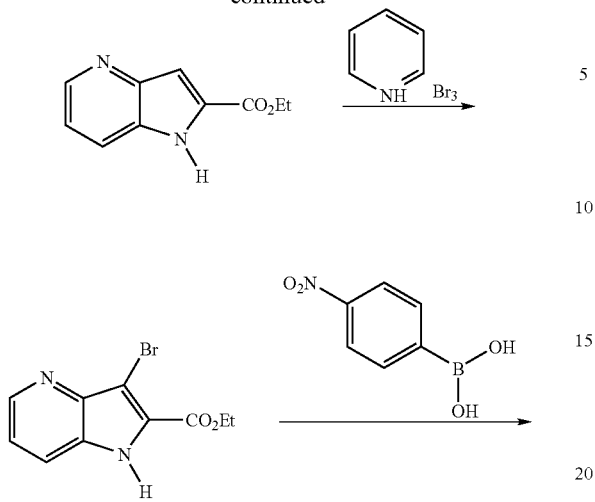

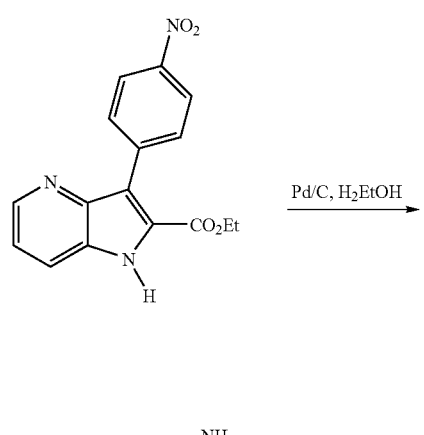

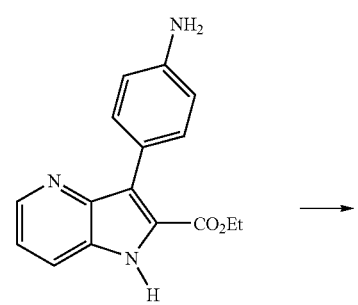

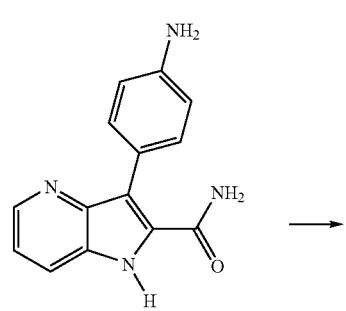

-continued

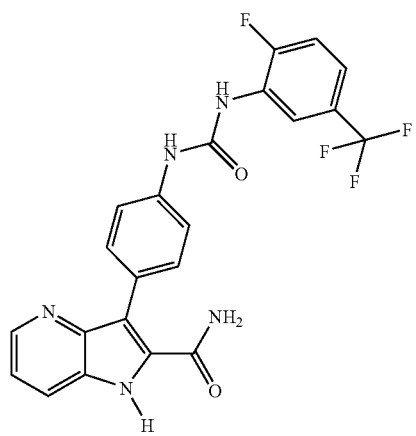

In both cases, an alternative synthetic pathway consists in condensing, with the brom(aza)indole, boronic acid carrying the urea chain.

A further subject of the present invention is a process for preparing the products of general formula (I) as defined in claim 1, characterized in that a product of general formula (VI) below:

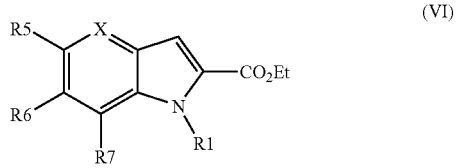

is subjected to the following steps:
  halogenation in the 3-position, then
  Suzuki coupling in the 3-position, so as to obtain a product of general formula (IV) below:

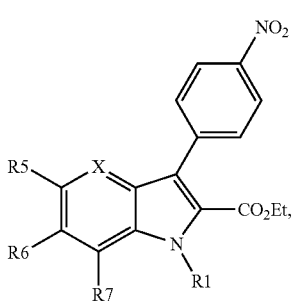

then
  reduction of the nitrophenyl group to aminophenyl in the 3-position and amidation of the ester in the 2-position, or amidation of the ester in the 2-position and reduction of the nitrophenyl group to aminophenyl in the 3-position, so as to obtain the product of general formula (II) below:

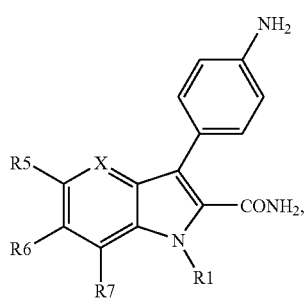

then
acylation of the aminophenyl group in the 3-position.

The intermediate products of general formulae (II), (IV) and (VI) are also subject of the present invention.

It is understood, for those skilled in the art, that, in order to carry out the processes according to the invention described above, it may be necessary to introduce groups that protect the amino, carboxyl and alcohol functions in order to avoid side reactions. These groups are those which can be eliminated without affecting the rest of the molecule. As examples of groups that protect the amino function, mention may be made of tert-butyl carbamate which can be regenerated by means of iodotrimethylsilane, and acetyl which can be regenerated in acid medium (hydrochloric acid for example). As groups that protect the carboxyl function, mention may be made of esters (methoxymethyl ester, benzyl ester for example). As groups that protect the alcohol function, mention may be made of esters (benzoyl ester for example) which can be regenerated in acid medium or by catalytic hydrogenation. Other protective groups that can be used are described by T. W. Greene et al., in Protective Groups in Organic Synthesis, third edition, 1999, Wiley-Interscience.

The compounds of formula (I) are isolated and can be purified by the usual known methods, for example by crystallization, chromatography or extraction.

The enantiomers and diastereoisomers of the compounds of formula (I) are also part of the invention.

The compounds of formula (I) comprising a basic residue may be optionally converted to addition salts with an inorganic or organic acid, by the action of such an acid in a solvent, for example an organic solvent, such as an alcohol, a ketone, an ether or a chlorinated solvent.

The compounds of formula (I) comprising an acid residue may be optionally converted to metal salts or to addition salts with nitrogenous bases according to methods known per se. These salts can be obtained by the action of a metal base (alkali metal or alkaline-earth metal base, for example), of ammonia, of an amine or of an amine salt on a compound of formula (I), in a solvent. The salt formed is separated by the usual methods.

These salts are also part of the invention.

When a product according to the invention exhibits at least one free basic function, pharmaceutically acceptable salts can be prepared by reaction between said product and an inorganic or organic acid. Pharmaceutically acceptable salts include chlorides, nitrates, sulfates, hydrogen sulfates, pyrosulfates, bisulfates, sulfites, bisulfites, phosphates, monohydrogen phosphates, dihydrogen phosphates, metaphosphates, pyrophosphates, acetates, propionates, acrylates, 4-hydroxybutyrates, caprylates, caproates, decanoates, oxalates, malonates, succinates, glutarates, adipates, pimelates, maleates, fumarates, citrates, tartrates, lactates, phenylacetates, mandelates, sebacates, suberates, benzoates phthalates, methanesulfonates, propanesulfonates, xylenesulfonates, salicylates, cinnamates, glutamates, aspartates, glucuronates or galacturonates.

When a product according to the invention exhibits at least one free acidic function, pharmaceutically acceptable salts can be prepared by reaction between said product and an inorganic or organic base. Pharmaceutically acceptable bases include hydroxides of alkali metal or alkaline-earth metal cations, such as Li, Na, K, Mg or Ca, and basic amine compounds, such as ammonia, arginine, histidine, piperidine, morpholine, piperazine or triethylamine.

The invention is also described by means of the following examples, given by way of illustration of the invention.

The LC/MS analyses are carried out on a Micromass model LCT device connected to an HP 1100 device. The abundance of the products are measured using an HP G1315A diode array detector over a wavelength range of 200-600 nm and a Sedex 65 light scattering detector. The mass spectra are acquired over a range of from 180 to 800. The data are analyzed using the Micromass MassLynx software. Separation is carried out on a Hypersil BDS C18, 3 µm (50×4.6 mm) column, by eluting with a linear gradient from 5 to 90% of acetonitrile comprising 0.05% (v/v) of trifluoroacetic acid (TFA) in water comprising 0.05% (v/v) of TFA, over 3.5 min at a flow rate of 1 ml/min. The total analysis time, including the period for re-equilibrating the column, is 7 min.

The MS spectra are determined using the electrospray technique ($ES^+$) on a Platform II device (Micromass). The main ions observed are described.

The melting points are measured using the capillary technique, on a Mettler FP62 device, range 30° C. to 300° C., rise of 2° C. per minute.

The retention times of examples 72 to 74 are carried out on columns of the XBRIDGE C18 type, 3×50 mm, 2.5 µm particles. The products are eluted with a linear gradient of 5 to 95% acetonitrile in water containing 0.1% formic acid over 7 minutes at a flow rate of 1.1 ml/min.

The retention times of examples 77 to 102 are carried out on columns of the Waters Xterra $C_{18}$ type, 3×50 mm, 3.5 µm particles. The products are eluted with a linear gradient of 5 to 90% acetonitrile in water containing 0.5% TFA over 7 minutes at a flow rate of 600 µl/min.

Purification by LC/MS:

The products can be purified by LC/MS using a Waters FractionsLynx system composed of a Waters model 600 gradient pump, a Waters model 515 regeneration pump, a Waters Reagent Manager dilution pump, a Waters model 2700 autoinjector, two Rheodyne model LabPro valves, a Waters model 996 diode array detector, a Waters model ZMD mass spectrometer and a Gilson model 204 fraction collector. The system is controlled by the Waters FractionLynx software. Separation is carried out alternately on two Waters Symmetry columns ($C_{18}$, 5 µm, 19×50 mm, catalogue reference 186000210), one column undergoing regeneration with a 95/5 (v/v) water/acetonitrile mixture comprising 0.07% (v/v) of trifluoroacetic acid, while the other column is being used for separation. The columns are eluted using a linear gradient from 5% to 95% of acetonitrile comprising 0.07% (v/v) of trifluoroacetic acid in water comprising 0.07% (v/v) of trifluoroacetic acid, at a flow rate of 10 ml/min. At the outlet of the separation column, one-thousandth of the effluent is separated by means of an LC Packing Accurate, diluted with methyl alcohol at a flow rate of 0.5 ml/min and sent to the detectors, in a proportion of 75% to the diode array detector and the remaining 25% to the mass spectrometer. The rest of the effluent (999/1 000) is sent to the fraction collector, where the flow is discarded for as long as the mass of the expected product is not detected by the FractionLynx software. The molecular formulae of the expected products are supplied to the FractionLynx software, which actuates the collection of the product when the mass signal detected corresponds to the ion [M+H]$^+$and/or to [M+Na]$^+$. In certain cases, depending on the analytical LC/MS results, when an intense ion corresponding to [M+2H]$^{++}$ has been detected, the value corresponding to half the calculated molecular mass (MW/2) is also supplied to the FractionLynx software. Under these conditions, the collection is also actuated when the mass signal for the ion [M+2H]$^{++}$ and/or [M+Na+HH]$^{++}$ is/are detected. The products are collected in a tared glass tube. After collection, the solvents are evaporated in a Savant AES 2000 or Genevac HT8 centrifugal evaporator and the masses of products are determined by weighing the tubes after evaporation of the solvents.

EXAMPLE 1

3-{4-[3-(2-Fluoro-5-trifluoromethylphenyl)-ureido]phenyl}-1H-indole-2-carboxamide

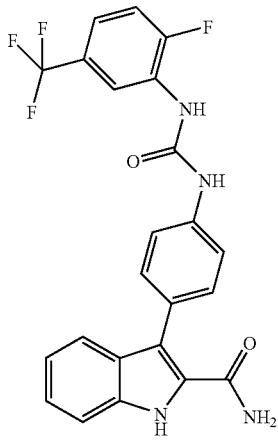

Method a:

Ethyl 3-bromo-1H-indole-2-carboxylate 67 g of pyridinium tribromide in 300 ml of pyridine are added slowly, at 0° C. under argon, to a solution of 37.8 g of ethyl indole-2-carboxylate in 900 ml of pyridine. The solution is then heated at 50° C. for 30 minutes and then poured onto 4 l of ice-cold water. The solid formed is filtered off, washed with water and filter-dried. After drying under vacuum, 48.4 g of ethyl 3-bromo-1H-indole-2-carboxylate are obtained, the characteristics of which are as follows:

MS (ES+) spectrum: m/z=269 [MH]$^+$

Melting point=148-150° C. (Köfler bench).

1H NMR spectrum (300 MHz, DMSO-d6, δ in ppm): 1.38 (t, J=7.0 Hz, 3H); 4.38 (q, J=7.0 Hz, 2H); 7.20 (broad t, J=8.0 Hz, 1H); 7.37 (broad t, J=8.0 Hz, 1H); 7.50 (broad d, J=8.0 Hz, 1H); 7.54 (broad d, J=8.0 Hz, 1H); 12.2 (broad m, 1H)

IR spectrum (KBr): 3454; 3319; 3297; 1701; 1681; 1517; 1331; 1240 and 644 cm$^{-1}$ Ethyl 3-(4-nitrophenyl)-1H-indole-2-carboxylate 46 ml of a 1M sodium carbonate solution, 2.23 g of lithium chloride and then 1.1 g of tetrakis(triphenylphosphine)palladium are added successively, under argon and with stirring, to a solution of 5 g of ethyl 3-bromo-1H-indole-2-carboxylate and 7.8 g of 4-nitrophenylboronic acid in 110 ml of ethanol and 110 ml of toluene. The solution is refluxed for 2 hours 30 minutes and then concentrated under reduced pressure. The precipitate is filtered off and then recrystallized from ethanol, to give 5.1 g of ethyl 3-(4-nitrophenyl)-1H-indole-2-carboxylate, the characteristics of which are as follows:

MS (ES+) spectrum: m/z=311 [MH]+

Melting point=218-220° C. (Köfler bench).

1H NMR spectrum (300 MHz, DMSO-d6, δ in ppm): 1.21 (t, J=7.0 Hz, 3H); 4.26 (q, J=7.0 Hz, 2H); 7.14 (broad t, J=8.0 Hz, 1H); 7.37 (broad t, J=8.5 Hz, 1H); from 7.50 to 7.60 (m, 2H); 7.81 (broad d, J=8.0 Hz, 2H); 8.30 (broad d, J=8.5 Hz, 2H); 12.2 (broad m, 1H).

IR spectrum (KBr): 3405; 1717; 1510; 1343; 1239; 859 and 757 cm$^{-1}$ 3-(4-Nitrophenyl)-1H-indole-2-carboxamide A solution of 0.5 g of ammonium chloride in 30 ml of concentrated aqueous ammonia is added to a solution of 3.3 g of ethyl 3-(4-nitrophenyl)-1H-indole-2-carboxylate in 50 ml of 7N methanolic ammonia. The solution is then heated in a sealed tube at 125° C. for 15 hours. After cooling, the solid formed is filtered off, washed with water, and then filter-dried. After drying under vacuum, 1.5 g of 3-(4-nitrophenyl)-1H-indole-2-carboxamide are obtained, the characteristics of which are as follows:

MS (ES+) spectrum: m/z=282 [MH]+

Melting point=258-260° C. (Köfler bench).

Elemental analysis: C %: 63.74; H %: 3.76; N %: 14.90 (theory: C %: 64.06; H %: 3.94; N %: 14.94)

1H NMR spectrum (300 MHz, DMSO-d6, δ in ppm): 7.13 (broad t, J=8.0 Hz, 1H); from 7.22 to 7.65 (partially masked very broad m, 2H); 7.30 (broad t, J=8.0 Hz, 1H); 7.51 (broad d, J=8.0 Hz, 1); 7.59 (broad d, J=8.0 Hz, 1H); 7.79 (broad d, J=8.5 Hz, 2H); 8.31 (broad d, J=8.5 Hz, 2H); from 11.4 to 11.8 (very broad m, 1H).

3-(4-Aminophenyl)-1H-indole-2-carboxamide 2.7 g of tin are added to a suspension of 1.3 g of 3-(4-nitrophenyl)-1H-indole-2-carboxamide in 50 ml of 5N hydrochloric acid. The mixture is stirred at ambient temperature for 5 hours and then neutralized with a 5N sodium hydroxide solution. The aqueous phase is extracted with 3 times 50 ml of ethyl acetate and the organic phase is dried over magnesium sulfate, filtered, and concentrated under reduced pressure. After purification by flash chromatography on a silica column, elution being carried out with a mixture of cyclohexane and ethyl acetate (20/80 by volume), 0.15 g of 3-(4-aminophenyl)-1H-indole-2-carboxamide are obtained, the characteristics of which are as follows:

MS (ES+) spectrum: m/z=252 [MH]+

Melting point=180-182° C. (Köfler bench).

1H NMR spectrum (300 MHz, DMSO-d6, δ in ppm): 5.24 (broad s, 2H); 6.12 (broad m, 1H); 6.70 (broad d, J=8.5 Hz, 2H); 7.01 (broad t, J=8.0 Hz, 1H); 7.13 (broad d, J=8.5 Hz, 2H); 7.20 (broad t, J=8.0 Hz, 1H); 7.33 (broad d, J=8.0 Hz, 1H); 7.43 (broad d, J=8.0 Hz, 1H); from 7.30 to 7.45 (partially masked very broad m, 1H); 11.45 (broad m, 1H).

IR spectrum (KBr): 3452; 3370; 1648; 1582; 1345 and 747 cm$^{-1}$

3-{4-[3-(2-Fluoro-5-trifluoromethylphenyl)ureido]-phenyl}-1H-indole-2-carboxamide 0.089 ml of 2-fluoro-5-trifluoromethyl isocyanate in solution in 2 ml of tetrahydrofuran is added, dropwise at 10° C., to a solution of 0.11 g of 3-(4-aminophenyl)-1H-indole-2-carboxamide in 18 ml of tetrahydrofuran. After stirring for 1 hour at 20° C., 5 ml of methanol and 2 ml of triethylamine are added and the stirring is continued for 1 hour. The reaction medium is then concentrated under reduced pressure and the residue is purified by chromatography on a silica column, elution being carried out with a mixture of cyclohexane and ethyl acetate (35/65 by volume), to give 0.13 g of 3-{4-[3-(2-fluoro-5-trifluoromethylphenyl)ureido]phenyl}-1H-indole-2-carboxamide, the characteristics of which are as follows:

MS (ES+) spectrum: m/z=457 [MH]+

Melting point=240-242° C. (Köfler bench).

1H NMR spectrum (300 MHz, DMSO-d6, δ in ppm): 6.48 (broad m, 1H); 7.06 (broad t, J=8.0 Hz, 1H); 7.23 (broad t, J=8.0 Hz, 1H); from 7.36 to 7.57 (m, 7H); 7.60 (broad d, J=8.5 Hz, 2H); 8.65 (dd, J=2.5 and 7.5 Hz, 1H); 8.97 (broad m, 1H); 9.32 (broad m, 1H); 11.6 (broad m, 1H)

IR spectrum (KBr): 3463; 3338; 1651; 1590; 1543; 1443; 1340; 1119; 1070 and 745 cm$^{-1}$

EXAMPLE 2

3-{4-[3-(2-Fluoro-5-trifluoromethylphenyl)-ureido]phenyl}-1H-pyrrolo[3,2-b]pyridine-2-carboxamide

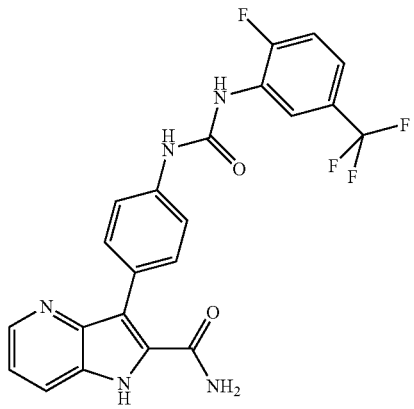

Method b:

Ethyl 3-(3-nitropyridin-2-yl)-2-oxopropionate 121.7 g of ethyl oxalate and then 15.8 g of 2-methyl-3-nitropyridine in solution in 100 ml of ethanol are added to a solution of sodium ethanolate, prepared by adding 4 g of sodium to 400 ml of ethanol stirred under argon. The reaction mixture is stirred for 15 hours and the solid formed is filtered off, washed successively with 100 ml of ethanol and 100 ml of diisopropyl ether, and then filter-dried. The solid is taken up in 300 ml of ethanol and acidified with a 5N hydrochloric acid solution. The solid obtained is filtered off, washed with 50 ml of a 5N hydrochloric acid solution and then with 100 ml of ethanol, and filter-dried. After drying under vacuum, 18.7 g of ethyl 3-(3-nitropyridine-2-yl)-2-oxopropionate are obtained, the characteristics of which are as follows:

MS (ES+) spectrum: m/z=239 [MH]+

Melting point=38° C. (Köfler bench).

1H NMR spectrum (400 MHz, DMSO-d6, δ in ppm): 1.30 (t, J=7.0 Hz, 3H); 4.29 (q, J=7.0 Hz, 2H); 7.12 (s, 1H); 7.57 (dd, J=5.5 and 8.5 Hz, 1H); 8.66 (broad d, J=8.5 Hz, 1H); 8.85 (broad d, J=5.5 Hz, 1H); 14.9 (broad m, 1H).

IR spectrum (KBr): 1722; 1644; 1560; 1532; 1346; 1231; 1141; 1024 and 777 cm$^{-1}$ Ethyl 1H-pyrrolo[3,2-b]pyridine-2-carboxylate 18.4 g of ethyl 3-(3-nitropyridin-2-yl)-2-oxopropionate and 5.5 g of 10% palladium-on-charcoal are added to 500 ml of ethanol, and the reaction mixture is hydrogenated under 2 bar for 3 hours at 20° C. The reaction mixture is then filtered over a thin layer of silica gel and the filtrate is concentrated under reduced pressure, to give 14.1 g of ethyl 1H-pyrrolo[3,2-b]-pyridine-2-carboxylate, the characteristics of which are as follows:

MS (ES+) spectrum: m/z=191 [MH]+

Melting point=176-178° C. (Köfler bench).

1H NMR spectrum (400 MHz, DMSO-d6, δ in ppm): 1.36 (t, J=7.0 Hz, 3H); 4.37 (q, J=7.0 Hz, 2H); 7.20 (broad s, 1H); 7.27 (dd, J=4.5 and 8.5 Hz, 1H); 7.84 (broad d, J=8.5 Hz, 1H); 8.45 (dd, J=1.5 and 4.5 Hz, 1H); 12.15 (broad m, 1H).

Ethyl 3-bromo-1H-pyrrolo[3,2-b]pyridine-2-carboxylate 0.9 g of pyridinium tribromide in 5 ml of pyridine is added slowly, at 0° C. under argon, to a solution of 0.5 g of ethyl 1H-pyrrolo[3,2-b]pyridine-2-carboxylate in 12 ml of pyridine. The solution is then heated at 50° C. for 15 min and then poured onto 100 ml of ice-cold water. The solid formed is filtered off, washed with water, and filter-dried. After drying under vacuum, 0.56 g of ethyl 3-bromo-1H-pyrrolo[3,2-b]pyridine-2-carboxylate are obtained, the characteristics of which are as follows:

MS (ES+) spectrum: m/z=270 [MH]+

Melting point=180° C. (Köfler bench).

IR spectrum (KBr): 2983; 2841; 2681; 1711; 1513; 1374; 1346; 1261 1209; 1012; 767 and 651 cm$^{-1}$ Ethyl 3-(4-nitrophenyl)-1H-pyrrolo[3,2-b]pyridine-2-carboxylate 3 g of potassium carbonate and 0.8 g of palladium tetrakis(triphenylphosphine) are added to a solution of 2 g of ethyl 3-bromo-1H-pyrrolo[3,2-b]pyridine-2-carboxylate and 1.5 g of 4-nitrophenylboronic acid in 50 ml of dioxane. The mixture is refluxed for 20 hours, and then filtered. The filtrate is concentrated under reduced pressure and the residue is purified by chromatography on a silica column, elution being carried out with a mixture of cyclohexane and ethyl acetate (50/50 by volume), to give 0.52 g of ethyl 3-(4-nitrophenyl)-1H-pyrrolo[3,2-b]pyridine-2-carboxylate, the characteristics of which are as follows:

MS spectrum (ES+): m/z=312 [MH]+

Melting point=234-236° C. (Köfler bench).

1H NMR spectrum (300 MHz, DMSO-d6, δ in ppm): 1.25 (t, J=7.0 Hz, 3H); 4.32 (q, J=7.0 Hz, 2H); 7.38 (dd, J=4.5 and 8.5 Hz, 1H); 7.94 (dd, J=1.5 and 8.5 Hz, 1H); 7.99 (broad d, J=9.0 Hz, 2H); 8.30 (broad d, J=9.0 Hz, 2H); 8.52 (dd, J=1.5 and 4.5 Hz, 1H); 12.4 (broad s, 1H).

IR spectrum (KBr): 3371; 1741; 1598; 1508; 1345; 1252 1158; 857 and 771 cm$^{-1}$ 3-(4-Nitrophenyl)-1H-pyrrolo[3,2-b]pyridine-2-carboxamide A solution of 0.4 g of ethyl 3-(4-nitrophenyl)-1H-pyrrolo[3,2-b]pyridine-2-carboxylate in 10 ml of 7N ammoniacal methanol is heated at 100° C. for 16 hours in a closed container. The solvent is then concentrated under reduced pressure and the residue is purified by chromatography on a silica column, elution being carried out with ethyl acetate, to give 0.16 g of 3-(4-nitrophenyl-1H-pyrrolo[3,2-b]pyridine-2-carboxamide, the characteristics of which are as follows:

MS spectrum (ES+): m/z=283 [MH]+

Melting point >260° C. (Köfler bench).

1H NMR spectrum (400 MHz, DMSO-d6, δ in ppm): 7.33 (broad dd, J=4.5 and 8.5 Hz, 1H); 7.82 (broad m, 2H); 7.91 (broad d, J=8.5 Hz, 1H); 8.16 (broad d, J=8.5 Hz, 2H); 8.33 (broad d, J=8.5 Hz, 2H); 8.52 (broad d, J=4.5 Hz, 1H); 12.25 (broad m, 1H).

3-(4-Aminophenyl)-1H-pyrrolo[3,2-b]pyridine-2-carboxamide 0.113 g of Pd/C (10%) is added to a solution of 0.15 g of 3-(4-nitrophenyl)-1H-pyrrolo[3,2-b]pyridine-2-carboxamide in 10 ml of methanol. After stirring at 22° C. for 3.5 hours under 2 bar of hydrogen, the reaction medium is filtered over silica gel and then concentrated under reduced pressure, to give 0.1 g of 3-(4-aminophenyl)-1H-pyrrolo[3,2-b]pyridine-2-carboxamide, the characteristics of which are as follows:

MS spectrum (ES+): m/z=253 [MH]+

Melting point 236-238° C. (Köfler bench).

1H NMR spectrum (300 MHz, DMSO-d6, δ in ppm): 5.20 (broad s, 2H); 6.46 (broad m, 1H); 6.68 (broad d, J=8.5 Hz, 2H); 7.20 (dd, J=4.5 and 8.5 Hz, 1H); 7.28 (broad d, J=8.5 Hz, 2H); 7.62 (broad m, 1H); 7.78 (broad d, J 8.5 Hz, 1H); 8.35 (broad d, J=4.5 Hz, 1H); 11.65 broad m, 1H).

3-{4-[3-(2-Fluoro-5-trifluoromethylphenyl)-ureido]phenyl}-1H-pyrrolo[3,2-b]pyridine-2-carboxamide 73 mg of 2-fluoro-5-trifluoromethylphenyl isocyanate are added to a solution of 80 mg of 3-(4-aminophenyl)-1H-pyrrolo[3,2-b]pyridine-2-carboxamide in 18 ml of tetrahydrofuran. After stirring for 1 hour, the mixture is concentrated under reduced pressure and the residue is purified by chromatography on a silica column, elution being carried out with a mixture of cyclohexane and ethyl acetate (20/80 by volume) to give 110 mg of 3-{4-[3-(2-fluoro-5-trifluoromethylphenyl)-ureido]phenyl}-1H-pyrrolo[3,2-b]pyridine-2-carboxamide, the characteristics of which are as follows:

MS spectrum (ES+): m/z=458 [MH]+

Melting point 206-208° C. (Köfler bench).

1H NMR spectrum (300 MHz, DMSO-d6, δ in ppm): 6.91 (broad m, 1H); 7.24 (dd, J=4.5 and 8.5 Hz, 1H); 7.39 (broad m, 1H); 7.51 (partially masked m, 1H); 7.56 (broad d, J=8.5 Hz, 2H); 7.64 (broad d, J=8.5 Hz, 2H); from 7.60 to 7.71 (partially masked broad m, 1H); 7.82 (dd, J=1.5 and 8.5 Hz, 1H); 8.40 (dd, J=1.5 and 4.5 Hz, 1H); 8.65 (broad dd, J=2.5 and 7.5 Hz, 1H); 8.96 (broad m, 1H); 9.31 (broad s, 1H); from 11.7 to 11.9 (very broad m, 1H).

IR spectrum (KBr): 3456; 3382; 1717; 1659; 1600; 1543; 1442; 1340; 1312; 1193; 1167; 1118; 1069 and 774 cm$^{-1}$

EXAMPLE 3

3-[4-(3-Phenylureido)phenyl]-1H-indole-2-carboxamide

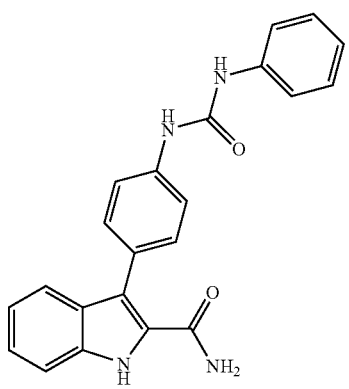

The 3-[4-(3-phenylureido)phenyl]-1H-indole-2-carboxamide was prepared according to method a described above using phenyl isocyanate. Its characteristics are as follows:

MS spectrum (ES+): m/z=371 [MH]+

Melting point=232-234° C.

1H NMR spectrum (400 MHz, DMSO-d6, δ in ppm): 6.43 (broad m, 1H); 6.98 (broad t, J=8.0 Hz, 1H); 7.05 (broad t, J=8.0 Hz, 1H); 7.23 (broad t, J=8.0 Hz, 1H); from 7.39 to 7.52 (m, 7H); 7.59 (broad d, J=8.5 Hz, 2H); 8.72 (broad s, 1H); 8.80 (broad s, 1H); 11.6 (broad s, 1H).

IR spectrum (KBr): 3460; 3384; 3325; 1654; 1596; 1540; 1499; 1312; 1231 and 747 cm$^{-1}$

EXAMPLE 4

3-[4-(3-m-Tolylureido)phenyl]-1H-indole-2-carboxamide

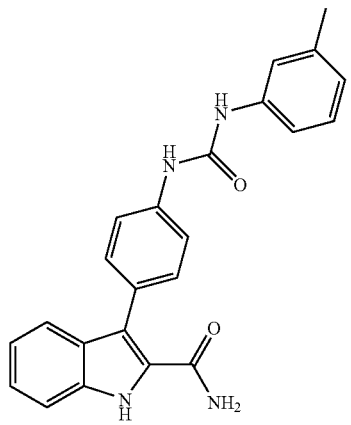

The 3-[4-(3-m-tolylureido)phenyl]-1H-indole-2-carboxamide was prepared according to method a described above, using 3-methylphenyl isocyanate. Its characteristics are as follows:

MS spectrum (ES+): m/z=385 [MH]+

Melting point=140-142° C.

1H NMR spectrum (300 MHz, DMSO-d6, δ in ppm): 2.30 (s, 3H); 6.42 (broad m, 1H); 6.80 (broad d, J=8.0 Hz, 1H); 7.05 (broad t, J=8.0 Hz, 1H); from 7.13 to 7.30 (m, 3H); 7.32 (broad s, 1H); from 7.38 to 7.53 (m, 5H); 7.59 (broad d, J=8.5 Hz, 2H); 8.69 (broad s, 1H); 8.83 (broad s, 1H); 11.6 (broad s, 1H).

IR spectrum (KBr): 3461; 3377; 1655; 1592; 1542; 1218 and 746 cm$^{-1}$

EXAMPLE 5

3-[4-(3-Trifluoromethylphenylureido)phenyl]-1H-indole-2-carboxamide

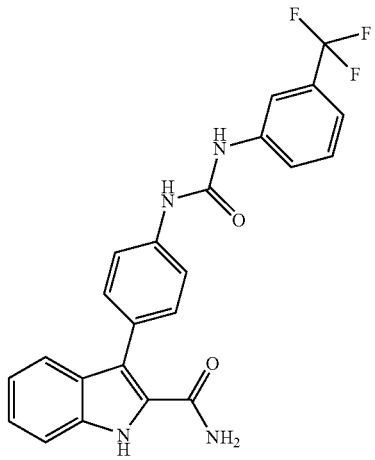

The 3-[4-(3-trifluoromethylphenylureido)phenyl]-1H-indole-2-carboxamide was prepared according to method a described above using 3-trifluoromethylphenyl isocyanate. Its characteristics are as follows:

MS spectrum (ES+): m/z=439 [MH]+

Melting point=156-158° C.

1H NMR spectrum (300 MHz, DMSO-d6, δ in ppm): 6.45 (broad m, 1H); 7.05 (broad t, J=7.5 Hz, 1H); 7.23 (broad t, J=7.5 Hz, 1H); 7.32 (broad d, J=8.5 Hz, 1H); 7.43 (broad d, J=8.5 Hz, 2H); from 7.38 to 7.64 (m, 5H); 7.61 (broad d, J=8.5 Hz, 2H); 8.04 (broad s, 1H); 8.97 (broad s, 1H); 9.15 (broad s, 1H); 11.6 (broad s, 1H).

IR spectrum (KBr): 3462; 3378; 1654; 1590; 1542; 1448; 1337; 1312; 1230; 1125; 1070; 746 and 698 cm$^{-1}$ EXAMPLE 6
3-[4-(3,5-Dimethylphenylureido)phenyl]-1H-indole-2-carboxamide

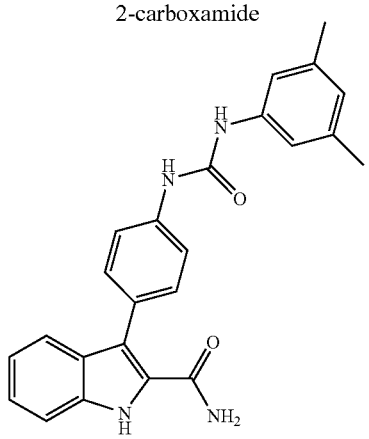

The 3-[4-(3,5-dimethylphenylureido)phenyl]-1H-indole-2-carboxamide was prepared according to method a described above using 3,5-dimethylphenyl isocyanate. Its characteristics are as follows:

MS spectrum (ES+): m/z=399 [MH]+

Melting point=168-170° C.

1H NMR spectrum (400 MHz, DMSO-d6, δ in ppm): 2.24 (s, 6H); 6.43 (broad m, 1H); 6.62 (broad s, 1H); 7.05 (broad t, J=8.0 Hz, 1H); 7.10 (broad s, 2H); 7.23 (broad t, J=8.0 Hz, 1H); from 7.39 to 7.53 (m, 5H); 7.58 (broad d, J=8.5 Hz, 2H); 8.60 (broad s, 1H); 8.82 (broad s, 1H); 11.6 (broad s, 1H).

IR spectrum (KBr): 3459; 3375; 1654; 1586; 1541; 1310; 1215; 851 and 745 cm$^{-1}$ EXAMPLE 7
3-[4-(2-Fluorophenylureido)phenyl]-1H-indole-2-carboxamide

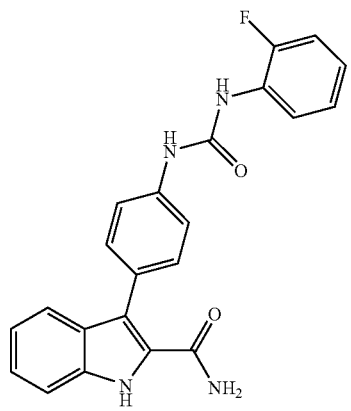

The 3-[4-(2-fluorophenylureido)phenyl]-1H-indole-2-carboxamide was prepared according to method a described above using 2-florophenyl isocyanate. Its characteristics are as follows:

MS spectrum (ES+): m/z=389 [MH]+

Melting point=146-148° C.

1H NMR spectrum (400 MHz, DMSO-d6, δ in ppm): 6.46 (broad m, 1H); from 6.98 to 7.08 (m, 2H); 7.15 (broad t, J=8.0 Hz, 1H); from 7.20 to 7.28 (m, 2H); 7.43 (broad d, J=8.5 Hz, 2H); from 7.40 to 7.52 (masked m, 1H); 7.46 (broad d, J=8.0 Hz, 1H); 7.49 (broad m, 1H); 7.59 (broad d, J=8.5 Hz, 2H); 8.18 (broad t, J=8.0 Hz, 1H); 8.64 (broad s, 1H); 9.24 (broad s, 1H); 11.6 (broad s, 1H).

IR spectrum (KBr): 3457; 3374; 1651; 1596; 1540; 1455; 1313 and 747 cm$^{-1}$

EXAMPLE 8

3-{4-[3-(2-Fluoro-5-trifluoromethylphenyl)-ureido]phenyl}-1-methyl-1H-indole-2-carboxamide

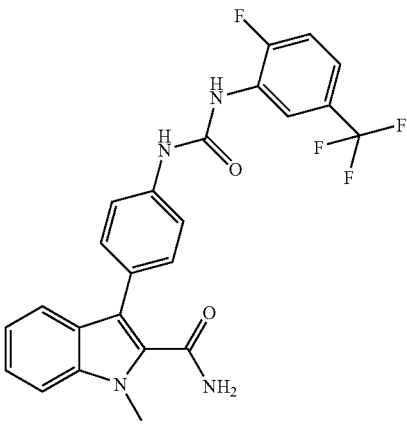

The 3-{4-[3-(2-fluoro-5-trifluoromethylphenyl)ureido]phenyl}-1-methyl-1H-indole-2-carboxamide was prepared according to method a described above using 3-(4-nitrophenyl)-1H-indole-2-carboxamide (example 1):

1-Methyl-3-(4-nitrophenyl)-1H-indole-2-carboxamide 0.047 g of sodium hydride and then 73 μl of methane iodide are added to a solution of 0.3 g of 3-(4-nitro-phenyl)-1H-indole-2-carboxamide in 8 ml of anhydrous dimethylformamide under argon. The reaction mixture is stirred at ambient temperature for 2 hours and 45 ml of water are added. The solid formed is filtered off, washed with 3 times 15 ml of water, and filter-dried. After drying under vacuum, 0.22 g of 1-methyl-3-(4-nitrophenyl)-1H-indole-2-carboxamide are obtained, the characteristics of which are as follows:

MS spectrum (ES+): m/z=389 [MH]+

Melting point=146-148° C.

1-Methyl-3-(4-aminophenyl)-1H-indole-2-carboxamide 0.2 g of 1-methyl-3-(4-nitrophenyl)-1H-indole-2-carboxamide and 0.14 g of 10% palladium-on-charcoal are added to 8 ml of methanol and the reaction mixture is hydrogenated under 5 bar for 4 hours and 30 minutes at 25° C. The reaction mixture is then filtered over a thin layer of silica gel and the filtrate is concentrated under reduced pressure, to give 0.91 g of 1-methyl-3-(4-aminophenyl)-1H-indole-2-carboxamide, the characteristics of which are as follows:

MS spectrum (ES+): m/z=[MH]+
Melting point=96-98° C.
1H NMR spectrum (400 MHz, DMSO-d6, δ in ppm): 3.82 (s, 3H); 5.11 (broad s, 2H); 6.65 (broad d, J=8.0 Hz, 2H); 7.08 (broad t, J=8.0 Hz, 1H); 7.15 (broad d, J=8.0 Hz, 2H); 7.21 (broad m, 1H); 7.25 (broad t, J=8.0 Hz, 1H); 7.50 (broad d, J=8.0 Hz, 1H); 7.53 (broad d, J=8.0 Hz, 1H); 7.61 (broad m, 1H).

3-{4-[3-(2-Fluoro-5-trifluoromethylphenyl)ureido]-phenyl}-1-methyl-1H-indole-2-carboxamide 0.075 g of 2-fluoro-5-trifluoromethylphenyl isocyanate is added to a solution of 0.086 g of 1-methyl-3-(4-aminophenyl)-1H-indole-2-carboxamide in 18 ml of tetrahydrofuran and the stirring is continued for 1 hour. 5 ml of methanol are added, the reaction mixture is then concentrated under reduced pressure, and the residue is purified by chromatography on a silica column, elution being carried out with a mixture of cyclohexane and ethyl acetate (20/80 by volume), to give 90 mg of 3-{4-[3-(2-fluoro-5-trifluoromethyl-phenyl)ureido]phenyl}-1-methyl-1H-indole-2-carboxamide, the characteristics of which are as follows:

MS spectrum (ES+): m/z=471 [MH]+
Melting point=>260° C.
1H NMR spectrum (300 MHz, DMSO-d6, δ in ppm): 3.83 (s, 3H); 7.13 (broad t, J=8.0 Hz, 1H); 7.29 (broad t, J=8.0 Hz, 1H); 7.39 (m, 1H); 7.45 (broad d, J=8.5 Hz, 2H); from 7.49 to 7.58 (m, 5H); 7.62 (broad d, J=8.0 Hz, 1H); 7.71 (broad m, 1H); 8.65 (dd, J=2.5 and 7.5 Hz, 1H); 8.95 (broad m, 1H); 9.28 (broad m, 1H).
IR spectrum (KBr): 3477; 3351; 3308; 3281; 3181; 1712; 1650; 1600; 1537; 1442; 1310; 1116; 821 and 743 cm$^{-1}$

EXAMPLE 9

3-{4-[3-(3-Chloro-4-trifluoromethylphenyl)-ureido]phenyl}-1H-indole-2-carboxamide

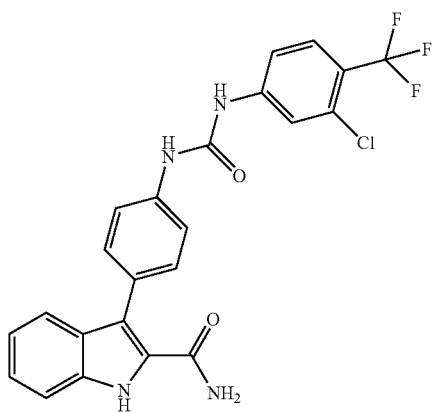

The 3-{4-[3-(3-chloro-4-trifluoromethylphenyl)ureido]-phenyl}-1H-indole-2-carboxamide was prepared according to method a described above using 3-chloro-4-trifluoromethylphenyl isocyanate. Its characteristics are as follows:

MS spectrum (ES+): m/z=473 [MH]+
Melting point=168-170° C.
1H NMR spectrum (300 MHz, DMSO-d6, δ en ppm): 6.49 (broad m, 1H); 7.05 (broad t, J=8.0 Hz, 1H); from 7.40 to 7.54 (m, 6H); 7.60 (broad d, J=8.5 Hz, 2H); 7.75 (d, J=9.0 Hz, 1H); 7.95 (d, J=1.5 Hz, 1H); 9.08 (broad m, 1H); 9.38 (broad m, 1H); 11.6 (broad m, 1H).
IR spectrum (KBr): 3463; 3343; 1650; 1590; 1536; 1312; 1100 and 745 cm$^{-1}$

EXAMPLE 10

3-{4-[3-(5-tert-butylisoxazol-3-yl)ureido]-phenyl}-1H-indole-2-carboxamide

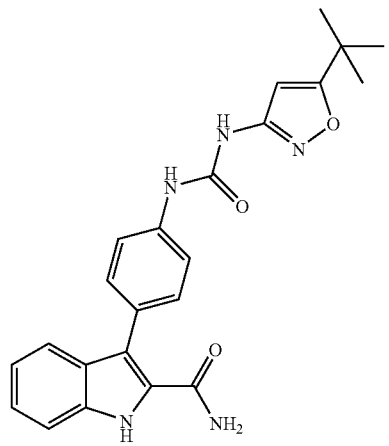

The 3-{4-[3-(5-tert-butylisoxazol-3-yl)ureido]phenyl}-1H-indole-2-carboxamide was prepared according to method a described above using 5-tert-butylisoxazole-3-isocyanate. Its characteristics are as follows:

MS spectrum (ES+): m/z=418 [MH]+
Melting point=176-178° C.
1H NMR spectrum (300 MHz, DMSO-d6, δ in ppm): 1.31 (s, 9H); 6.47 (broad m, 1H); 6.52 (s, 1H); 7.05 (broad t, J=8.0 Hz, 1H); 7.23 (broad t, J=8.0 Hz, 1H); from 7.39 to 7.52 (m, 5H); 7.58 (broad d, J=8.5 Hz, 2H); 8.94 (broad s, 1H); 9.52 (broad s, 1H); 11.6 (broad s, 1H).
IR spectrum (KBr): 3461; 3275; 2968; 1695; 1653; 1607; 1539; 1280 and 745 cm$^{-1}$

EXAMPLE 11

3-{4-[3-(4-Trifluoromethoxyphenyl)ureido]-phenyl}-1H-indole-2-carboxamide

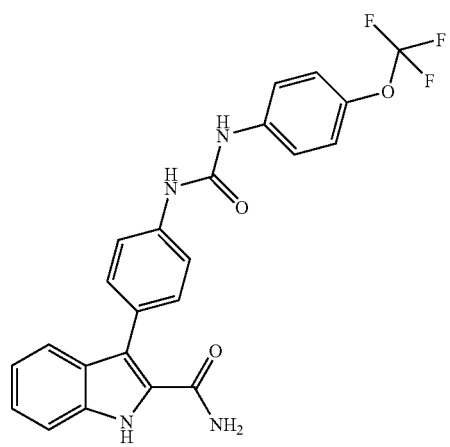

The 3-{4-[3-(4-trifluoromethoxyphenyl)ureido]phenyl}-1H-indole-2-carboxamide was prepared according to method a described above using 4-trifluoromethoxyphenyl isocyanate. Its characteristics are as follows:

MS spectrum (ES+): m/z=455 [MH+]

Melting point: 162-164° C.

Elemental analysis: C %: 60.92; H %: 3.66; N %: 11.85 (theoretical: C %: 60.79; H %: 3.77; N %: 12.33)

1H NMR spectrum (300 MHz, DMSO-d6, δ in ppm): 6.44 (broad m, 1H); 7.05 (broad t, J=8.0 Hz, 1H); 7.23 (broad t, J=8.0 Hz, 1H); 7.30 (broad d, J=8.5 Hz, 2H); from 7.38 to 7.52 (m, 5H); 7.58 (m, 4H); 8.86 (broad s, 1H); 8.94 (broad s, 1H); 11.6 (broad s, 1H).

EXAMPLE 12

3-{4-[3-(2-Methoxy-5-trifluoromethylphenyl)ureido]phenyl}-1H-indole-2-carboxamide

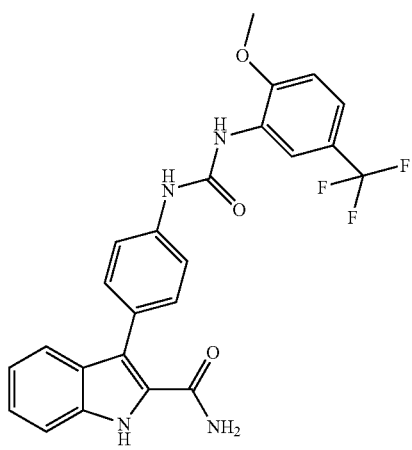

The 3-{4-[3-(2-methoxy-5-trifluoromethylphenyl)ureido]-phenyl}-1H-indole-2-carboxamide was prepared according to method a described above using 2-methoxy-5-trifluoromethylphenyl isocyanate. Its characteristics are as follows:

MS spectrum (ES+): m/z=469 [MH+]

Melting point: 178-180° C.

1H NMR spectrum (300 MHz, DMSO-d6, δ in ppm): 3.99 (s, 3H); 6.46 (broad m, 1H); 7.05 (broad t, J=8.0 Hz, 1H); from 7.19 to 7.27 (m, 2H); 7.33 (dd, J=2.0 and 8.5 Hz, 1H); from 7.40 to 7.54 (m, 5H); 7.60 (broad d, J=8.5 Hz, 2H); 8.56 (broad s, 1H); 8.59 (d, J=2.0 Hz, 1H); 9.55 (broad s, 1H); 11.6 (broad m, 1H).

IR spectrum (KBr): 3463; 3342; 1655; 1593; 1540; 1447; 1269; 1134 and 746 cm$^{-1}$

EXAMPLE 13

3-[4-(2-Fluoro-5-trifluoromethylbenzenesulfonylamino)phenyl]-1H-indole-2-carboxamide

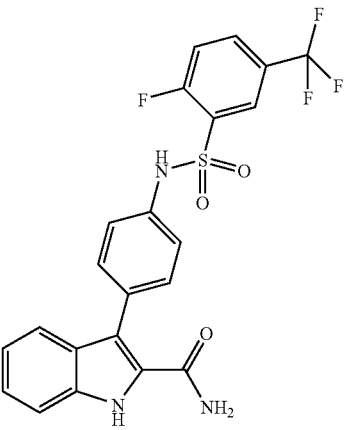

162 mg of 2-fluoro-5-trifluoromethylphenylsulfonyl chloride in 6 ml of pyridine are added dropwise to a solution of 100 mg of 3-(4-aminophenyl)-1H-indole-2-carboxamide (example 1) in 12 ml of pyridine at 0° C. The mixture is stirred at ambient temperature for 6 hours and then poured into 50 ml of ice-cold water, and the precipitate formed is filtered off. After purification by flash chromatography on a silica column, elution being carried out with a mixture of cyclohexane and ethyl acetate (20/80 by volume), 50 mg of 3-[4-(2-fluoro-5-trifluoromethylbenzenesulfonylamino)phenyl]-1H-indole-2-carboxamide are obtained, the characteristics of which are as follows:

MS (ES+): m/z=478 [MH+]

Melting point: 176-178° C.

Elemental analysis: C %: 55.11; H %: 3.47; N %: 8.34 (theoretical: C %: 55.35; H %: 3.17; N %: 8.80)

1H NMR spectrum (300 MHz, DMSO-d6, δ in ppm): 6.50 (broad m, 1H); 7.02 (broad t, J=8.0 Hz, 1H); from 7.18 to 7.25 (m, 3H); 7.31 (broad d, J=8.0 Hz, 1H); from 7.35 to 7.50 (m, 4H); 7.72 (broad t, J=8.0 Hz, 1H); from 8.07 to 8.18 (m, 2H); 10.9 (broad s, 1H); 11.6 (broad s, 1H).

EXAMPLE 14

3-[4-(2,3-Dichlorobenzenesulfonylamino)-phenyl]-1H-indole-2-carboxamide

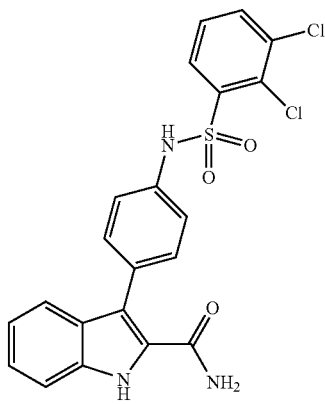

The 3-[4-(2,3-dichlorobenzenesulfonylamino)phenyl]-1H-indole-2-carboxamide was prepared according to example 13 using 3,4-dichlorophenylsulfonyl chloride. Its characteristics are as follows:

MS spectrum (ES+): m/z=460 [MH+]

Melting point: >260° C.

1H NMR spectrum (300 MHz, DMSO-d6, δ in ppm): 6.54 (broad m, 1H); 7.02 (broad t, J=8.0 Hz, 1H); from 7.17 to 7.25 (m, 3H); from 7.31 to 7.50 (m, 5H); 7.58 (t, J=8.0 Hz, 1H); 7.95 (dd, J=2.5 and 8.0 Hz, 1H); 8.10 (dd, J=2.5 and 8.0 Hz, 1H); 10.9 (broad m, 1H); 11.6 (broad s, 1H).

IR spectrum (KBr): 3476; 3422; 3389; 3358; 1670; 1651; 1583; 1540; 1404; 1343; 1166; 935; 748 and 596 cm$^{-1}$

EXAMPLE 15

3-{4-[3-(5-tert-Butyl-2-p-tolyl-2H-pyrazol-3-yl)ureido]phenyl}-1H-indole-2-carboxamide

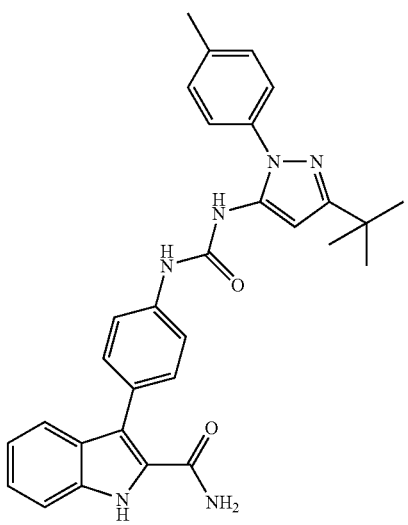

43 mg of triphosgene followed by 110 μl of triethylamine at 0° C. are added to a solution of 100 mg of 3-(4-aminophenyl)-1H-indole-2-carboxamide (example 1) in 18 ml of tetrahydrofuran. The mixture is stirred for one hour at ambient temperature and then 110 mg of 5-tert-butyl-2-p-tolyl-2H-pyrazol-3-ylamine are added. The mixture is stirred for one hour and concentrated under reduced pressure, and the residue is triturated with 2 ml of ethyl acetate, to give a white solid. After filtration and drying, 150 mg of 3-{4-[3-(5-tert-butyl-2-p-tolyl-2H-pyrazol-3-yl)ureido]phenyl}-1H-indole-2-carboxamide are obtained, the characteristics of which are as follows:

MS spectrum (ES+): m/z=507 [MH+]

Melting point:>260° C.

1H NMR spectrum: (300 MHz, DMSO-d6, δ in ppm): 1.29 (s, 9H); 2.39 (s, 3H); 6.38 (s, 1H); 6.41 (broad m, 1H); 7.05 (broad t, J=7.5 Hz, 1H); 7.22 (broad t, J=7.5 Hz, 1H); 7.35 (broad d, J=8.5 Hz, 2H); from 7.37 to 7.48 (m, 7H); 7.54 (broad d, J=8.5 Hz, 2H); 8.37 (broad s, 1H); 9.13 (broad s, 1H); 11.65 (broad s, 1H).

IR spectrum (KBr): 3457; 3374; 1651; 1596; 1540; 1455; 1313; 1246; 1181; 854 and 747 cm$^{-1}$

EXAMPLE 16

3-{4-[3-(2-Fluoro-5-methylphenyl)ureidophenyl]-1H-indole-2-carboxamide

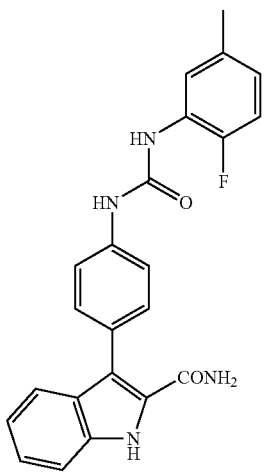

0.115 cm³ (0.876 mmol) of 2-fluoro-5-methylphenyl isocyanate is added, at a temperature in the region of 20° C., under an argon atmosphere, to 0.2 g (0.796 mmol) of 3-(4-aminophenyl)-1H-indole-2-carboxamide in solution in 10 cm³ of tetrahydrofuran. After stirring for 18 hours at a temperature in the region of 20° C., the reaction mixture is concentrated to dryness under reduced pressure (2.7 kPa), to give 400 mg of a residue which is purified by flash chromatography [eluent: ethyl acetate/cyclohexane (7/3 by volume)]. After concentration under reduced pressure of the fractions containing the expected product, 250 mg of a yellow residue are obtained, which residue is stirred in 10 cm³ of dichloromethane and then filtered and dried under reduced pressure (2.7 kPa), to give 180 mg of 3-{4-[3-(2-fluoro-5-methylphenyl)ureido]phenyl}-1H-indole-2-carboxamide, in the form of a beige solid that melts at 220° C.;

1H NMR (300 MHz, (CD3)2SO d6, −δ in ppm): 2.28 (s: 3H); 6.46 (broad s: 1H); 6.81 (m: 1H); 7.06 (broad t, J=8 Hz: 1H); 7.11 (broad t, J=10 Hz: 1H); 7.23 (broad t, J=8 Hz: 1H); from 7.36 to 7.53 (m: 5H); 7.59 (d, J=9 Hz: 2H); 8.02 (broad d, J=8 Hz: 1H); 8.55 (broad s: 1H); 9.21 (s: 1H); 11.61 (s: 1H); MS-ES+: m/z=403(+)=(M+H) (+);

MS-ES: m/z=401(−)=(M−H)(−).

EXAMPLE 17

3-{4-[3-(5-Dimethylamino-2-fluorophenyl)-ureido]phenyl}-1H-indole-2-carboxamide

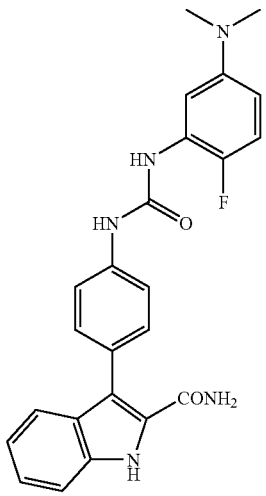

18 cm³ (2.52 mmol) of a solution of 5-dimethylamino-2-fluorophenyl isocyanate in 0.14 N tetrahydrofuran followed by 0.1 cm³ (0.796 mmol) of triethylamine are added, at a temperature in the region of 20° C., under an argon atmosphere, to 0.2 g (0.796 mmol) of 3-(4-aminophenyl)-1H-indole-2-carboxamide. After stirring for 18 hours at a temperature in the region of 20° C., the reaction mixture is concentrated to dryness under reduced pressure (2.7 kPa), to give 0.7 g of a brown oil which is purified by flash chromatography [eluent: ethyl acetate/cyclohexane (7/3 by volume)]. After concentration under reduced pressure of the fractions containing the expected product, 220 mg of a yellow residue are obtained, which residue is stirred in 10 cm³ of diethyl ether and then filtered and dried under reduced pressure (2.7 kPa), to give 200 mg of 3-{4-[3-(5-dimethylamino-2-fluorophenyl)ureido]phenyl}-1H-indole-2-carboxamide, in the form of a beige solid that melts at between 180° C. and 220° C.;

1H NMR (300 MHz, (CD3)2SO d6, −δ in ppm): 2.86 (s: 6H); 6.32 (dt, J=3 and 9 Hz: 1H); 6.43 (very broad s: 1H); from 7.00 to 7.08 (m: 2H); 7.23 (t, J=7 Hz: 1H); from 7.38 to 7.54 (m: 5H); 7.59 (d, J=9 Hz: 2H); 7.68 (dd, J=3 and 7 Hz: 1H); 8.45 (broad s: 1H); 9.19 (s: 1H); 11.6 (s: 1H).

MS-ES⁺: m/z=432(+)=(M+H)(+).

The solution of 5-dimethylamino-2-fluorophenyl isocyanate in 0.14 N tetrahydrofuran can be prepared in the following way:

1.09 g (7.1 mmol) of 4-fluoro-N1,N1-dimethylbenzene-1,3-diamine followed by 4.6 cm³ of pyridine are added, at a temperature in the region of 5° C., under an argon atmosphere, to 2.82 g (9.5 mmol) of triphosgene in solution in 150 cm³ of dichloromethane. After stirring for 18 hours at a temperature in the region of 20° C., the reaction mixture is concentrated to dryness under reduced pressure (2.7 kPa), to give a residue which is triturated in 40 cm³ of tetrahydrofuran. After filtration, a solution of 5-dimethylamino-2-fluorophenyl isocyanate in approximately 0.14 N tetrahydrofuran is obtained, which solution is used directly in the subsequent step.

The 4-fluoro-N1,N1-dimethylbenzene-1,3-diamine can be prepared in the following way:

3.23 g (17.54 mmol) of (4-fluoro-3-nitrophenyl)-dimethylamine are added, at a temperature in the region of 20° C., to a suspension of 0.6 g (5.63 mmol) of 10% palladium-on-charcoal in 100 cm³ of methanol. After hydrogenation for 30 minutes in an autoclave under 5 bar of hydrogen, at a temperature in the, region of 25° C., the reaction mixture is filtered, the catalyst is rinsed with 3 times 10 cm³ of methanol, and the filtrate is then concentrated to dryness under reduced pressure (2.7 kPa), to give 2.7 g of 4-fluoro-N1,N1-dimethylbenzene-1,3-diamine, in the form of a brown oil;

MS-EI: m/z=154(+)=(M)(+).

The (4-fluoro-3-nitrophenyl)dimethylamine can be prepared in the following way:

13.27 g (96 mmol) of potassium carbonate are added, at a temperature in the region of 20° C., under an argon atmosphere, to 5 g (32 mmol) of 4-fluoro-3-nitroaniline in solution in 50 cm³ of dimethylformamide, followed, at a temperature in the region of 5° C., by 4.6 cm³ (73.6 mmol) of iodomethane. After stirring for 63 hours at a temperature in the region of 20° C., the reaction mixture is poured into 100 cm³ of water and then extracted with 3 times 100 cm³ of dichloromethane. The organic phases are combined, washed with 3 times 100 cm³ of water, dried over anhydrous magnesium sulfate, filtered, and concentrated to dryness under reduced pressure (2.7 kPa), to give 5.5 g of a residue which is purified by flash chromatography [eluent: ethyl acetate/cyclohexane (2/8 by volume)]. After concentration under reduced pressure of the fractions containing the expected product, 2.78 g of (4-fluoro-3-nitrophenyl)dimethylamine are obtained in the form of an orange-red solid;

MS-ES⁺: m/z=185(+)=(M+H)(+).

EXAMPLE 18

3-{4-[3-(3-Dimethylaminophenyl)ureido]-phenyl}-1H-indole-2-carboxamide

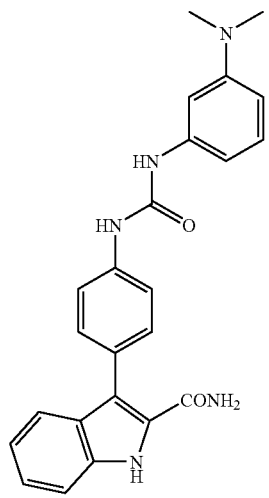

8.5 cm³ (0.8 mmol) of a solution of 3-dimethylaminophenyl isocyanate in 0.14 N tetrahydrofuran, followed by 0.055 cm³ (0.4 mmol) of triethylamine, are added, at a temperature in the region of 20° C., under an argon atmosphere, to 0.1 g (0.4 mmol) of 3-(4-aminophenyl)-1H-indole-2-carboxamide. After stirring for 18 hours at a temperature in the region of 20° C., 0.1 cm³ of water is added and the reaction mixture is then concentrated to dryness under reduced pressure (2.7 kPa), to give 0.7 g of a residue which is purified by flash chromatography [eluent: dichloromethane/methanol (95/5 by volume)]. After concentration under reduced pressure of the fractions containing the expected product, 81 mg of 3-{4-[3-(3-dimethylaminophenyl)ureido]phenyl}-1H-indole-2-carboxamide are obtained in the form of a white solid that melts at between 160° C. and 220° C.;

1H NMR (300 MHz, (CD3)2SO d6, −δ in ppm): 2.89 (s: 6H); 6.38 (d, J=9 Hz: 1H); 6.42 (broad s: 1H); 6.74 (d, J=9 Hz: 1H); 6.94 (broad s: 1H); from 7.00 to 7.12 (m: 2H); 7.23 (t, J=7 Hz: 1H); 7.40 (d, J=8 Hz: 2H); 7.43 (partially masked d, J=8 Hz: 1H); 7.46 (d, J=8 Hz: 1H); 7.49 (broad s: 1H); 7.58 (d, J=8 Hz: 2H), 8.56 (s: 1H); 8.72 (s: 1H); 11.60 (s: 1H);

MS-ES⁺: m/z=414(+)=(M+H)(+).

The solution of 3-dimethylaminophenyl isocyanate in 0.14 N tetrahydrofuran can be prepared in the following way:

1.46 g (7 mmol) of N1,N1-dimethylbenzene-1,3-diamine dihydrochloride, followed by 9.9 cm³ (71.64 mmol) of triethylamine, are added, at a temperature in the region of 5° C., under an argon atmosphere, to 2.82 g (9.5 mmol) of triphosgene in solution in 150 cm³ of dichloromethane. After stirring for 20 hours at a temperature in the region of 20° C., the reaction mixture is concentrated to dryness under reduced pressure (2.7 kPa), to give a residue which is triturated in 50 cm³ of tetrahydrofuran. After filtration, a solution of 3-dimethylaminophenyl isocyanate in approximately 0.14 N tetrahydrofuran is obtained, which solution is used directly in the subsequent step.

EXAMPLE 19

3-{4-[3-(2-Pyrrolidin-1-ylmethyl-5-trifluoromethylphenyl)ureido]phenyl}-1H-indole-2-carboxamide

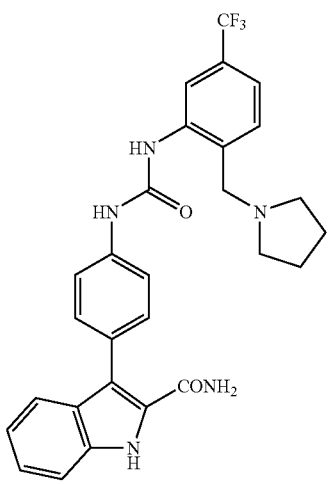

19.7 mg (0.066 mmol) of triphosgene, followed by 0.056 cm³ (0.4 mmol) of triethylamine, are added, at a temperature in the region of 20° C., under an argon atmosphere, to 0.05 g (0.2 mmol) of 4-(4-aminophenyl)-1H-pyrrole-3-carboxamide in solution in 10 cm³ of tetrahydrofuran. After stirring for one hour at a temperature in the region of 20° C., 48.61 mg (0.2 mmol) of 2-pyrrolidin-1-ylmethyl-5-trifluoromethylphenylamine in solution in 2 cm³ of tetrahydrofuran are added. After stirring for 3 hours at a temperature in the region of 20° C., the reaction mixture is concentrated to dryness under reduced pressure (2.7 kPa), to give 0.15 g of a residue which is purified by flash chromatography [eluent: dichloromethane/methanol (95/5 by volume)]. After concentration under reduced pressure of the fractions containing the expected product, 45 mg of 3-{{4-[3-(2-pyrrolidin-1-ylmethyl-5-trifluoromethylphenyl)ureido]phenyl}-1H-indole-2-carboxamide, are obtained in the form of a beige solid that melts at between 190° C. and 250° C.;

1H NMR (300 MHz, (CD3)2SO d6, −δ in ppm): 1.74 (m: 4H); 2.50 (partially hidden m: 4H); 3.73 (s: 2H); 6.52 (broad s: 1H); 7.05 (t, J=7 Hz: 1H); 7.23 (t, J=7 Hz: 1H); 7.31 (d, J=8 Hz: 1H); from 7.40 to 7.52 (m: 6H); 7.63 (d, J=8 Hz: 2H); 8.37 (s: 1H); 9.63 (s: 1H); 9.86 (s: 1H); 11.68 (broad s: 1H).

MS-ES⁺: m/z=521(+)=(M+H)(+).

The 2-pyrrolidin-1-ylmethyl-5-trifluoromethylphenylamine can be prepared in the following way: 0.44 g (1.604 mmol) of 1-(2-nitro-4-trifluoromethylbenzyl)pyrrolidine is added, at a temperature in the region of 25° C., to a suspension of 0.05 g (0.47 mmol) of 10% palladium-on-charcoal in 25 cm³ of methanol. After hydrogenation for 3 hours in an autoclave under 5 bar of hydrogen, at a temperature in the region of 25° C., the reaction mixture is filtered, the catalyst is rinsed with 3 times 5 cm³ of methanol, and the filtrate is then concentrated to dryness under reduced pressure (2.7 kPa), to give 0.4 g of 2-pyrrolidin-1-ylmethyl-5-trifluoromethylphenylamine in the form of an orange oil;

MS-ES⁺: m/z=245(+)=(M+H)(+).

The 1-(2-nitro-4-trifluoromethylbenzyl)pyrrolidine can be prepared in the following way:

0.35 cm³ (4.174 mmol) of pyrrolidine is added, at a temperature in the region of 20° C., under an argon atmosphere, to 0.5 g (2.087 mmol) of 1-chloromethyl-2-nitro-4-trifluoromethylbenzene in solution in 20 cm³ of dichloromethane. After stirring for 16 hours at a temperature in the region of 20° C., the reaction mixture is diluted with 250 cm³ of dichloromethane, washed with 3 times 200 cm³ of water, dried over anhydrous magnesium sulfate, filtered, and concentrated to dryness under reduced pressure (2.7 kPa), to give 458 mg of 1-(2-nitro-4-trifluoromethylbenzyl)pyrrolidine in the form of an oil;

MS-EI: m/z=274(+)=(M)(+); 257(+)=(M-OH)(+); 226 (+)=(M-H₂NO₂) (+); 70 (+)=(C₄H₈N)(+).

EXAMPLE 20

3-{4-[3-(2-Methoxymethyl-5-trifluoromethylphenyl)ureido]phenyl}-1H-indole-2-carboxamide

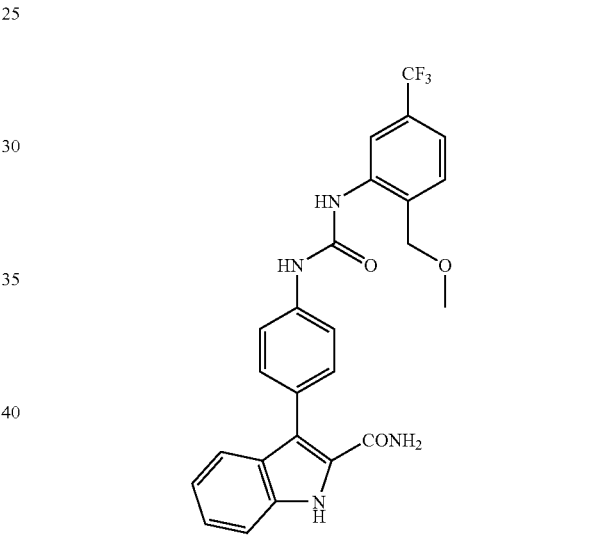

52.5 mg (0.177 mmol) of triphosgene, followed by 0.15 cm³ (1.072 mmol) of triethylamine, are added, at a temperature in the region of 20° C., under an argon atmosphere, to 134.7 mg (0.536 mmol) of 4-(4-aminophenyl)-1H-pyrrole-3-carboxamide in solution in 20 cm³ of tetrahydrofuran. After stirring for 1 hour at a temperature in the region of 20° C., 110 mg (0.536 mmol) of 2-methoxymethyl-5-trifluoromethylphenylamine in solution in 2 cm³ of tetrahydrofuran are added. After stirring for 3 hours at a temperature in the region of 20° C., 0.1 cm³ of water is added and the reaction mixture is then concentrated to dryness under reduced pressure (2.7 kPa), to give 0.4 g of a yellow solid which is purified by flash chromatography [eluent: ethyl acetate/cyclohexane (7/3 by volume)]. After concentration under reduced pressure of the fractions containing the expected product, 20 mg of 3-{4-[3-(2-methoxymethyl-5-trifluoromethylphenyl)ureido]phenyl}-1H-indole-2-carboxamide are obtained in the form of a beige solid that melts at between 170° C. and 220° C.;

1H NMR (300 MHz, (CD3)2SO d6, −δ in ppm): 3.38 (partially masked s: 3H); 4.58 (s: 2H); 6.46 (broad s: 1H); 7.05 (t, J=7 Hz: 1H); 7.23 (t, J=7 Hz: 1H); from 7.32 to 7.51

(m: 6H); 7.56 (d, J=7 Hz: 1H); 7.64 (d, J=9 Hz: 2H); 8.32 (broad s: 1H); 8.77 (very broad s: 1H); 9.96 (very broad s: 1H); 11.63 (very broad s: 1H).

MS-ES+: m/z=482(+)=(M+H)(+).

The 2-methoxymethyl-5-trifluoromethylphenylamine can be prepared in the following way:

0.15 g (0.638 mmol) of 1-methoxymethyl-2-nitro-4-trifluoromethylbenzene is added, at a temperature in the region of 25° C., to a suspension of 0.02 g (0.188 mmol) of 10% palladium-on-charcoal in 20 cm³ of methanol. After hydrogenation for 3 hours in an autoclave under 1 bar of hydrogen, at a temperature in the region of 25° C., the reaction mixture is filtered, the catalyst is rinsed with 3 times 5 cm³ of methanol, and the filtrate is then concentrated to dryness under reduced pressure (2.7 kPa), to give 0.12 g of 2-methoxymethyl-5-trifluoromethylphenylamine in the form of a yellow oil;

MS-ES+: m/z=206(+)=(M+H)(+); 174 (+)=(M-CH₃O)(+).

The 1-methoxymethyl-2-nitro-4-trifluoromethylbenzene can be prepared in the following way:

0.65 cm³ (10 mmol) of iodomethane, followed by 1.163 g (5 mmol) of silver oxide and 0.07 cm³ of water, are added, at a temperature in the region of 20° C., under an argon atmosphere, to 0.222 g (1 mmol) of (2-nitro-4-trifluoromethylphenyl)methanol in solution in 10 cm³ of dichloromethane. After stirring for 18 hours at a temperature in the region of 20° C. in the dark, the reaction mixture is filtered over Celite®. The Celite® is rinsed with 10 cm³ of dichloromethane. The filtrate is then concentrated to dryness under reduced pressure (2.7 kPa). The residue is redissolved in 10 cm³ of dichloromethane, and 0.65 cm³ (10 mmol) of iodomethane, followed by 1.163 g (5 mmol) of silver oxide and 0.07 cm³ of water, are added at a temperature in the region of 20° C., under an argon atmosphere. After stirring for 60 hours at a temperature in the region of 20° C. in the dark, the reaction mixture is filtered over Celite®. The Celite® is rinsed with 10 cm³ of dichloromethane. The filtrate is then concentrated to dryness under reduced pressure (2.7 kPa). The residue is purified by flash chromatography [eluent: dichloromethane]. After concentration under reduced pressure of the fractions containing the expected product, 157 mg of 1-methoxymethyl-2-nitro-4-trifluoromethylbenzene are obtained in the form of an oil;

1H NMR (300 MHz, (CD3)2SO d6, δ in ppm): 3.40 (s: 3H); 4.83 (s: 2H); 7.96 (d, J=8 Hz: 1H); 8.16 (dd, J=8 and 1.5 Hz: 1H); 8.49 (d, J=1.5 Hz: 1H).

The (2-nitro-4-trifluoromethylphenyl)methanol can be prepared in the following way:

1.9 cm³ (1.9 mmol) of a 1M aqueous sodium hydroxide solution are added, at a temperature in the region of 20° C., to 0.5 g (1.9 mmol) of 2-nitro-4-trifluoromethylbenzyl acetate in solution in 50 cm³ of methanol. After stirring for 2 hours at a temperature in the region of 20° C., 20 cm³ of a saturated aqueous sodium phosphate solution are added and the mixture is then extracted with 3 times 50 cm³ of dichloromethane. The organic phases are combined, washed with 50 cm³ of a saturated aqueous sodium chloride solution, dried over anhydrous magnesium sulfate, filtered, and concentrated to dryness under reduced pressure (2.7 kPa), to give 0.424 g of (2-nitro-4-trifluoromethylphenyl)methanol in the form of an oil;

MS-ES⁻: m/z=220(−)=(M−H)(−).

The 2-nitro-4-trifluoromethylbenzyl acetate can be prepared in the following way:

2 g (8.348 mmol) of 1-chloromethyl-2-nitro-4-trifluoromethylbenzene are added, at a temperature in the region of 20° C., under an argon atmosphere, to 20 g (244 mmol) of sodium acetate in solution in 100 cm³ of acetic acid. After stirring for 60 hours at a temperature in the region of 100° C., the reaction mixture is diluted with 200 cm³ of water and then extracted with 2 times 300 cm³ of dichloromethane. The organic phases are combined, washed with 100 cm³ of water, dried over anhydrous magnesium sulfate, filtered, and concentrated to dryness under reduced pressure (2.7 kPa), to give 2.15 g of 2-nitro-4-trifluoromethylbenzyl acetate in the form of an orange oil;

MS-CI: m/z=281(+)=(M+NH₄)(+).

EXAMPLE 21

3-{4-[3-(2-Fluoro-5-trifluoromethylphenyl)-ureido]phenyl}-4-oxy-1H-pyrrolo[3,2-b]pyridine-2-carboxamide

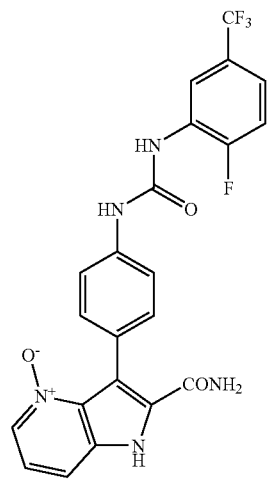

109.5 mg (0.444 mmol) of 3-chloroperoxybenzoic acid in solution in 6 cm³ of dichloromethane are added, at a temperature in the region of 0° C., under an argon atmosphere, to 0.1 g (0.218 mmol) of 3-{4-[3-(2-fluoro-5-trifluoromethylphenyl)ureido]phenyl}-1H-pyrrolo-[3,2-b]pyridine-2-carboxamide in solution in 4 cm³ of chloroform. After stirring for 1 hour at a temperature in the region of 0° C. and then stirring for 24 hours at a temperature in the region of 20° C., the reaction mixture is concentrated to dryness under reduced pressure (2.7 kPa), to give 87 mg of a residue which is purified by flash chromatography [eluent: dichloromethane/methanol/acetonitrile (90/5/5 by volume)]. After concentration under reduced pressure of the fractions containing the expected product, 65 mg of a yellow solid are obtained, which solid is triturated in 4 cm³ of cyclohexane. After filtration and drying under reduced pressure (2.7 kPa) at a temperature in the region of 30° C., 57 mg of 3-{4-[3-(2-fluoro-5-trifluoromethylphenyl)ureido]phenyl}-4-oxy-1H-pyrrolo-[3,2-b]pyridine-2-carboxamide are obtained in the form of a white solid that melts at around 283° C.;

1H NMR (300 MHz, (CD3)2SO d6, −δ in ppm): 6.12 (broad s: 1H); 7.17 (dd, J=9 and 6 Hz: 1H); from 7.35 to 7.55 (m: 3H); 7.37 (d, J=9 Hz: 1H); 7.43 (d, J=9 Hz: 1H); 7.49 (d, J=9 Hz: 2H); 7.69 (broad s: 1H); 7.96 (d, J=6 Hz: 1H); 8.64 (broad d, J=6 Hz: 1H); 9.03 (s: 1H); 9.38 (s: 1H); 12.37 (broad s: 1H);

MS-ES+: m/z=474(+)=(M+H)(+).

EXAMPLE 22

3-{4-[3-(2-Methoxy-5-trifluoromethylphenyl)-ureido]phenyl}-1H-pyrrolo[3,2-b]pyridine-2-carboxamide

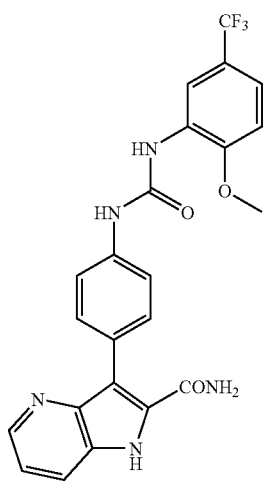

82.4 mg (0.278 mmol) of triphosgene, followed by 0.223 cm³ of triethylamine, are added, at a temperature in the region of 20° C., under an argon atmosphere, to 0.2 g (0.793 mmol) of 3-(4-aminophenyl)-1H-pyrrolo-[3,2-b]pyridine-2-carboxamide in solution in 18 cm³ of tetrahydrofuran. After stirring for 1 hour at a temperature in the region of 20° C., 182 mg (0.952 mmol) of 2-methoxy-5-trifluoromethylphenylamine in solution in 17 cm³ of tetrahydrofuran are added. After stirring for 16 hours at a temperature in the region of 20° C., the reaction mixture is concentrated to dryness under reduced pressure (2.7 kPa), to give a residue which is purified by flash chromatography [eluent: dichloromethane/methanol/acetonitrile] (90/5/5 by volume)]. After concentration under reduced pressure of the fractions containing the expected product, 109 mg of 3-{4-[3-(2-methoxy-5-trifluoromethylphenyl)ureido]-phenyl}-1H-pyrrolo[3,2-b]pyridine-2-carboxamide are obtained in the form of a yellow solid that melts at around 194° C.;

1H NMR (300 MHz, (CD3)2SO d6, –δ in ppm): 3.99 (s: 3H); 6.97 (broad s: 1H); from 7.18 to 7.27 (m: 2H); 7.33 (dd, J=9 and 1 Hz: 1H); 7.56 (d, J=9 Hz: 2H); 7.63 (d, J=9 Hz: 2H); 7.66 (very broad s: 1H); 7.81 (dd, J=8 and 1.5 Hz: 1H); 8.40 (dd, J=4.5 and 1.5 Hz: 1H); 8.58 (m: 2H); 9.56 (s: 1H); 11.88 (very broad s: 1H).

MS-ES+: m/z=470(+)=(M+H)(+).

The 3-(4-aminophenyl)-1H-pyrrolo[3,2-b]pyridine-2-carboxamide is prepared as described in example 2.

EXAMPLE 23

3-{4-[3-(2-Fluoro-5-trifluoromethylphenyl)-ureido]phenyl}-6-(2-methoxyethoxy)-1H-indole-2-carboxamide

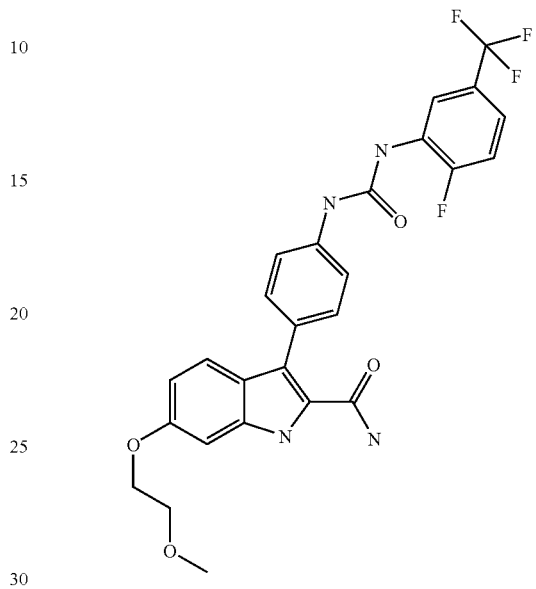

40 μl (0.28 mmol) of 2-fluoro-5-trifluoromethylphenyl isocyanate, under argon at ambient temperature, are added to a solution of 79 mg (0.24 mmol) of 3-(4-aminophenyl)-6-(2-methoxyethoxy)-1H-indole-2-carboxamide in 6 ml of tetrahydrofuran. After stirring for 22 h at ambient temperature under argon, the reaction mixture is concentrated to dryness under reduced pressure. The residue obtained is taken up in ethyl acetate and washed with water, and the organic phase is then dried over anhydrous magnesium sulfate, filtered, and concentrated to dryness under reduced pressure.

The crude product is purified by flash chromatography [eluent: methylene chloride/methanol (96/4 by volume)]. After concentration under reduced pressure of the fractions containing the expected product, 78 mg of 3-{4-[3-(2-fluoro-5-trifluoromethylphenyl)ureido]-phenyl}-6-(2-methoxyethoxy)-1H-indole-2-carboxamide are obtained in the form of a white solid.

1H NMR (400 MHz, (CD3)2SO d6, –δ in ppm): 3.32 (partially masked s, 3H); 3.69 (m, 2H); 4.09 (m, 2H); 6.31 (broad m, 1H); 6.72 (dd, J=2.5 and 9.0 Hz, 1H); 6.91 (d, J=2.5 Hz, 1H); 7.28 (d, J=9.0 Hz, 1H); from 7.32 to 7.45 (broad m, 1H); 7.39 (m, 1H); 7.42 (broad d, J=8.5 Hz, 2H); 7.51 (dd, J=9.0 and 11.0 Hz, 1H); 7.59 (broad d, J=8.5 Hz, 2H); 8.64 (dd, J=2.0 and 7.5 Hz, 1H); 8.98 (broad s, 1H); 9.34 (broad s, 1H); 11.4 (s, 1H).

ES: m/z=531 (MH+), m/z=514 (MH+–NH3) base peak.

The 3-(4-aminophenyl)-6-(2-methoxyethoxy)-1H-indole-2-carboxamide can be prepared in the following way:

8 ml of 7N aqueous ammonia in methanol and 4 ml of 28% aqueous ammonia in water are added to 80 mg (0.24 mmol) of methyl 3-(4-aminophenyl)-6-(2-methoxyethoxy)-1H-indole-2-carboxylate and the reaction medium is heated at 100° C. for 16 h in a hermetically closed glass tube. 2 ml of 28% aqueous ammonia in water are then added and the reaction is heated at 100° C. for 24 h. The reaction medium is evaporated to dryness under reduced pressure. The crude is purified by flash chromatography [eluent: methylene chloride/methanol (98/2 then 95/5 by volume)]. After concentration under reduced pressure of the fractions containing the expected product, 40 mg of 3-(4-aminophenyl)-6-(2-methoxyethoxy)-1H-indole-2-carboxamide are obtained in the form of a brown solid.

EI: m/z=325 (M$^+$) base peak, m/z=308 (M–NH$_3$)$^+$, m/z=249 (m/z=308–C$_3$H$_7$O)$^+$, m/z=221 (m/z=249–CO)$^+$, m/z=59 (C$_3$H$_7$O$^+$).

The methyl 3-(4-aminophenyl)-6-(2-methoxyethoxy)-1H-indole-2-carboxylate can be prepared in the following way:

0.321 ml (2.29 mmol) of triethylamine is added, at ambient temperature, to 396 mg (2.29 mmol) of (4-aminophenyl) boronic acid hydrochloride in a methanol/toluene mixture (30 ml/25 ml). The mixture is stirred at ambient temperature for 15 minutes and then 300 mg (0.91 mmol) of methyl 3-bromo-6-(2-methoxyethoxy)-1H-indole-2-carboxylate are added at ambient temperature, followed by a solution of 242 mg (2.28 mmol) of sodium carbonate in 5 ml of water. 108 mg (2.55 mmol) of lithium chloride is added at ambient temperature under argon, followed by 74 mg (0.06 mmol) of palladium tetrakis(triphenylphosphine). The reaction is refluxed for 4 h 30 min under argon and is heated at ambient temperature for 16 h. The reaction mixture is concentrated to dryness under reduced pressure. The residue obtained is taken up in ethyl acetate and washed with water, and the organic phase is then dried over anhydrous magnesium sulfate, filtered, and concentrated to dryness under reduced pressure. The crude product is purified by flash chromatography [eluent: methylene chloride/methanol (99/1 by volume)]. After concentration under reduced pressure of the fractions containing the expected product, 219 mg of methyl 3-(4-aminophenyl)-6-(2-methoxyethoxy)-1H-indole-2-carboxylate are obtained in the form of a pale yellow solid.

EI: m/z=340 (M$^+$) base peak, m/z=308 (M–CH$_3$OH)$^+$, m/z=281 (M–C$_2$H$_3$O$_2$)$^+$, m/z=221 (m/z=281–C$_3$H$_8$O)$^+$, m/z=59 (C$_3$H$_7$O$^+$).

The methyl 3-bromo-6-(2-methoxyethoxy)-1H-indole-2-carboxylate can be prepared in the following way:

A solution of 104 mg (0.42 mmol) of methyl 6-(2-methoxyethoxy)-1H-indole-2-carboxylate in 3 ml of dimethylformamide is cooled to –40° C. in an acetone/solid carbon dioxide bath and then a solution of 74 mg (0.41 mmol) of N-bromosuccinimide in 1 ml of dimethylformamide is added at –40° C. The solution is stirred at between –45° C. and –30° C. for 30 minutes and then a solution of 30 mg (0.17 mmol) of N-bromosuccinimide in 1 ml of dimethylformamide is added at –40° C. The solution is stirred at between –45° C. and –30° C. for 1 h.

The solution is diluted with ethyl acetate, the temperature is brought back up to ambient temperature, and the organic phase is then washed with water, dried over anhydrous magnesium sulfate, filtered, and concentrated to dryness under reduced pressure. The crude product is purified by flash chromatography [eluent: ethyl acetate/cyclohexane (½ by volume)]. After concentration under reduced pressure of the fractions containing the expected product, 92 mg of methyl 3-bromo-6-(2-methoxyethoxy)-1H-indole-2-carboxylate are obtained in the form of a white solid.

EI: m/z=327 (M$^+$), m/z=269 (M–C$_2$H$_2$O$_2$)$^+$, m/z=237 (m/z=269–CH$_3$OH)$^+$, m/z=59 (C$_3$H$_7$O$^+$), m/z=45 (C$_2$H$_5$O$^+$) base peak.

The methyl 6-(2-methoxyethoxy)-1H-indole-2-carboxylate can be prepared in the following way:

4.915 ml (52.30 mmol) of 2-bromoethyl methyl ether are added to a suspension of 2 g (10.46 mmol) of methyl 6-hydroxy-1H-indole-2-carboxylate, 8.68 g (52.30 mmol) of potassium iodide and 7.23 g (52.30 mmol) of potassium carbonate in 150 ml of acetone at ambient temperature. The reaction medium is refluxed for 22 h. The reaction is brought back to ambient temperature and ethyl acetate is then added. The organic phase is washed with water and then dried over anhydrous magnesium sulfate, filtered, and concentrated to dryness under reduced pressure. The crude product is purified by flash chromatography [eluent:acetone/cyclohexane (⅙ by volume)]. After concentration under reduced pressure of the fractions containing the expected product, 630 mg of methyl 6-(2-methoxyethoxy)-1H-indole-2-carboxylate are obtained in the form of a yellow solid.

EI: m/z=249 (M$^+$) base peak, m/z=191 (M–C$_2$H$_2$O$_2$)$^+$, m/z=159 (m/z=191–CH$_3$OH)$^+$.

The methyl 6-hydroxy-1H-indole-2-carboxylate can be prepared in the following way:

0.144 ml (2.70 mmol) of concentrated sulfuric acid is added, at ambient temperature, to a solution of 5.98 g (33.75 mmol) of 6-hydroxy-1H-indole-2-carboxylic acid in 350 ml of methanol. The mixture is refluxed for 9 days and the reaction mixture is then concentrated to dryness under reduced pressure. The residue obtained is taken up in water and alkalinized to pH9 with a 38% potassium hydroxide solution, and the product is then extracted 6 times with ethyl acetate. The organic phases are combined and then dried over anhydrous magnesium sulfate, filtered, and concentrated to dryness under reduced pressure, to give 5.81 g of methyl 6-hydroxy-1H-indole-2-carboxylate in the form of a brown solid.

EI: m/z=191 (M$^+$) base peak, m/z=159 (M–CH$_3$OH)$^+$, m/z=131 (m/z=159–CO)$^+$.

The 6-hydroxy-1H-indole-2-carboxylic acid can be prepared in the following way:

146 ml (146 mmol) of 1M boron tribromide in methylene chloride are added slowly, at 0° C., to a solution of 10 g (48.73 mmol) of methyl 6-methoxy-2-indole carboxylate in 500 ml of methylene chloride. The reaction medium is stirred at 0° C. for 1 h and at ambient temperature for 2 h. The reaction medium is cooled to 0° C. and 100 ml (100 mmol) of 1M boron tribromide in methylene chloride are added slowly, at 0° C. The reaction is stirred at 0° C. for 1 h and at ambient temperature for 16 h. The reaction medium is then cooled to approximately 0° C. and a 1N hydrochloric acid solution (247 ml) is added slowly with stirring. The mixture obtained is filtered over sintered glass. The organic phase (methylene chloride) of the filtrate is separated and the aqueous phase is then acidified with 5N hydrochloric acid and extracted with ethyl acetate. The organic phase (ethyl acetate) is dried over anhydrous magnesium sulfate, filtered, and concentrated to dryness under reduced pressure, to give 6.39 g of 6-hydroxy-1H-indole-2-carboxylic acid in the form of a brown solid.

ES: m/z=176 (M–H)$^-$ base peak

EXAMPLE 24

3-{4-[3-(2-Fluoro-5-trifluoromethylphenyl)-ureido]phenyl}-6-(2-pyrrolidin-1-ylethoxy)-1H-indole-2-carboxamide

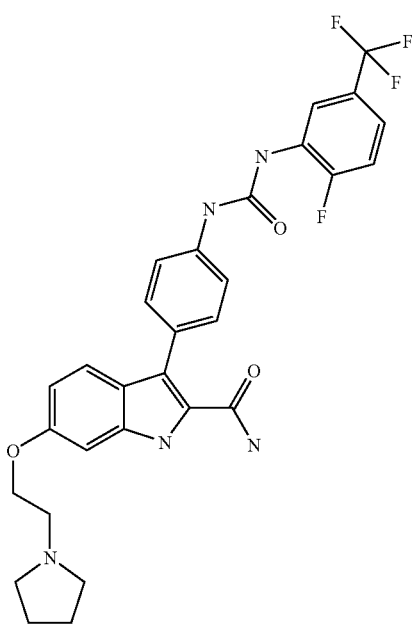

17 µl (0.12 mmol) of 2-fluoro-5-trifluoromethylphenyl isocyanate, under argon at ambient temperature, are added to a solution of 45 mg (0.12 mmol) of 3-(4-aminophenyl)-6-(2-pyrrolidin-1-ylethoxy)-1H-indole-2-carboxamide in 6 ml of tetrahydrofuran. After stirring at ambient temperature for 22 h under argon, the reaction mixture is taken up in ethyl acetate and washed with water, and the organic phase is then dried over anhydrous magnesium sulfate, filtered, and concentrated to dryness under reduced pressure. The crude product is purified by flash chromatography [eluent: methylene chloride/methanol (70/30 by volume)]. After concentration under reduced pressure of the fractions containing the expected product, 32 mg of 3-{4-[3-(2-fluoro-5-trifluoromethylphenyl)ureido]phenyl}-6-(2-pyrrolidin-1-ylethoxy)-1H-indole-2-carboxamide, are obtained in the form of a brown solid.

1H NMR (400 MHz, (CD3)2SO d6, –δ in ppm): 1.69 (m, 4H); 2.54 (m, 4H); 2.81 (t, J=6.0 Hz, 2H); 4.08 (t, J=6.0 Hz, 2H); 6.30 (broad m, 1H); 6.72 (dd, J=2.5 and 9.0 Hz, 1H); 6.91 (d, J=2.5 Hz, 1H); 7.27 (d, J=9.0 Hz, 1H); from 7.32 to 7.48 (broad m, 1H); 7.39 (m, 1H); 7.42 (broad d, J=8.5 Hz, 2H); 7.51 (dd, J=9.0 and 11.0 Hz, 1H); 7.60 (broad d, J=8.5 Hz, 2H); 8.65 (dd, J=2.5 and 7.5 Hz, 1H); 8.99 (d, J=2.5 Hz, 1H); 9.36 (s, 1H); 11.4 (s, 1H).

ES: m/z=570 (MH$^+$) base peak

The 3-(4-aminophenyl)-6-(2-pyrrolidin-1-ylethoxy)-1H-indole-2-carboxamide can be prepared in the following way:

8 ml of 7N aqueous ammonia in methanol and 4 ml of 28% aqueous ammonia in water are added to 133 mg (0.35 mmol) of methyl 3-(4-aminophenyl)-6-(2-pyrrolidin-1-ylethoxy)-1H-indole-2-carboxylate and the reaction medium is heated at 100° C. for 16 h in a hermetically closed glass tube. 2 ml of 28% aqueous ammonia in water are then added and the reaction is heated at 100° C. for 24 h. The reaction medium is evaporated to dryness under reduced pressure. The crude product is purified by flash chromatography [eluent: ethyl acetate/methanol (70/30 by volume)]. After concentration under reduced pressure of the fractions containing the expected product, 25 mg of 3-(4-aminophenyl)-6-(2-pyrrolidin-1-ylethoxy)-1H-indole-2-carboxamide are obtained in the form of a pale yellow solid.

ES: m/z=365 (MH$^+$) base peak

The methyl 3-(4-aminophenyl)-6-(2-pyrrolidin-1-ylethoxy)-1H-indole-2-carboxylate can be prepared in the following way:

0.223 ml (1.59 mmol) of triethylamine is added, at ambient temperature, to 275 mg (1.59 mmol) of (4-aminophenyl)boronic acid hydrochloride in a methanol/toluene mixture (30 ml/25 ml). The mixture is stirred at ambient temperature for 15 minutes and then 222 mg (0.60 mmol) of methyl 3-bromo-6-(2-pyrrolidin-1-ylethoxy)-1H-indole-2-carboxylate are added at ambient temperature, followed by a solution of 168 mg (1.58 mmol) of sodium carbonate in 5 ml of water. 75 mg (1.77 mmol) of lithium chloride are added at ambient temperature, under argon, followed by 51 mg (0.04 mmol) of palladium tetrakis(triphenylphosphine). The reaction is refluxed for 5 h under argon and is then heated at ambient temperature for 16 h. The reaction mixture is concentrated to dryness under reduced pressure. The residue obtained is taken up in ethyl acetate and washed with water, and the organic phase is then dried over anhydrous magnesium sulfate, filtered, and concentrated to dryness under reduced pressure. The crude product is purified by flash chromatography [eluent: methylene chloride/methanol (98/2 by volume)]. After concentration under reduced pressure of the fractions containing the expected product, 252 mg of methyl 3-(4-aminophenyl)-6-(2-pyrrolidin-1-ylethoxy)-1H-indole-2-carboxylate are obtained in the form of an orange solid.

EI: m/z=379 (M$^+$), m/z=84 (C$_5$H$_{10}$N$^+$) base peak

The methyl 3-bromo-6-(2-pyrrolidin-1-ylethoxy)-1H-indole-2-carboxylate can be prepared in the following way:

A solution of 495 mg (1.72 mmol) of methyl 6-(2-pyrrolidin-1-ylethoxy)-1H-indole-2-carboxylate in 11 ml of dimethylformamide is cooled to –40° C. in an acetone/solid carbon dioxide bath and then a solution of 306 mg (1.72 mmol) of N-bromosuccinimide in 6 ml of dimethylformamide is added dropwise at –40° C. The solution is stirred at –40° C. and brought back to ambient temperature slowly over 5 h. The residue obtained is taken up in ethyl acetate, and then washed with water, dried over anhydrous magnesium sulfate, filtered, and concentrated to dryness under reduced pressure. The crude product is purified by flash chromatography [eluent: methylene chloride/methanol (90/10 by volume)]. After concentration under reduced pressure of the fractions containing the expected product, 263 mg of 3-bromo-6-(2-pyrrolidin-1-ylethoxy)-1H-indole-2-carboxylate are obtained in the form of a gray solid.

ES: m/z=367 (MH$^+$) base peak

The methyl 6-(2-pyrrolidin-1-ylethoxy)-1H-indole-2-carboxylate can be prepared in the following way:

Under a stream of argon, 2.20 g (8.37 mmol) of triphenylphosphine are added, at ambient temperature, to a solution of 800 mg (4.18 mmol) of methyl 6-hydroxy-1H-indole-2-carboxylate in 60 ml of tetrahydrofuran. 0.979 ml (8.37 mmol) of 1-(2-hydroxyethyl)pyrrolidine is then added, at ambient temperature, to the reaction medium. The reaction is then cooled to approximately 5° C. in a water/ice bath and a solution of 1.46 g (8.37 mmol) of diethylazodicarboxylate in 5 ml of tetrahydrofuran is added dropwise to the reaction medium, the temperature being maintained at between 5 and 10° C. during the addition. The reaction is then stirred at 5° C. for 15 minutes and then at ambient temperature for 40 h. Ethyl acetate is added to the reaction medium. The organic phase is washed with water and then dried over anhydrous magnesium sulfate, filtered, and concentrated to dryness under reduced pressure. The crude product is purified by flash chromatography [eluent: methylene chloride/methanol (90/10 by volume)]. After concentration under reduced pressure of the fractions containing the expected product, 880 mg of methyl 6-(2-pyrrolidin-1-ylethoxy)-1H-indole-2-carboxylate are obtained in the form of a brown solid.

EI: m/z=288 (M$^+$), m/z=84 ($C_5H_{10}ON^+$) base peak.

The methyl 6-hydroxy-1H-indole-2-carboxylate is prepared as described in example 23.

EXAMPLE 25

3-{6-[3-(2-fluoro-5-trifluoromethylphenyl)-ureido]-pyridin-3-yl)-6-methoxy-1H-indole-2-carboxamide

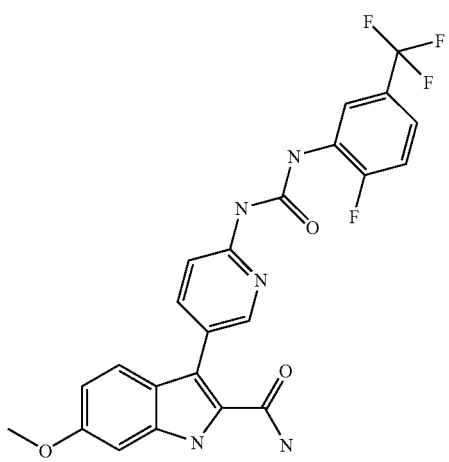

A suspension of 100 mg (0.37 mmol) of 3-bromo-6-methoxy-1H-indole-2-carboxamide and 43 mg (0.04 mmol) of tetrakis(triphenylphosphine)palladium (0) in 5 ml of dioxane is stirred at ambient temperature for 10 minutes. 190 mg (0.45 mmol) of 1-(2-fluoro-5-trifluoromethylphenyl)-3-[5-(4,4,5, 5-tetramethyl-1,3,2-dioxaborolan-2-yl) yridine-2-yl]urea and 6 ml of dioxane are then added at ambient temperature, followed by a solution of 86 mg (1.48 mmol) of potassium fluoride in 1 ml of water. The mixture is refluxed for 16 h 45 min. The reaction medium is evaporated to dryness under reduced pressure. The crude is purified by flash chromatography [eluent: methylene chloride/methanol (99/1 then 98/2 then 97/3 then 94/4 by volume)]. After concentration under reduced pressure of the fractions containing the expected product, 60 mg of 3-{6-[3-(2-fluoro-5-trifluoromethylphenyl)ureido]yridine-3-yl}-6-methoxy-1H-indole-2-carboxamide are obtained in the form of a yellow solid.

1H NMR (300 MHz, (CD3)2SO d6, -δ in ppm): 3.81 (s, 3H); 6.75 (dd, J=2.0 and 8.5 Hz, 1H); 6.93 (d, J=2.0 Hz, 1H); 7.00 (broad m, 1H); 7.35 (d, J=8.5 Hz, 1H); from 7.39 to 7.59 (m, 4H); 7.89 (dd, J=2.0 and 8.5 Hz, 1H); 8.35 (d, J=2.0 Hz, 1H); 8.70 (broad d, J=7.5 Hz, 1H); 10.05 (broad s, 1H); 11.3 (very broad m, 1H); 11.5 (broad s, 1H).

ES: m/z=488 (MH$^+$) base peak.

The 3-bromo-6-methoxy-1H-indole-2-carboxamide can be prepared in the following way:

A solution of 540 mg (2.84 mmol) of 6-methoxy-1H-indole-2-carboxamide in 8 ml of pyridine is cooled to 0° C. and a solution of 908 mg (2.84 mmol) of pyridinium tribromide in 6 ml of pyridine is added thereto, dropwise. The reaction medium is stirred at 0° C. for 30 minutes and at ambient temperature for 19 h. 20 ml of ice-cold water is added to the reaction medium. The latter is then stirred at ambient temperature for 1 h and then filtered over sintered glass, to give 538 mg of 3-bromo-6-methoxy-1H-indole-2-carboxamide in the form of a white solid.

ES: m/z=269 (MH$^+$) base peak.

The 6-methoxy-1H-indole-2-carboxamide can be prepared in the following way:

A suspension of 4 g (19.49 mmol) of methyl 6-methoxy-2-indolecarboxylate in 60 ml of 28% aqueous ammonia is heated at 50° C. for 14 h in an autoclave. After filtration of the mixture over sintered glass, the white solid obtained is washed with water and dried, and is then added to a hot mixture of ethyl acetate/cyclohexane (100 ml/10 ml). The medium is cooled in a water/ice bath and filtered over sintered glass, to give 1.05 g of 6-methoxy-1H-indole-2-carboxamide in the form of a white solid.

EI: m/z=190 (M$^+$) base peak, m/z=173 (M–NH$_3$)$^+$, m/z=145 (M–CH$_3$NO)$^+$

The 1-(2-fluoro-5-trifluoromethylphenyl)-3-[5-(4,4,5,5-tetramethyl-1,3,2-dioxaborolan-2-yl) yridine-2-yl]urea can be prepared in the following way:

A suspension of 505 mg (1.80 mmol) of tricyclohexylphosphine and 276 mg (0.48 mmol) of bis(dibenzylideneacetone) palladium in 20 ml of dioxane is stirred at ambient temperature under argon for 10 minutes. 4.54 g (12.01 mmol) of 1-(5-bromopyridin-2-yl)-3-(2-fluoro-5-trifluoromethylphenyl)urea are added to the reaction medium, followed by 80 ml of dioxane, 4.12 g (16.20 mmol) of bis(pinacolato)diborane and 1.77 g (18.04 mmol) of potassium acetate. The reaction is refluxed under argon for 16 h and 300 ml of water are then added at ambient temperature. The mixture is stirred at ambient temperature for 10 minutes and then filtered over sintered glass, and the solid obtained is washed with a small amount of water. The solid obtained is taken up in 350 ml of boiling ethyl acetate and, after filtration under hot conditions, the filtrate is evaporated to dryness under reduced pressure. 3.05 g of 1-(2-fluoro-5-trifluoromethylphenyl)-3-[5-(4,4,5,5-tetramethyl-1,3,2-dioxaborolan-2-yl) yridine-2-yl]urea are obtained in the form of a pale yellow solid.

ES: m/z=426 (MH$^+$) base peak.

The 1-(5-bromopyridin-2-yl)-3-(2-fluoro-5-trifluoromethylphenyl)urea can be prepared in the following way: 3.27 ml (23.44 mmol) of triethylamine are added, at 0° C., to a solution of 4.06 g (23.47 mmol) of 2-amino-5-bromopyridine in 200 ml of anhydrous tetrahydrofuran. 3.39 ml (23.44 mmol) of 2-fluoro-5-trifluoromethyl phenylisocyanate are then added, at 0° C., dropwise. The reaction is stirred at ambient temperature for 64 h. 400 ml of ethyl acetate are added to the reaction medium. The organic phase is then washed with water and then with a saturated aqueous sodium chloride solution, and is then finally filtered over sintered glass. 4.55 g of 1-(5-bromopyridin-2-yl)-3-(2-fluoro-5-trifluoromethylphenyl)urea are obtained in the form of a white solid.

EI: m/z=377 (M$^+$), m/z=179 ($C_7H_5NF_4^+$), m/z=172 ($C_5H_5N_2Br^+$) base peak.

EXAMPLE 26

3-{4-[3-(2-Fluoro-5-trifluoromethylphenyl)-ureido]phenyl}-6-methoxy-1H-indole-2-carboxamide

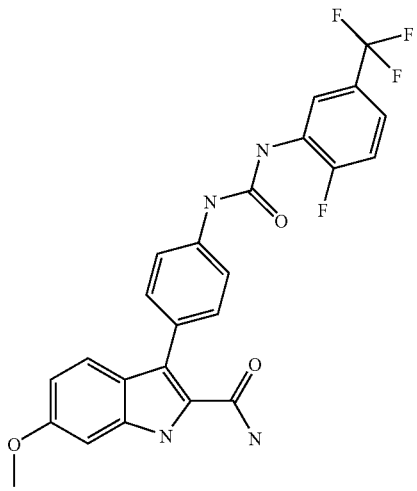

A suspension of 2.54 g (9.44 mmol) of 3-bromo-6-methoxy-1H-indole-2-carboxamide and 1.09 g (0.94 mmol) of tetrakis(triphenylphosphine)palladium (0) in 125 ml of dioxane is stirred at ambient temperature for 10 minutes. 4.81 g (11.33 mmol) of 1-(2-fluoro-5-trifluoromethylphenyl)-3-[4-(4,4,5,5-tetramethyl-1,3,2-dioxaborolan-2-yl)phenyl]urea and 150 ml of dioxane are then added, at ambient temperature, followed by a solution of 2.19 g (37.77 mmol) of potassium fluoride in 25 ml of water. The mixture is refluxed for 18 h. The reaction medium is evaporated to dryness under reduced pressure. The residue obtained is taken up in ethyl acetate and washed with water, and the organic phase is then dried over anhydrous magnesium sulfate, filtered, and concentrated to dryness under reduced pressure. The crude is purified by flash chromatography [eluent: methylene chloride/methanol (98/2 by volume)]. After concentration under reduced pressure of the fractions containing the expected product, 1.73 g of 3-{4-[3-(2-fluoro-5-trifluoromethylphenyl)ureido]-phenyl}-6-methoxy-1H-indole-2-carboxamide, are obtained in the form of a brown solid.

1H NMR (400 MHz, (CD3)2SO d6, −δ in ppm): 3.78 (s, 3H); 6.30 (broad m, 1H); 6.71 (dd, J=2.5 and 9.0 Hz, 1H); 6.91 (d, J=2.5 Hz, 1H); 7.28 (d, J=9.0 Hz, 1H); from 7.32 to 7.45 (broad m, 1H); 7.39 (m, 1H); 7.42 (broad d, J=8.5 Hz, 2H); 7.51 (dd, J=9.0 and 11.0 Hz, 1H); 7.60 (broad d, J=8.5 Hz, 2H); 8.64 (dd, J=2.0 and 7.5 Hz, 1H); 8.99 (broad s, 1H); 9.37 (broad s, 1H); 11.4 (broad s, 1H).

ES: m/z=487 (MH$^+$), m/z=470 (MH$^+$−NH$_3$) base peak.

The 1-(2-fluoro-5-trifluoromethylphenyl)-3-[4-(4,4,5,5-tetramethyl-1,3,2-dioxaborolan-2-yl)phenyl]urea can be prepared according to the procedure described in US patent 2005043347 A1.

The 3-bromo-6-methoxy-1H-indole-2-carboxamide can be prepared as described in example 25.

EXAMPLE 27

3-{4-[3-(2-Fluoro-5-trifluoromethylphenyl)-ureido]phenyl}-6-hydroxy-1H-indole-2-carboxamide

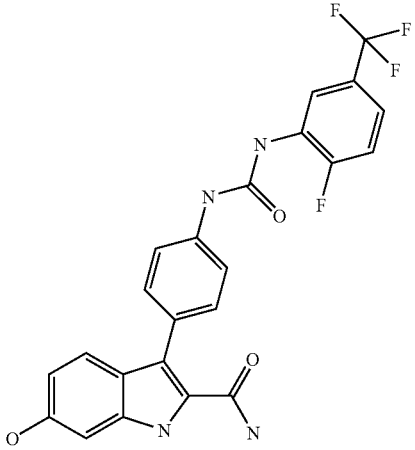

A suspension of 1.11 g (2.28 mmol) of 3-{4-[3-(2-fluoro-5-trifluoromethyl-phenyl)ureido]phenyl}-6-methoxy-1H-indole-2-carboxamide in 100 ml of methylene chloride is cooled to −5° C. in an acetone/solid carbon dioxide bath and then 12.34 ml (12.34 mmol) of a 1M solution of boron tribromide in methylene chloride is added dropwise at −5° C. The reaction is stirred for 2 h at approximately 0° C. and then at ambient temperature for 26 h. The reaction medium is then cooled to approximately 0° C. in a water/ice bath and 30 ml of 1N hydrochloric acid are added dropwise, followed by 50 ml of methylene chloride and 30 ml of water. The mixture is stirred at approximately 0° C. for 15 minutes and then at ambient temperature for 30 minutes. The reaction medium is then filtered over sintered glass, to give a brown solid. The latter is purified by flash chromatography [eluent: methylene chloride/methanol (95/5 by volume)]. After concentration under reduced pressure of the fractions containing the expected product, 840 mg of 3-{4-[3-(2-fluoro-5-trifluoromethylphenyl)ureido]phenyl}-6-hydroxy-1H-indole-2-carboxamide are obtained in the form of a brown solid.

1H NMR (400 MHz, (CD3)2SO d6, −δ in ppm): 6.21 (broad m, 1H); 6.58 (dd, J=2.0 and 8.5 Hz, 1H); 6.80 (d, J=2.0 Hz, 1H); 7.18 (d, J=8.5 Hz, 1H); 7.30 (broad m, 1H); 7.40 (m, 3H); 7.51 (dd, J=9.0 and 11.0 Hz, 1H); 7.58 (broad d, J=8.5 Hz, 2H); 8.65 (dd, J=2.0 and 7.5 Hz, 1H); 8.92 (d, J=3.0 Hz, 1H); 9.23 (s, 1H); 9.29 (s, 1H); 11.2 (s, 1H).

ES: m/z=471 (M−H)$^-$ base peak.

The 3-{4-[3-(2-fluoro-5-trifluoromethylphenyl)ureido]-phenyl}-6-methoxy-1H-indole-2-carboxamide can be prepared as described in example 26.

EXAMPLE 28

3-{4-[3-(2-Fluoro-5-trifluoromethylphenyl)-ureido]
phenyl}-6-(2-hydroxyethoxy)-1H-indole-2-carboxamide

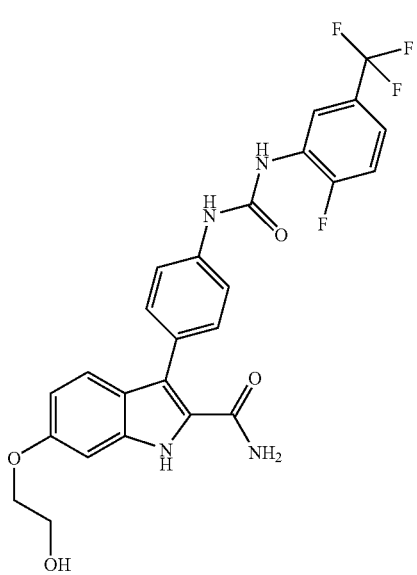

1.23 g (8.90 mmol) of potassium carbonate are added, at ambient temperature, to a solution of 280 mg (0.59 mmol) of 3-{4-[3-(2-fluoro-5-trifluoromethylphenyl)ureido]phenyl}-6-hydroxy-1H-indole-2-carboxamide in 10 ml of dimethylformamide. 0.69 ml (8.89 mmol) of iodoethanol is then added at ambient temperature. The reaction medium is heated at 110° C. for 2 h 30 min. The medium is taken up in ethyl acetate and washed with water, and the organic phase is then dried over anhydrous magnesium sulfate, filtered, and concentrated to dryness under reduced pressure.

The crude product is purified by preparative LC/MS. After evaporation of the solvents to dryness under reduced pressure, the residue obtained is triturated with ethyl acetate and diisopropyl ether and, after filtration, 48 mg of 3-{4-[3-(2-fluoro-5-trifluoromethylphenyl)ureido]phenyl}-6-(2-hydroxyethoxy)-1H-indole-2-carboxamide are obtained in the form of a gray solid.

1H NMR (400 MHz, (CD3)2SO d6, –δ in ppm): 3.75 (q, J=5.5 Hz, 2H); 4.00 (t, J=5.5 Hz, 2H); 4.86 (t, J=5.5 Hz, 1H); 6.30 (broad m, 1H); 6.73 (dd, J=2.0 and 9.0 Hz, 1H); 6.91 (d, J=2.0 Hz, 1H); 7.28 (d, J=9.0 Hz, 1H); from 7.32 to 7.47 (broad m, 1H); 7.39 (m, 1H); 7.42 (broad d, J=8.5 Hz, 2H); 7.51 (dd, J=9.0 and 11.0 Hz, 1H); 7.59 (broad d, J=8.5 Hz, 2H); 8.65 (dd, J=2.5 and 7.5 Hz, 1H); 8.97 (broad s, 1H); 9.33 (broad s, 1H); 11.4 (s, 1H).

ES: m/z=517(MH$^+$) base peak, m/z=500 (MH$^+$–NH$_3$).

The 3-{4-[3-(2-fluoro-5-trifluoromethylphenyl)ureido]-phenyl}-6-hydroxy-1H-indole-2-carboxamide can be prepared as described in example 27.

EXAMPLE 29

3-{4-[3-(2-Fluoro-5-trifluoromethylphenyl)-ureido]
phenyl}-7-nitro-1H-indole-2-carboxamide

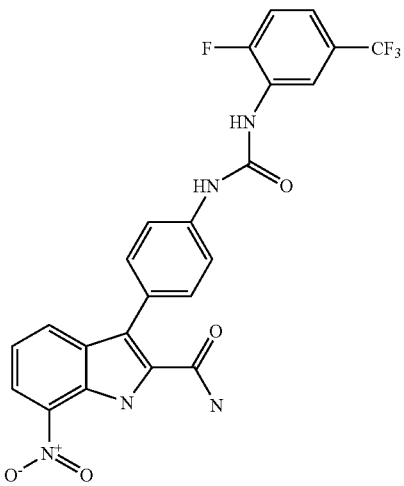

A suspension of 2.70 g (9.5 mmol) of 3-bromo-7-nitro-1H-indole-2-carboxamide and 1.10 g (0.95 mmol) of tetrakis (triphenylphosphine)palladium (0) in 135 ml of dioxane is stirred at ambient temperature for 10 minutes. 4.84 g (11.41 mmol) of 1-(2-fluoro-5-trifluoromethylphenyl)-3-[4-(4,4,5,5-tetramethyl-1,3,2-dioxaborolan-2-yl)phenyl]urea and 165 ml of dioxane are then added at ambient temperature, followed by a solution of 2.215 g (38.13 mmol) of potassium fluoride in 27 ml of water. The mixture is refluxed for 18 h. A spatula of carbon black is then added to the reaction medium at approximately 50° C. and the latter is then stirred at 50° C. for 10 minutes. The reaction medium is filtered over yridi and then washed with ethyl acetate. The filtrate is evaporated to dryness under reduced pressure. The residue obtained is taken up in ethyl acetate and washed with water, and the organic phase is then dried over anhydrous magnesium sulfate, filtered, and concentrated to dryness under reduced pressure. The crude is purified by flash chromatography [eluent: methylene chloride/methanol (99/1 then 98/2 by volume)]. After concentration under reduced pressure of the fractions containing the expected product, 3.44 g of 3-{4-[3-(2-fluoro-5-trifluoromethylphenyl)ureido]-phenyl}-7-nitro-1H-indole-2-carboxamide are obtained in the form of a yellow solid.

1H NMR (300 MHz, (CD3)2SO d6, –δ in ppm): 7.33 (t, J=7.5 Hz, 1H); 7.40 (m, 1H); 7.45 (broad d, J=8.5 Hz, 2H); 7.51 (dd, J=9.0 and 11.0 Hz, 1H); 7.59 (broad d, J=8.5 Hz, 2H); 7.69 (broad m, 2H); 7.96 (d, J=7.5 Hz, 1H); 8.27 (d, J=7.5 Hz, 1H); 8.65 (dd, J=2.5 and 7.5 Hz, 1H); 8.95 (broad d, J=2.5 Hz, 1H); 9.32 (s, 1H); 11.55 (s, 1H).

ES: m/z=500 (M–H)$^-$ base peak.

The 3-bromo-7-nitro-1H-indole-2-carboxamide can be prepared in the following way:

A suspension of 2.57 g (12.53 mmol) of 7-nitro-1H-indole-2-carboxamide in 35 ml of pyridine is cooled to 0° C. in a water/ice bath. A solution of 4.01 g (12.53 mmol) of pyridinium tribromide in 20 ml of pyridine is then added at 0° C. dropwise, and the reaction is then stirred at 0° C. for 30 minutes and at ambient temperature for 16 h. 70 ml of ice-cold water are then added to the reaction medium. The latter is then stirred at ambient temperature for 15 minutes and is then filtered over sintered glass, to give 2.81 g of 3-bromo-7-nitro-1H-indole-2-carboxamide in the form of a brown solid.

EI: m/z=283 (M+) base peak, m/z=266 (M−NH3)+, m/z=220 (m/z=266−NO2)+, m/z=141 (m/z=220−Br)+.

The 7-nitro-1H-indole-2-carboxamide can be prepared in the following way:

A suspension of 133 mg (0.57 mmol) of ethyl 7-nitroindole-2-carboxylate in 3.84 ml of 28% aqueous ammonia is heated at 50° C. for 18 h in a stoppered glass tube. The reaction medium is filtered over sintered glass. The yellow solid obtained is washed with water and with cyclohexane and then dried under vacuum. 70 mg of 7-nitro-1H-indole-2-carboxamide are obtained in the form of a yellow solid.

ES: m/z=206 (MH+) base peak.

EXAMPLE 30

7-Amino-3-{4-[3-(2-fluoro-5-trifluoromethylphenyl) ureido]phenyl}-1H-indole-2-carboxamide

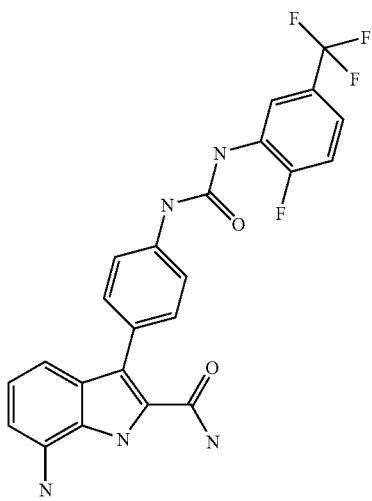

3.28 g of palladium-on-charcoal are added to a suspension of 3.42 g (6.82 mmol) of 3-{4-[3-(2-fluoro-5-trifluoromethylphenyl)ureido]phenyl}-7-nitro-1H-indole-2-carboxamide in 480 ml of methanol. The reaction mixture is hydrogenated at 30° C. under 3 bar for 2 h in an autoclave, and is then filtered over yridi. The filtrate is evaporated to dryness under reduced pressure. The residue obtained is triturated with ethyl acetate and a small amount of methylene chloride and then filtered. 1.30 g of 7-amino-3-{4-[3-(2-fluoro-5-trifluoromethylphenyl)ureido]phenyl}-1H-indole-2-carboxamide are obtained in the form of a gray solid.

1H NMR(400 MHz, (CD3)2SO d6, −δ in ppm): 5.40 (broad s, 2H); 6.17 (broad m, 1H); 6.41 (d, J=7.5 Hz, 1H); 6.62 (d, J=7.5 Hz, 1H); 6.78 (t, J=7.5 Hz, 1H); 7.39 (m, 1H); 7.41 (broad d, J=8.5 Hz, 2H); 7.47 (broad m, 1H); 7.51 (dd, J=9.0 and 11.0 Hz, 1H); 7.61 (broad d, J=8.5 Hz, 2H); 8.65 (dd, J=2.0 and 7.5 Hz, 1H); 8.99 (broad m, 1H); 9.33 (broad m, 1H); 11.25 (broad s, 1H).

ES: m/z=472 (MH+) base peak, m/z=455 (MH+−NH3).

The 3-{4-[3-(2-fluoro-5-trifluoromethylphenyl)ureido]phenyl}-7-nitro-1H-indole-2-carboxamide can be prepared as described in example 29.

EXAMPLE 31

3-{4-[3-(2-Fluoro-5-trifluoromethylphenyl)-ureido] phenyl}-7-(2-hydroxyethylamino)-1H-indole-2-carboxamide

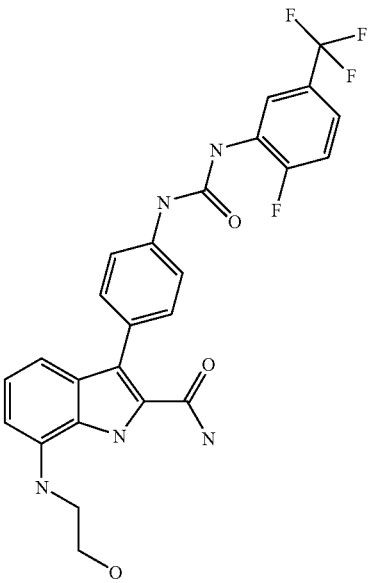

A suspension of 160 mg (0.34 mmol) of 7-amino-3-{4-[3-(2-fluoro-5-trifluoromethylphenyl)ureido]phenyl}-1H-indole-2-carboxamide and 20 mg (0.34 mmol) of 2-hydroxyacetaldehyde in 16 ml of methanol and 19.43 µl (0.34 mmol) of acetic acid is heated at 50° C. for 3 h and then 64 mg (1.02 mmol) of sodium cyanoborohydride are added at ambient temperature and the reaction is stirred at this temperature for 16 h. The reaction is evaporated to dryness under reduced pressure. The residue obtained is taken up with ethyl acetate and water and then alkalinized to pH 10 with 30% sodium hydroxide. The organic phase is separated, dried over anhydrous magnesium sulfate, filtered, and concentrated to dryness under reduced pressure. The crude product is purified by flash chromatography [eluent: methylene chloride/methanol (94/6 by volume)]. The brown solid obtained is triturated with ethyl acetate and a small amount of ether and, after filtration, 14 mg of 3-{4-[3-(2-fluoro-5-trifluoromethylphenyl)ureido] phenyl}-7-(2-hydroxyethylamino)-1H-indole-2-carboxamide are obtained in the form of a brown solid.

1H NMR (400 MHz, (CD3)2SO d6, −δ in ppm): 3.25 (partially masked m, 2H); 3.67 (q, J=6.0 Hz, 2H); 4.72 (t, J=6.0 Hz, 1H); 5.95 (t, J 6.0 Hz, 1H); 6.17 (broad m, 1H); 6.32 (d, J=7.5 Hz, 1H); 6.64 (d, J=7.5 Hz, 1H); 6.86 (t, J=7.5 Hz, 1H); from 7.35 to 7.48 (m, 4H); 7.51 (m, 1H); 7.60 (broad d, J=8.5 Hz, 2H); 8.65 (broad d, J=7.5 Hz, 1H); 8.97 (broad s, 1H); 9.33 (s, 1H); 11.4 (s, 1H).

ES: m/z=516 (MH+) base peak, m/z=499 (MH+−NH3)

The 7-amino-3-{4-[3-(2-fluoro-5-trifluoromethylphenyl)-ureido]phenyl}-1H-indole-2-carboxamide can be obtained as described in example 30.

EXAMPLE 32

7-(2-Dimethylaminoacetylamino)-3-{4-[3-(2-fluoro-5-trifluoromethylphenyl)ureido]phenyl}-1H-indole-2-carboxamide

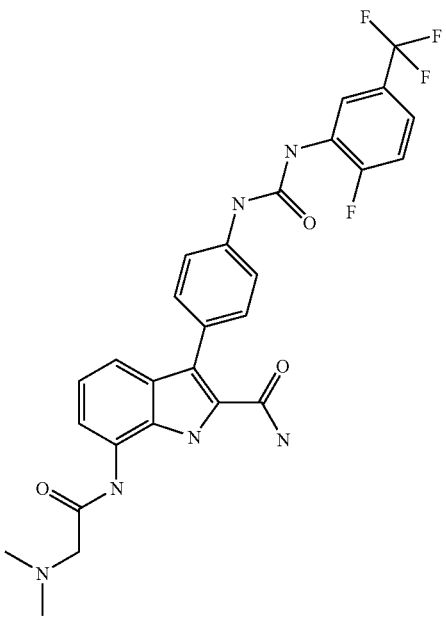

14.78 μl (0.11 mmol) of triethylamine are added, at ambient temperature, to a suspension of 50 mg (0.11 mmol) of 7-amino-3-{4-[3-(2-fluoro-5-trifluoromethylphenyl)ureido]phenyl}-1H-indole-2-carboxamide, 11 mg (0.11 mmol) of N,N-dimethylglycine, 20 mg (0.10 mmol) of 1-(3-dimethylaminopropyl)-3-ethylcarbodiimide hydrochloride and 16 mg (0.10 mmol) of 1-hydroxybenzotriazole hydrate in 6 ml of methylene chloride. 2 ml of dimethylformamide are then added in order to yridine ed the mixture. The reaction is stirred at ambient temperature for 24 h. The reaction medium is diluted by adding methylene chloride, and is then washed successively with a saturated aqueous sodium bicarbonate solution and then water. The aqueous phase is dried over anhydrous magnesium sulfate, filtered, and concentrated to dryness under reduced pressure. The crude product is purified by flash chromatography [eluent: methylene chloride/methanol (95/5 by volume)]. After concentration under reduced pressure of the fractions containing the expected product, 50 mg of 7-(2-dimethylaminoacetylamino)-3-{4-[3-(2-fluoro-5-trifluoromethylphenyl)ureido]phenyl}-1H-indole-2-carboxamide are obtained in the form of a cream solid.

1H NMR (300 MHz, (CD3)2SO d6, –δ in ppm): 2.34 (s, 6H); 3.21 (s, 2H); 6.35 (broad m, 1H); 7.02 (t, J=7.5 Hz, 1H); 7.16 (d, J=7.5 Hz, 1H); 7.39 (m, 1H); 7.43 (broad d, J=8.5 Hz, 2H); 7.51 (m, 1H); 7.58 (broad m, 1H); 7.63 (broad d, J=8.5 Hz, 2H); 7.85 (d, J=7.5 Hz, 1H); 8.64 (dd, J=2.5 and 7.5 Hz, 1H); 9.00 (broad s, 1H); 9.38 (s, 1H); 9.86 (s, 1H); 11.55 (s, 1H).

ES: m/z=557 (MH+) base peak, m/z=540 (MH+–NH3).

The 7-amino-3-{4-[3-(2-fluoro-5-trifluoromethylphenyl)-ureido]phenyl}-1H-indole-2-carboxamide can be obtained as described in example 30.

EXAMPLE 33

3-{6-[3-(2-Methoxy-5-trifluoromethylphenyl)-ureido]yridine-3-yl}-1H-indole-2-carboxamide

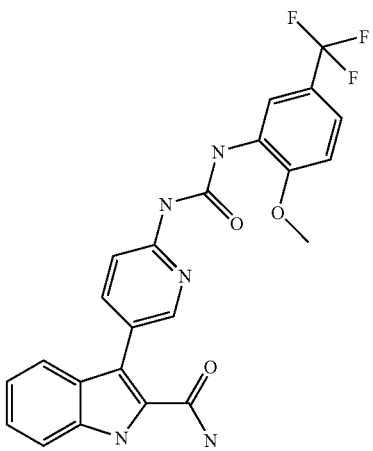

A suspension of 400 mg (1.67 mmol) of 3-bromo-1H-indole-2-carboxamide and 193 mg (0.17 mmol) of tetrakis(triphenylphosphine)palladium (0) in 9.25 ml of dioxane is stirred at ambient temperature for 10 minutes. 805 mg (1.84 mmol) of 1-(2-methoxy-5-trifluoromethylphenyl)-3-[5-(4,4,5,5-tetramethyl-1,3,2-dioxaborolan-2-yl) yridine-2-yl]urea and 10 ml of dioxane are then added at ambient temperature, followed by a solution of 389 mg (6.69 mmol) of potassium fluoride in 1.75 ml of water. The mixture is refluxed for 18 h. The reaction medium is taken up in ethyl acetate and washed with water, and the organic phase is then dried over anhydrous magnesium sulfate, filtered, and concentrated to dryness under reduced pressure. The crude is purified by flash chromatography [eluent: methylene chloride/methanol (97/3 by volume)]. The beige solid obtained after concentration of the fractions to dryness under reduced pressure is triturated with methanol and then, after filtration over sintered glass, 26 mg of 3-{6-[3-(2-methoxy-5-trifluoromethyl-phenyl)ureido]yridine-3-yl}-1H-indole-2-carboxamide, are obtained in the form of a white solid.

1H NMR (400 MHz, (CD3)2SO d6, –δ in ppm): 4.00 (s, 3H); 7.03 (broad m, 1H); 7.10 (broad t, J=7.5 Hz, 1H); 7.22 (d, J=9.0 Hz, 1H); 7.27 (broad t, J=7.5 Hz, 1H); 7.36 (dd, J=2.5 and 9.0 Hz, 1H); 7.42 (broad m, 1H); 7.49 (m, 3H); 7.88 (dd, J=2.5 and 8.5 Hz, 1H); 8.41 (d, J=2.5 Hz, 1H); 8.65 (d, J=2.5 Hz, 1H); 10.05 (s, 1H); 11.5 (very broad m, 1H); 11.75 (broad s, 1H).

ES: m/z=470 (MH+) base peak.

The 3-bromo-1H-indole-2-carboxamide can be prepared in the following way:

A mixture of 5 g (18.65 mmol) of methyl 3-bromo-1H-indole-2-carboxylate and 70 ml of 7N aqueous ammonia in methanol is heated at 100° C. for 23 h in an autoclave. The reaction medium is then evaporated to dryness under reduced pressure. The crude is purified by flash chromatography [eluent: ethyl acetate/heptane (50/50 by volume)]. The pink solid obtained after concentration of the fractions to dryness under reduced pressure is solubilized in approximately 100 ml of ethyl acetate, and a spatula of plant-derived carbon is added thereto. After stirring for a few minutes and then filtration, the filtrate is evaporated under reduced pressure and 3.11 g of 3-bromo-1H-indole-2-carboxamide are obtained in the form of a light yellow solid.

ES: m/z=239 (MH⁺) base peak.

The methyl 3-bromo-1H-indole-2-carboxylate can be prepared as described in example 1.

The 1-(2-methoxy-5-trifluoromethylphenyl)-3-[5-(4,4,5,5-tetramethyl-1,3,2-dioxaborolan-2-yl) yridine-2-yl]urea can be prepared in the following way:

A suspension of 539 mg (1.92 mmol) of pyridinehexylphosphine and 295 mg (0.52 mmol) of bis(dibenzylideneacetone)palladium in 25 ml of dioxane is stirred at ambient temperature under argon for 10 minutes. 5 g (12.82 mmol) of 1-(5-bromopyridin-2-yl)-3-(2-methoxy-5-trifluoromethylphenyl)urea are added to the reaction medium, followed by 125 ml of dioxane, 4.40 g (17.3 mmol) of bis(pinacolato) diborane and 1.89 g (19.2 mmol) of potassium acetate. The reaction is refluxed under argon for 5 h 30 min and then 300 ml of water are added at ambient temperature. The mixture is stirred at ambient temperature for 15 minutes and then filtered over sintered glass, and the solid obtained is washed with a small amount of water. 5.42 g of 1-(2-methoxy-5-trifluoromethylphenyl)-3-[5-(4,4,5,5-tetramethyl-1,3,2-dioxaborolan-2-yl) yridine-2-yl]urea are obtained in the form of a pale green solid.

EI: m/z=437 (M⁺) base peak, m/z=220 ($C_{11}H_{17}N_2O_2B^+$.), m/z=191 ($C_8H_8NOF_3^+$).

The 1-(5-bromopyridin-2-yl)-3-(2-methoxy-5-trifluoromethylphenyl)urea can be prepared in the following way:

A solution of 11.05 g (57.80 mmol) of 2-methoxy-5-trifluoromethylaniline in 100 ml of anhydrous tetrahydrofuran is added, at 0° C. over 3 minutes, to a solution of 6 g (20.23 mmol) of triphosgene in 500 ml of anhydrous tetrahydrofuran. 16.50 ml (116.80 mmol) of triethylamine are added at 0° C. The reaction is stirred at 0° C. for 10 minutes and then at ambient temperature for 1 h 45 min. A solution of 10 g (57.80 mmol) of 2-amino-5-bromopyridine in 100 ml of anhydrous tetrahydrofuran is then added at ambient temperature. The reaction is stirred at ambient temperature for 20 h. The mixture is filtered over sintered glass and the white solid obtained is washed with tetrahydrofuran and a small amount of ethyl acetate. The filtrate is evaporated to dryness under reduced pressure and a pale yellow solid is obtained. The latter is triturated with ethyl acetate and water and then, after filtration over sintered glass, 12.04 g of 1-(5-bromopyridin-2-yl)-3-(2-methoxy-5-trifluoromethylphenyl)urea are obtained in the form of a white solid.

EI: m/z=389 (M⁺), m/z=191 ($C_8H_8NOF_3^+$), m/z=172 ($C_5H_5N_2Br^+$) base peak.

EXAMPLE 34

3-{6-[3-(2-Fluoro-5-trifluoromethylphenyl)-ureido] pyridin-3-yl}-1H-indole-2-carboxamide

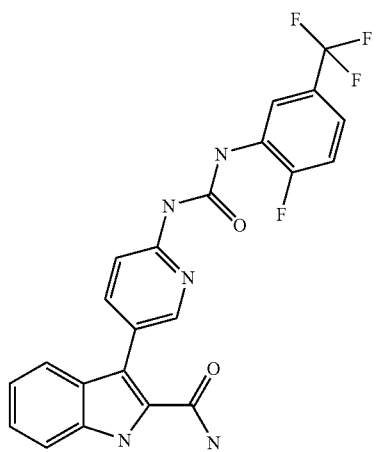

A suspension of 186 mg (0.78 mmol) of 3-bromo-1H-indole-2-carboxamide and 90 mg (0.08 mmol) of tetrakis(triphenylphosphine)palladium (0) in 9.25 ml of dioxane is stirred at ambient temperature for 10 minutes. 398 mg (0.94 mmol) of 1-(2-fluoro-5-trifluoromethylphenyl)-3-[5-(4,4,5,5-tetramethyl-1,3,2-dioxaborolan-2-yl) yridine-2-yl]urea and 10 ml of dioxane are then added at ambient temperature, followed by a solution of 181 mg (3.12 mmol) of potassium fluoride in 1.75 ml of water. The mixture is refluxed for 18 h. The reaction medium is evaporated to dryness under reduced pressure. The crude is purified by flash chromatography [eluent: methylene chloride/methanol (98/2 by volume)]. After concentration under reduced pressure of the fractions containing the expected product, 28 mg of 3-{6-[3-(2-fluoro-5-trifluoromethylphenyl)ureido]yridine-3-yl}-1H-indole-2-carboxamide are obtained in the form of a white solid.

1H NMR (400 MHz, (CD3)2SO d6, −δ in ppm): 7.10 (broad t, J=7.5 Hz, 1H); 7.12 (broad m, 1H); 7.28 (broad t, J=7.5 Hz, 1H); from 7.40 to 7.58 (m, 6H); 7.91 (dd, J=2.0 and 8.5 Hz, 1H); 8.37 (broad d, J=2.0 Hz, 1H); 8.71 (dd, J=2.0 and 7.5 Hz, 1H); 10.05 (broad s, 1H); 11.3 (very broad m, 1H); 11.75 (broad s, 1H).

ES: m/z=458(MH⁺) base peak.

EXAMPLES 35 TO 54

The following procedure is applied to each targeted reaction involving the reactants 1 to 20 and the 3-(4-aminophenyl)-1H-indole-2-carboxamide.

TABLE A

| | | Reactants used | | |
|---|---|---|---|---|
| # | Name of the isocyanate precursor | Formula | MW (g/mol) | Amount (mg) |
| 1 | 4-CHLOROPHENYL ISOCYANATE | $C_7H_4ClNO$ | 153.57 | 59.800 |
| 2 | P-TOLYL ISOCYANATE | $C_8H_7NO$ | 133.15 | 51.928 |

TABLE A-continued

Reactants used

| # | Name of the isocyanate precursor | Formula | MW (g/mol) | Amount (mg) |
|---|---|---|---|---|
| 3 | 4-FLUOROPHENYL ISOCYANATE | $C_7H_4FNO$ | 137.11 | 53.472 |
| 4 | 4-DIMETHYLAMINOPHENYL ISOCYANATE | $C_9H_{10}N_2O$ | 162.19 | 63.254 |
| 5 | 4-TERT-BUTYLPHENYL-ISOCYANATE | $C_{11}H_{13}NO$ | 175.23 | 68.339 |
| 6 | 3-FLUORO-4-METHYLPHENYL ISOCYANATE | $C_8H_6FNO$ | 151.14 | 59.944 |
| 7 | 4-(TRIFLUOROMETHYLTHIO)PHENYL ISOCYANATE | $C_8H_4F_3NOS$ | 219.19 | 85.484 |
| 8 | 4-(DIFLUOROMETHOXY)PHENYL ISOCYANATE | $C_8H_5F_2NO_2$ | 185.13 | 72.200 |
| 9 | 2-(DIFLUOROMETHOXY)PHENYL ISOCYANATE | $C_8H_5F_2NO_2$ | 185.13 | 73.680 |
| 10 | 3-METHOXYPHENYL ISOCYANATE | $C_8H_7NO_2$ | 149.15 | 59.360 |
| 11 | 4-METHOXYPHENYL ISOCYANATE | $C_8H_7NO_2$ | 149.15 | 59.360 |
| 12 | 3-CHLORO-4-FLUOROPHENYL ISOCYANATE | $C_7H_3ClFNO$ | 171.56 | 68.280 |
| 13 | 2-THIENYL ISOCYANATE | $C_5H_3NOS$ | 125.15 | 49.810 |
| 14 | 3-BROMOPHENYL ISOCYANATE | $C_7H_4BrNO$ | 198.02 | 78.810 |
| 15 | 3-FLUOROPHENYL ISOCYANATE | $C_7H_4FNO$ | 137.11 | 54.570 |
| 16 | 3-CHLOROPHENYL ISOCYANATE | $C_7H_4ClNO$ | 153.57 | 61.120 |
| 17 | 4-(TRIFLUOROMETHYL)PHENYL ISOCYANATE | $C_8H_4F_3NO$ | 187.12 | 74.470 |
| 18 | 3-ETHYLPHENYL ISOCYANATE | $C_9H_9NO$ | 147.18 | 58.580 |
| 19 | 4-ISOPROPYLPHENYL ISOCYANATE | $C_{10}H_{11}NO$ | 161.2 | 64.160 |
| 20 | 5-METHYL-2-(TRIFLUOROMETHYL)-3-FURYL ISOCYANATE | $C_7H_4F_3NO_2$ | 191.11 | 76.000 |

A solution of 3-(4-aminophenyl)-1H-indole-2-carboxamide in a solvent is prepared such that 100 mg of compound are distributed in 9 ml of THF per reactor used (reactions 1 to 13) or in 5 ml of toluene (reactions 14 to 20).

100 mg of 3-(4-aminophenyl)-1H-indole-2-carboxamide in solution at 20° C. are placed in a reactor suitable for parallel synthesis (Carrousel Radley or Buchi Syncore), and then the corresponding isocyanate is introduced (ref from 1 to 20, table A). The reaction mixture is stirred at 20° C. for 39 hours. The entire mixture is concentrated to dryness under reduced pressure, and then taken up in 5 ml of dichloromethane.

Depending on their solubility state in dichloromethane, the compounds are treated in various ways:

1. the compounds generated from the precursors 2, 5 and 14 that are soluble in dichloromethane are purified by silica gel chromatography; after combination, evaporation of the fractions containing the desired compound. The characteristics of the compounds isolated are described below.

TABLE B1

| Precursor | Purification conditions | Compound isolated |
|---|---|---|
| 2 | Biotage Quad 3, cartridge Si 12 + M, 32-63 μm, 60 Angst. Elution dichloromethane ethyl acetate, 9/1 | 3-[4-(3-p-Tolyl-ureido)phenyl]-1H-indole-2-carboxamide, 164 mg |
| 5 | Biotage Quad 3, cartridge Si 12 + M, 32-63 μm, 60 Angst. Elution dichloromethane ethyl acetate, 9/1 | 3-{4-[3-(4-tert-Butylphenyl)-ureido]phenyl}-1H-indole-2-carboxamide, 78.5 mg |
| 14 | Intelliflash, dichloromethane/acetone | 3-{4-[3-(3-Bromo-phenyl)ureido]phenyl} |

TABLE B1-continued

| Precursor | Purification conditions | Compound isolated |
|---|---|---|
| | 9/1, cartridge RS12, Silice 50 μm 60 Angst., 15 ml/min | 1H-indole-2-carboxamide, 80 mg |
| | T | % Acetone | |
| | 0 | 0 | |
| | 5 | 5 | |
| | 10 | 5 | |
| | 12 | 10 | |
| | 20 | 10 | |

2. the compounds generated from the precursors 1, 3, 4, 6, 7, 8, 9, 10, 11, 12, 13 and 15 to 20 that are insoluble under these conditions are triturated in dichloromethane, filtered, washed and then dried. The following compounds derived from the precursors 3, 7, 9 to 13 and 15 to 20 are isolated and characterized. The characteristics of the compounds isolated are described below.

TABLE B2

| Precursor | Compound isolated, amount (mg) |
|---|---|
| 3 | 3-{4-[3-(4-Fluorophenyl)ureido]phenyl}-1H-indole-2-carboxamide, 106.8 mg |
| 7 | 3-{4-[3-(4-Trifluoromethylsulfanylphenyl)-ureido]phenyl}-1H-indole-2-carboxamide, 180.7 mg |
| 9 | 3-{4-[3-(2-Difluoromethoxyphenyl)ureido]-phenyl}-1H-indole-2-carboxamide, 86.8 mg |
| 10 | 3-{4-[3-(3-Methoxyphenyl)ureido]phenyl}-1H-indole-2-carboxamide, 102.1 mg |
| 11 | 3-{4-[3-(4-Methoxyphenyl)ureido]phenyl}-1H-indole-2-carboxamide, 117.4 mg |
| 12 | 3-{4-[3-(3-Chloro-4-fluorophenyl)ureido]-phenyl}-1H-indole-2-carboxamide, 29 mg |

TABLE B2-continued

| Precursor | Compound isolated, amount (mg) |
|---|---|
| 13 | 3-[4-(3-Thiophen-2-yl-ureido)phenyl]-1H-indole-2-carboxamide, 17.7 mg |
| 15 | 3-{4-[3-(3-Fluorophenyl)ureido]phenyl}-1H-indole-2-carboxamide, 109 mg |
| 16 | 3-{4-[3-(3-Chlorophenyl)ureido]phenyl}-1H-indole-2-carboxamide, 120 mg |
| 17 | 3-{4-[3-(4-Trifluoromethylphenyl)ureido]-phenyl}-1H-indole-2-carboxamide, 147 mg |
| 18 | 3-{4-[3-(3-Ethylphenyl)ureido]phenyl}-1H-indole-2-carboxamide, 133 mg |
| 19 | 3-{4-[3-(4-Isopropylphenyl)ureido]phenyl}-1H-indole-2-carboxamide, 140 mg |
| 20 | 3-{4-[3-(5-Methyl-2-trifluoromethylfuran-3-yl)ureido]phenyl}-1H-indole-2-carboxamide, 120 mg |

3. the compounds derived from the precursors 6 and 8 are taken up in acetonitrile, triturated, filtered, washed and dried. The following compounds are isolated, identified and characterized. The characteristics of the compounds isolated are described below.

TABLE B3

| Precursor | Compound isolated and amount |
|---|---|
| 6 | 3-{4-[3-(3-Fluoro-4-methylphenyl)ureido]-phenyl}-1H-indole-2-carboxamide, 147 mg |
| 8 | 3-{4-[3-(4-Difluoromethoxyphenyl)ureido]-phenyl}-1H-indole-2-carboxamide, 135 mg |

4. the compounds derived from the precursors 1 and 4 are purified by preparative LCMS.

TABLE B4

| Precursor | Compound isolated and amount |
|---|---|
| 1 | 3-{4-[3-(4-Chlorophenyl)ureido]phenyl}-1H-indole-2-carboxamide, 73.8 mg |
| 4 | 3-{4-[3-(4-Dimethylaminophenyl)ureido]-phenyl}-1H-indole-2-carboxamide, 83.6 mg |

TABLE C

Products isolated and identified and their characteristics

| Example | Precursor | Name of the compound isolated | MH+ | Retention time (min) | Method of analysis |
|---|---|---|---|---|---|
| 35 | 5 | 3-{4-[3-(4-tert-Butyl-phenyl)ureido]phenyl}-1H-indole-2-carboxamide | 427 | 9.83 | Method B |
| 36 | 7 | 3-{4-[3-(4-Trifluoromethylsulfanyl-phenyl)ureido]phenyl}-1H-indole-2-carboxamide | 471 | 9.92 | Method B |
| 37 | 8 | 3-{4-[3-(4-Difluoromethoxy-phenyl)ureido]phenyl}-1H-indole-2-carboxamide | 437 | 3.99 | Method A |
| 38 | 6 | 3-{4-[3-(3-Fluoro-4-methylphenyl)ureido]phenyl}-1H-indole-2-carboxamide | 403 | 7.17 | Method A |
| 39 | 1 | 3-{4-[3-(4-Chloro-phenyl)ureido]phenyl}-1H-indole-2-carboxamide | 405 | 4.08 | Method A |
| 40 | 4 | 3-{4-[3-(4-Dimethylaminophenyl)-ureido]phenyl}-1H-indole-2-carboxamide | 414 | 2.73 | Method A |
| 41 | 2 | 3-[4-(3-p-Tolyl-ureido)phenyl]-1H-indole-2-carboxamide | 385 | 8.83 | Method B |
| 42 | 3 | 3-{4-[3-(4-Fluoro-phenyl)ureido]phenyl}-1H-indole-2-carboxamide | 389 | 8.59 | Method B |
| 43 | 12 | 3-{4-[3-(3-Chloro-4-fluorophenyl)ureido]-phenyl}-1H-indole-2-carboxamide | 423 | 4.17 | Method A |
| 44 | 13 | 3-[4-(3-Thiophen-2-yl-ureido)phenyl]-1H-indole-2-carboxamide | 377 | 3.64 | Method A |
| 45 | 9 | 3-{4-[3-(2-Difluoromethoxyphenyl)ureido]-phenyl}-1H-indole-2-carboxamide | 437 | 4.08 | Method A |
| 46 | 10 | 3-{4-[3-(3-Methoxy-phenyl)ureido]phenyl}-1H-indole-2-carboxamide | 401 | 3.85 | Method A |
| 47 | 11 | 3-{4-[3-(4-Methoxy-phenyl)ureido]phenyl}-1H-indole-2-carboxamide | 401 | 3.7 | Method A |
| 48 | 14 | 3-{4-[3-(3-Bromo-phenyl)ureido]phenyl}-1H-indole-2-carboxamide | 450 | 4.19 | Method A |
| 49 | 15 | 3-{4-[3-(3-Fluoro-phenyl)ureido]phenyl}-1H-indole-2-carboxamide | 389 | 3.94 | Method A |
| 50 | 16 | 3-{4-[3-(3-Chloro-phenyl)ureido]phenyl}-1H-indole-2-carboxamide | 405 | 4.13 | Method A |
| 51 | 17 | 3-{4-[3-(4-Trifluoro-methylphenyl)ureido]-phenyl}-1H-indole-2-carboxamide | 439 | 4.28 | Method A |
| 52 | 18 | 3-{4-[3-(3-Ethyl-phenyl)ureido]phenyl}-1H-indole-2-carboxamide | 399 | 4.16 | Method A |
| 53 | 19 | 3-{4-[3-(4-Isopropyl-phenyl)ureido]phenyl}-1H-indole-2-carboxamide | 413 | 4.34 | Method A |
| 54 | 20 | 3-{4-[3-(5-Methyl-2-trifluoromethylfuran-3-yl)ureido]phenyl}-1H-indole-2-carboxamide | 443 | 4.24 | Method A |

LCMS Analytical Methods

| | T min | % A |
|---|---|---|
| Method A | | |
| LCMS micromass model platform II. | 0 | 95 |
| Chromatographic conditions: | 5 | 5 |
| Eluent: A: water +0.1% HCOOH/B: | 5.5 | 5 |
| Acetonitrile | 6.5 | 95 |
| Column: Thermo Hypersil Gold, | 7 | 95 |
| 50 × 3 mm, 3 µM (Ref 25003-053030) | | |
| Gradient: see facing | | |

-continued

| | T min | % A |
|---|---|---|
| Method B | | |
| LC/MS micromass model platform II. | 0 | 95 |
| Chromatographic conditions: | 10 | 5 |
| Gradient water A +0.1% HCOOH/MeOHB. | 11 | 95 |
| Column: Waters, Xbridge, 3 × 100 mm, 3.5 μm (Ref 186003027). | 13 | 95 |
| Gradient: see facing | | |

LCMS Preparative Methods:

The products are purified by LC/MS using a Waters FractionsLynx system composed of a Waters model 600 gradient pump, a Waters model 515 regeneration pump, a Waters Reagent Manager dilution pump, a Waters model 2700 auto-injector, two Rheodyne model LabPro valves, a Waters model 996 diode array detector, a Waters model ZMD mass spectrometer and a Gilson model 204 fraction collector. The system is controlled by the Waters FractionLynx software. The separation is carried out alternately on two Waters Symmetry columns ($C_{18}$, 5 μm, 19×50 mm, catalog reference 186000210), one column undergoing regeneration with a 95/5 (v/v) water/acetonitrile mixture comprising 0.07% (v/v) of trifluoroacetic acid, while the other column is being used for separation. The columns are eluted using a linear gradient of from 5 to 95% of acetonitrile comprising 0.07% (v/v) of trifluoroacetic acid in water comprising 0.07% (v/v) of trifluoroacetic acid, at a flow rate of 10 ml/min. At the outlet of the separation column, one-thousandth of the effluent is separated by means of an LC Packing Accurate, diluted with methyl alcohol at a flow rate of 0.5 ml/min and sent to the detectors, in a proportion of 75% to the diode array detector and the remaining 25% to the mass spectrometer. The rest of the effluent (999/1000) is sent to the fraction collector, where the flow is discarded for as long as the mass of the expected product is not detected by the FractionLynx software. The molecular formulae of the expected products are supplied to the FractionLynx software, which actuates the collection of the product when the mass signal detected corresponds to the ion $[M+H]^+$ and/or to $[M+Na]^+$. In certain cases, depending on the analytical LC/MS results, when an intense ion corresponding to $[M+2H]^{++}$ was detected, the value corresponding to half the calculated molecular mass (MW/2) is also supplied to the FractionLynx software. Under these conditions, the collection is also actuated when the mass signal for the ion $[M+2H]^{++}$ and/or $[M+Na+H]^{++}$ is detected. The products are collected in a tared glass tube. After collection, the solvents are evaporated in a centrifugal evaporator and the amounts of products are determined by weighing the tubes after evaporation of the solvents.

EXAMPLE 55

5-fluoro-3-{4-[3-(2-fluoro-5-trifluoromethyl-phenyl)ureido]phenyl}-1H-indole-2-carboxamide

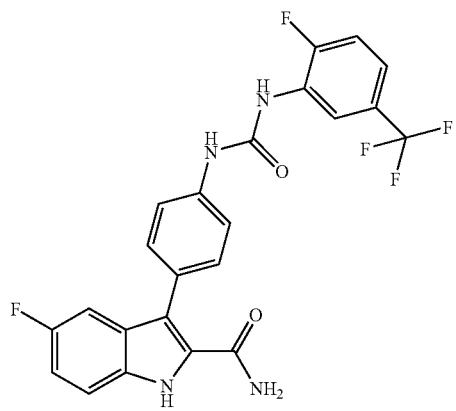

EXAMPLE 56

6-fluoro-3-{4-[3-(2-fluoro-5-trifluoro-methylphenyl)ureido]phenyl}-1H-indole-2-carboxamide

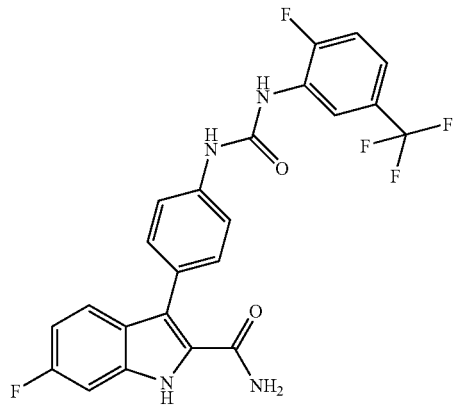

EXAMPLE 57

3-{4-[3-(2-fluoro-5-trifluoromethylphenyl)-methylcarbonylamino]phenyl}-1H-indole-2-carboxamide

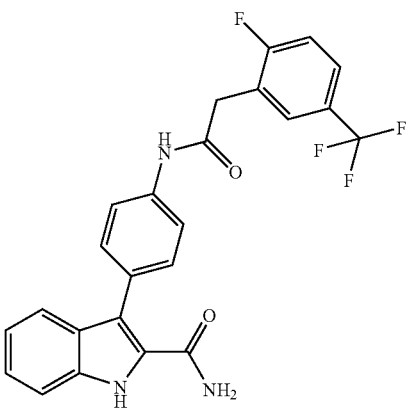

EXAMPLE 58

3-{4-[3-(2-fluoro-5-trifluoromethylphenyl)-ureido]-3-fluorophenyl}-1H-indole-2-carboxamide

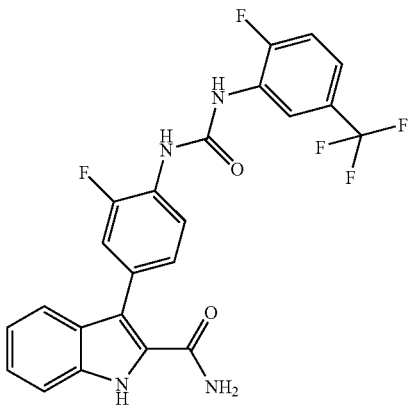

EXAMPLE 59

3-{4-[3-(2-fluoro-5-trifluoromethylphenyl)-ureido]-3-methylphenyl}-1H-indole-2-carboxamide

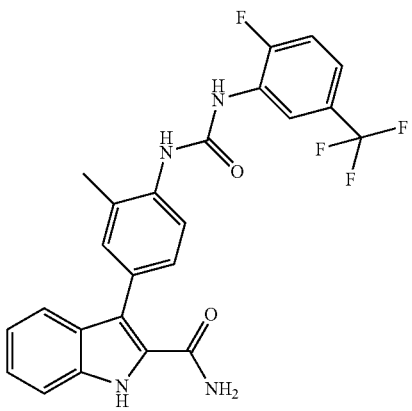

EXAMPLE 60

4-methoxy-3-{4-[3-(2-fluoro-5-trifluoromethylphenyl)-ureido]phenyl}-1H-indole-2-carboxamide

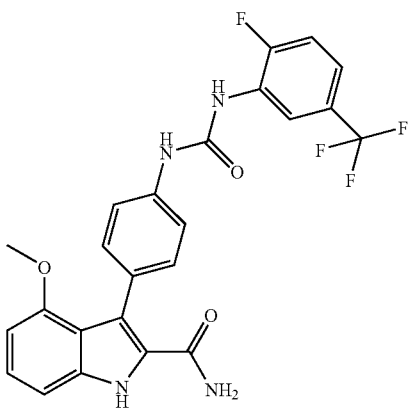

EXAMPLE 61

5-methoxy-3-{4-[3-(2-fluoro-5-trifluoromethylphenyl)ureido]phenyl}-1H-indole-2-carboxamide

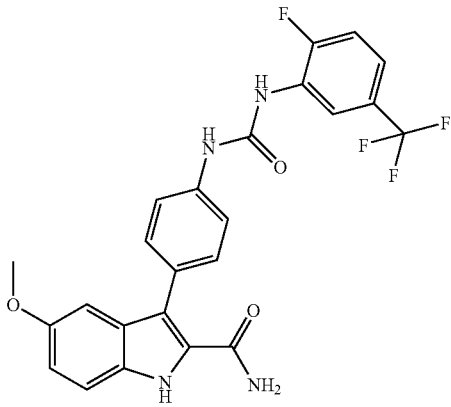

EXAMPLE 62

5-nitro-3-{4-[3-(2-fluoro-5-trifluoromethylphenyl)ureido]phenyl}-1H-indole-2-carboxamide

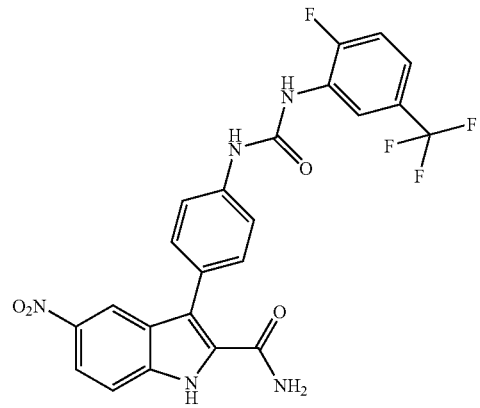

EXAMPLE 63

5-trifluoromethoxy-3-{4-[3-(2-fluoro-5-trifluoromethylphenyl)ureido]phenyl}-1H-indole-2-carboxamide

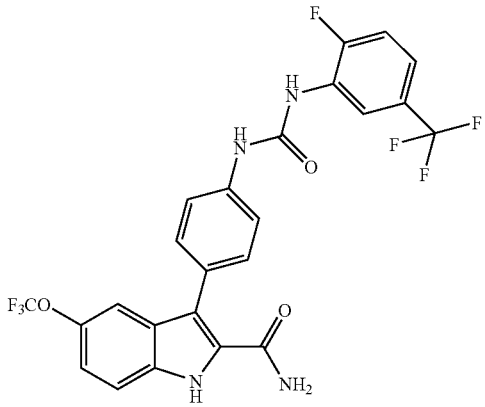

EXAMPLE 64

7-(2-morpholin-1-ylethoxy)-3-{4-[3-(2-fluoro-5-trifluoromethylphenyl)ureido]phenyl}-1H-indole-2-carboxamide

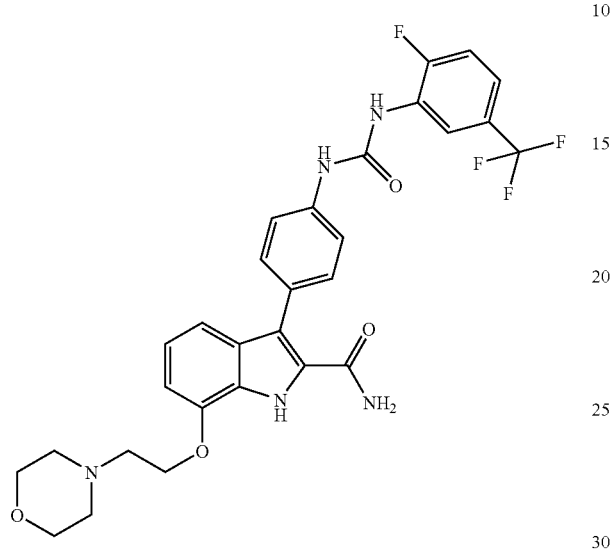

EXAMPLE 66

7-(3-pyridin-3-ylcarbonylamino)-3-{4-[3-(2-fluoro-5-trifluoromethylphenyl)ureido]phenyl}-1H-indole-2-carboxamide

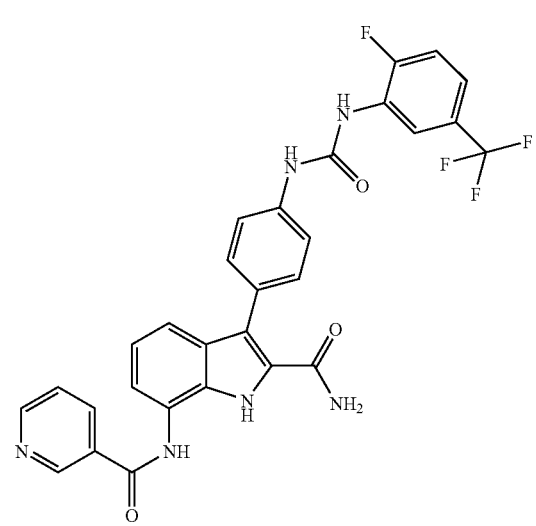

EXAMPLE 65

7-(2-pyrrolidin-1-ylethoxy-3-{4-[3-(2-fluoro-5-trifluoromethylphenyl)ureido]phenyl}-1H-indole-2-carboxamide

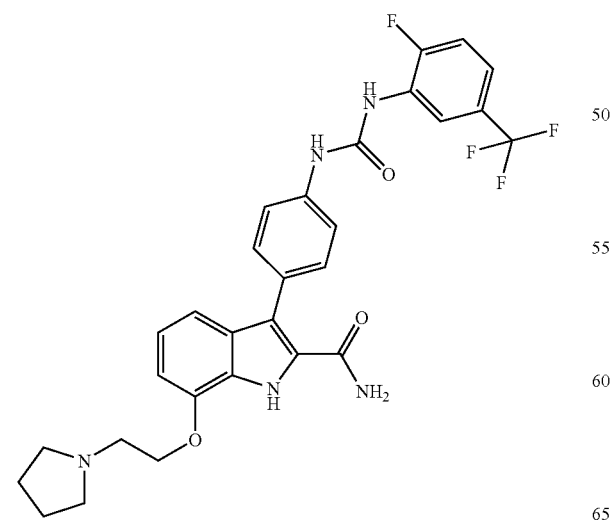

EXAMPLE 67

7-(3-methoxyethylamino)-3-{4-[3-(2-fluoro-5-trifluoromethylphenyl)ureido]phenyl}-1H-indole-2-carboxamide

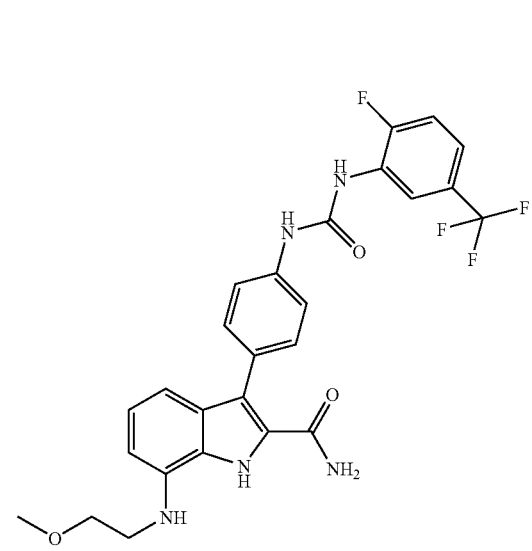

EXAMPLE 68

7-hydroxy-3-{4-[3-(2-fluoro-5-trifluoromethylphenyl)ureido]phenyl}-1H-indole-2-carboxamide

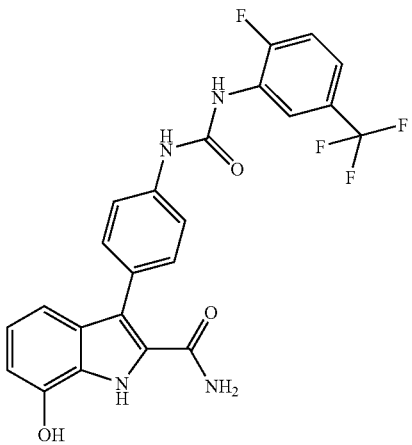

EXAMPLE 69

7-methoxy-3-{4-[3-(2-fluoro-5-trifluoromethylphenyl)ureido]phenyl}-1H-indole-2-carboxamide

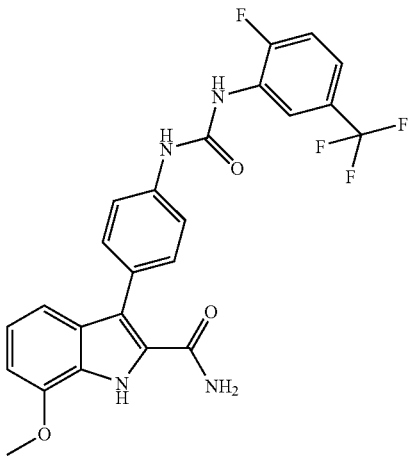

EXAMPLE 70

6-2-morpholin-1-ylethoxy)-3-{4-[3-(2-fluoro-5-trifluoromethylphenyl)ureido]phenyl}-1H-indole-2-carboxamide

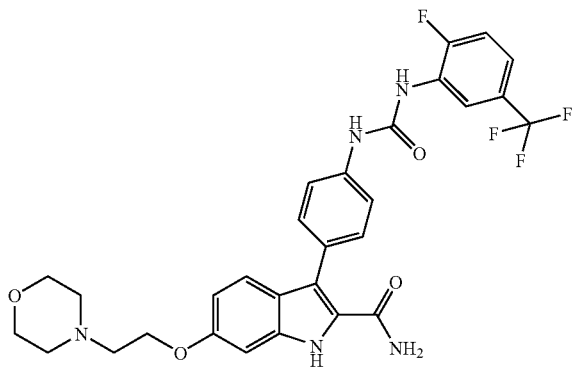

EXAMPLE 71

3-{4-[3-(2-fluoro-4-hydroxy-5-trifluoromethylphenyl)ureido]phenyl}-1H-indole-2-carboxamide

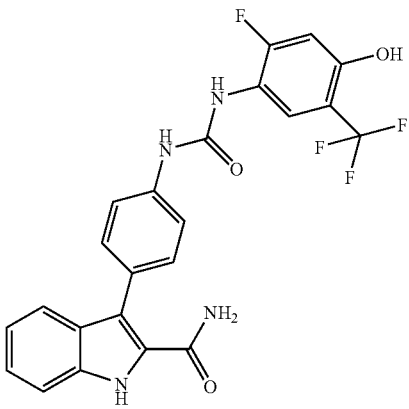

EXAMPLE 72

3-{4-[3-(4-chloro-5-trifluoromethylphenyl)ureido]phenyl}1H-indole-2-carboxamide

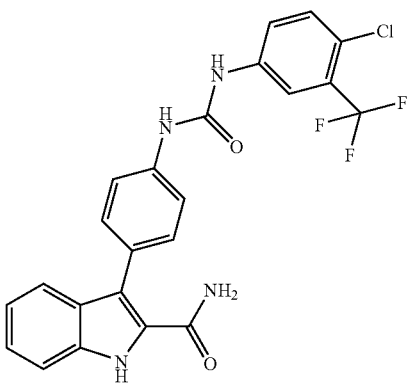

MS: m/z=473 (MH$^+$).
Retention time (min)=4.2

EXAMPLE 73

7-(2-morpholin-1-ylethoxy)-3-{4-[3-(4-fluoro-5-trifluoromethylphenyl)ureido]phenyl}-1H-indole-2-carboxamide

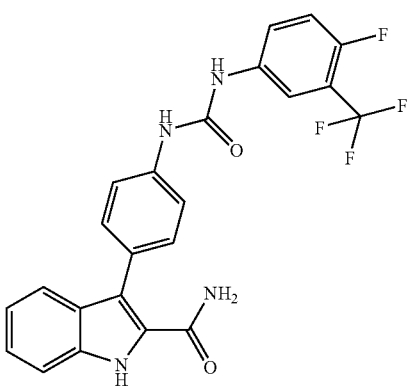

MS: m/z=457 (MH$^+$).
Retention time (min)=4.0

EXAMPLE 74
7-(2-morpholin-1-ylethoxy)-3-{4-[3-(4-methyl-3-trifluoromethylphenyl)ureido]phenyl}-1H-indole-2-carboxamide

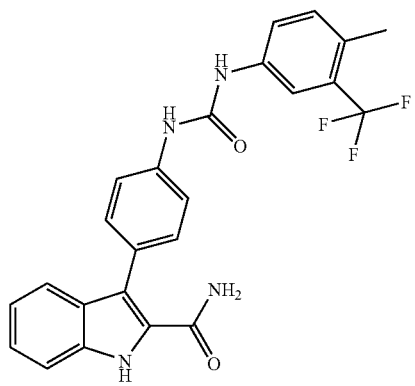

MS: m/z=453 (MH⁺).
Retention time (min)=4.12

EXAMPLE 75
3-{4-[3-(4-(pyrrolidin-1-ylmethoxy)-3-trifluoromethylphenyl)ureido]phenyl}-1H-indole-2-carboxamide

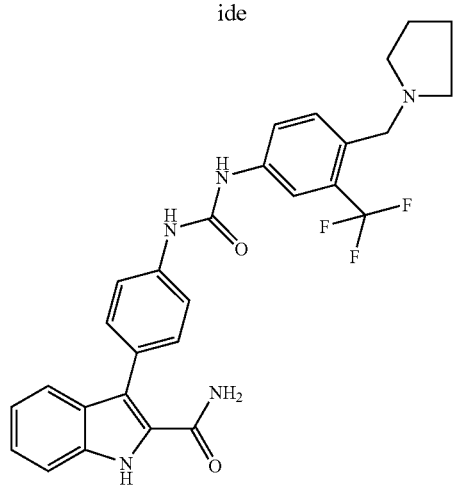

EXAMPLE 76
3-{4-[3-(4-(4-methylpiperazin-1-ylmethyl)-3-trifluoromethylphenyl)ureido]phenyl}-1H-indole-2-carboxamide

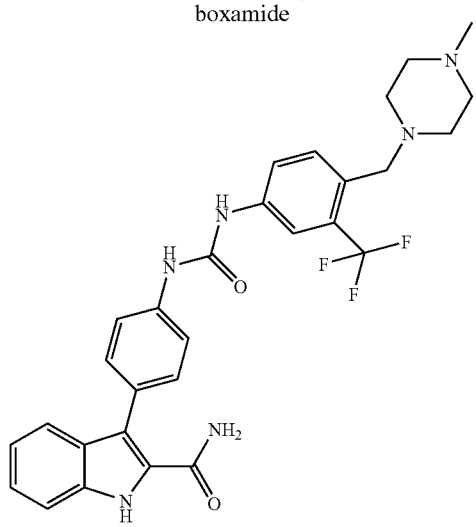

EXAMPLE 77
3-{4-[3-(2-fluorophenyl)ureido]phenyl}-1H-pyrrolo[3,2-b]pyridine-2-carboxamide

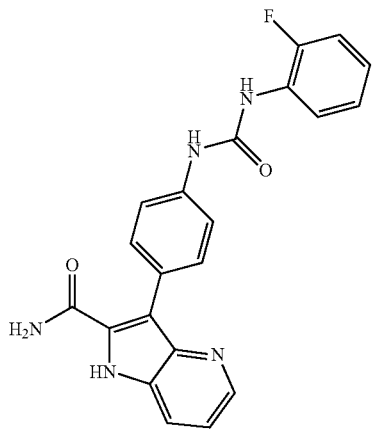

MS: m/z=390 (MH⁺).
Retention time (min)=2.8

EXAMPLE 78
3-{4-[3-(2-methoxyphenyl)ureido]phenyl}-1H-pyrrolo[3,2-b]pyridine-2-carboxamide

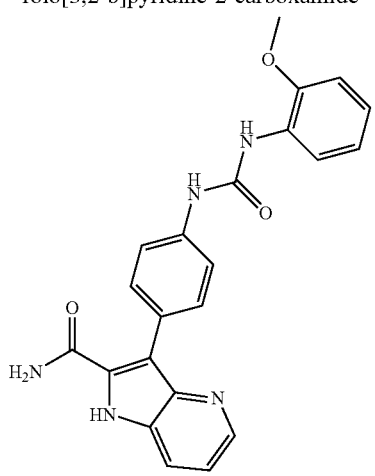

MS: m/z=402 (MH⁺).
Retention time (min)=2.9

EXAMPLE 79
3-{4-[3-(2-trifluoromethylphenyl)ureido]phenyl}-1H-pyrrolo[3,2-b]pyridine-2-carboxamide

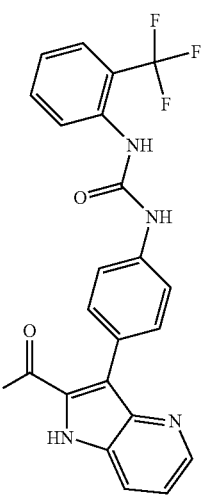

MS: m/z=440 (MH+).
Retention time (min)=3.1

EXAMPLE 80

3-[4-(3-o-tolylureido)phenyl]-1H-pyrrolo[3,2-b]pyridine-2-carboxamide

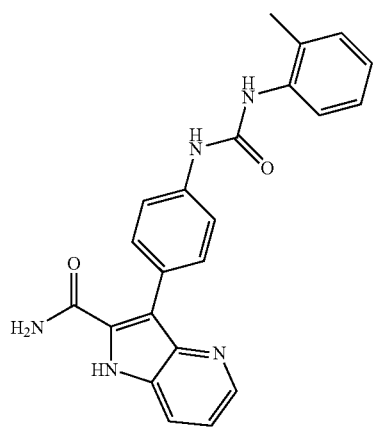

MS: m/z=386 (MH+).
Retention time (min)=2.9

EXAMPLE 81

3-{4-[3-(3-fluorophenyl)ureido]phenyl}-1H-pyrrolo[3,2-b]pyridine-2-carboxamide

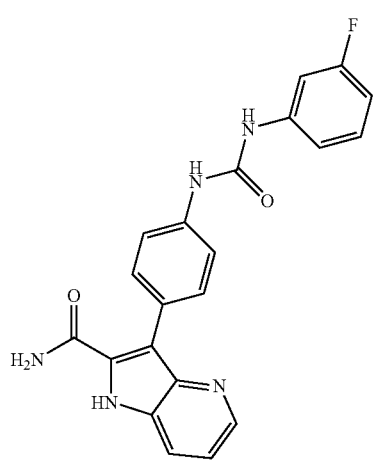

MS: m/z=390 (MH+).
Retention time (min)=3

EXAMPLE 82

3-{4-[3-(3-methoxyphenyl)ureido]phenyl}-1H-pyrrolo[3,2-b]pyridine-2-carboxamide

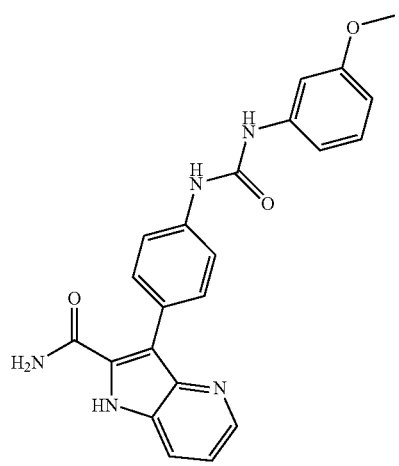

MS: m/z=402 (MH+).
Retention time (min)=2.8

EXAMPLE 83

3-{4-[3-(3-trifluoromethylphenyl)ureido]phenyl}-1H-pyrrolo[3,2-b]pyridine-2-carboxamide

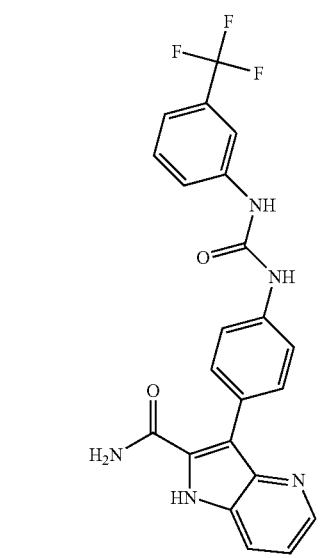

MS: m/z=440 (MH+).
Retention time (min)=3.3

EXAMPLE 84

3-[4-(3-m-tolylureido)phenyl]-1H-pyrrolo[3,2-b]pyridine-2-carboxamide

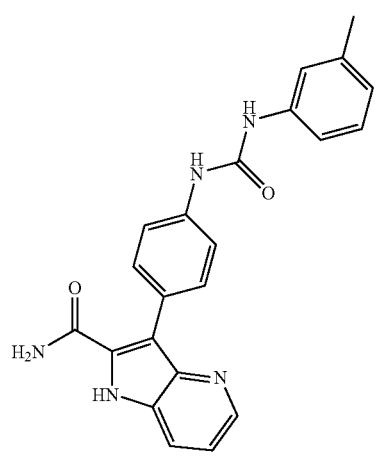

MS: m/z=386 (MH+).

Retention time (min)=3

EXAMPLE 85

3-{4-[3-(4-fluorophenyl)ureido]phenyl}-1H-pyrrolo[3,2-b]pyridine-2-carboxamide

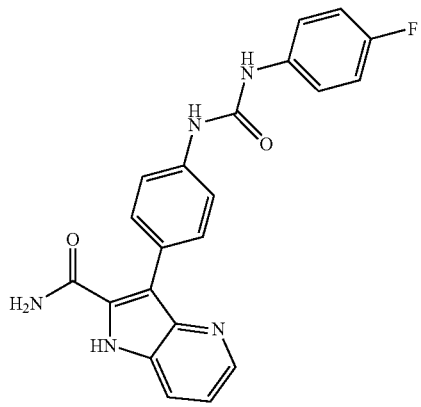

MS: m/z=390 (MH+).

Retention time (min)=2.9

EXAMPLE 86

3-{4-[3-(4-methoxyphenyl)ureido]phenyl}-1H-pyrrolo[3,2-b]pyridine-2-carboxamide

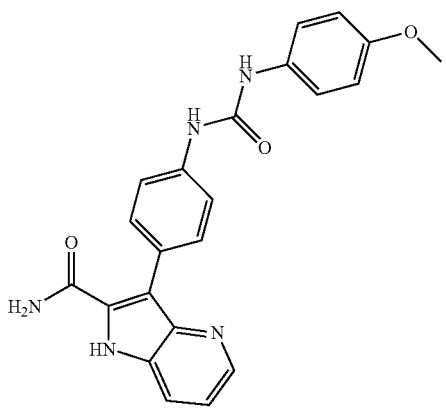

MS: m/z=402 (MH+).

Retention time (min)=2.7

EXAMPLE 87

3-{4-[3-(4-trifluoromethylphenyl)-ureido]phenyl}-1H-pyrrolo[3,2-b]pyridine-2-carboxamide

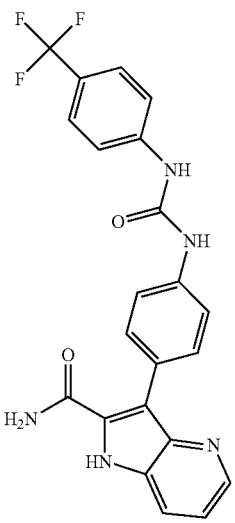

MS: m/z=440 (MH+).

Retention time (min)=3.4

EXAMPLE 88

3-[4-(3-p-tolylureido)phenyl]-1H-pyrrolo[3,2-b]pyridine-2-carboxamide

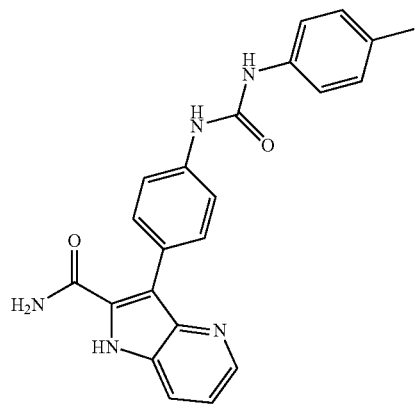

MS: m/z=386 (MH⁺).

Retention time (min)=3

EXAMPLE 89

3-{4-[3-(4-chloro-3-trifluoromethylphenyl)-ureido]phenyl}-1H-pyrrolo[3,2-b]pyridine-2-carboxamide

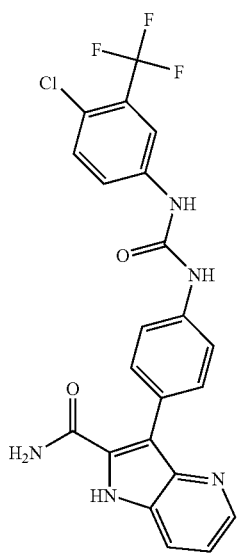

MS: m/z=474 (MH⁺).

Retention time (min)=3.6

EXAMPLE 90

3-{4-[3-(2-chloro-5-trifluoromethylphenyl)-ureido]phenyl}-1H-pyrrolo[3,2-b]pyridine-2-carboxamide

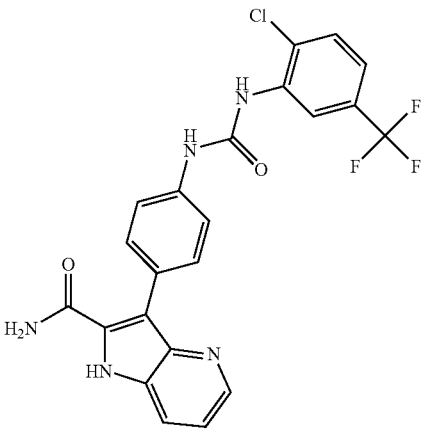

MS: m/z=474 (MH⁺).

Retention time (min)=3.4

EXAMPLE 91

3-{4-[3-(2-fluoro-3-trifluoromethylphenyl)-ureido]phenyl}-1H-pyrrolo[3,2-b]pyridine-2-carboxamide

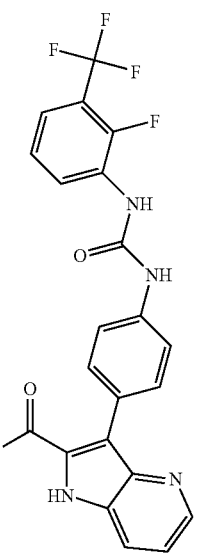

MS: m/z=458 (MH⁺).

Retention time (min)=3.4

EXAMPLE 92

3-{4-[3-(4-fluoro-3-trifluoromethylphenyl)-ureido]phenyl}-1H-pyrrolo[3,2-b]pyridine-2-carboxamide

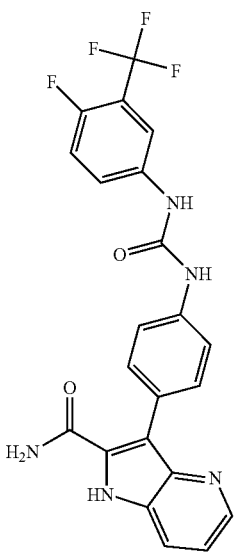

MS: m/z=458 (MH$^+$).

Retention time (min)=3.4

EXAMPLE 93

3-{4-[3-(3-fluoro-5-trifluoromethylphenyl)-ureido]phenyl}-1H-pyrrolo[3,2-b]pyridine-2-carboxamide

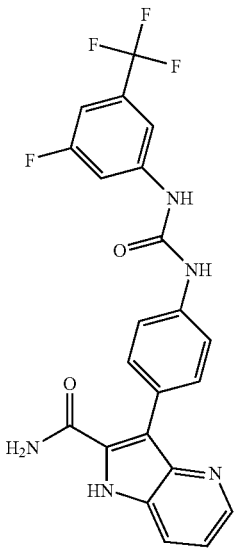

MS: m/z=458 (MH$^+$).
Retention time (min)=3.5

EXAMPLE 94

3-{4-[3-($^4$-methyl-3-trifluoromethylphenyl)-ureido]phenyl}-1H-pyrrolo[3,2-b]pyridine-2-carboxamide

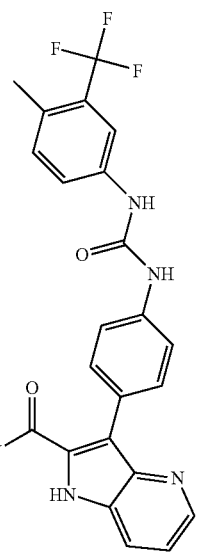

MS: m/z=454 (MH$^+$).

Retention time (min)=3.5

EXAMPLE 95

3-{4-[3-($^4$-trifluoromethoxyphenyl)-ureido]phenyl}1H-pyrrolo[3,2-b]pyridine-2-carboxamide

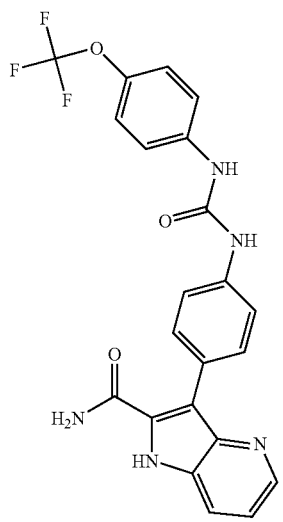

MS: m/z=456 (MH$^+$).

Retention time (min)=3.5

EXAMPLE 96

3-{4-[3-(4-difluoromethoxyphenyl)-ureido]phenyl}1H-pyrrolo[3,2-b]pyridine-2-carboxamide

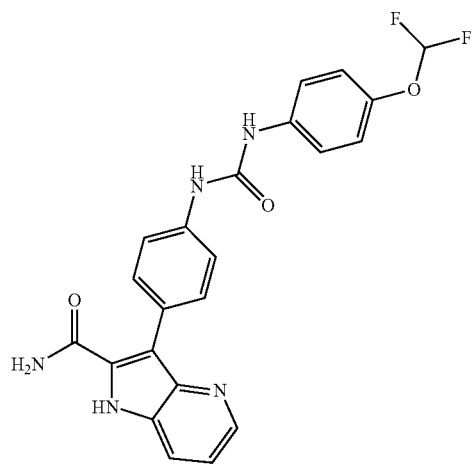

MS: m/z=438 (MH$^+$).

Retention time (min)=3.2

EXAMPLE 97

3-{4-[3-(3,4-dimethylphenyl)ureido]phenyl}-1H-pyrrolo[3,2-b]pyridine-2-carboxamide

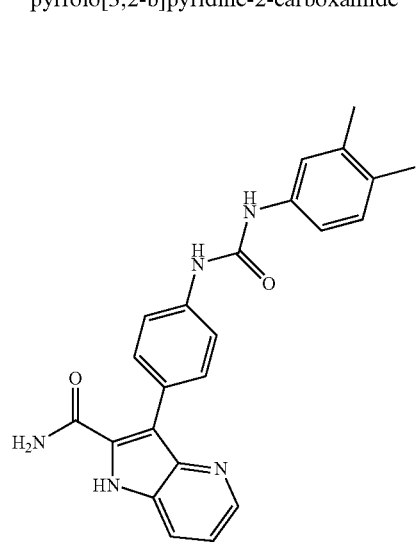

MS: m/z=400 (MH$^+$).
Retention time (min)=3.2

EXAMPLE 98

3-{4-[3-(3,4-dimethoxyphenyl)ureido]-phenyl}-1H-pyrrolo[3,2-b]pyridine-2-carboxamide

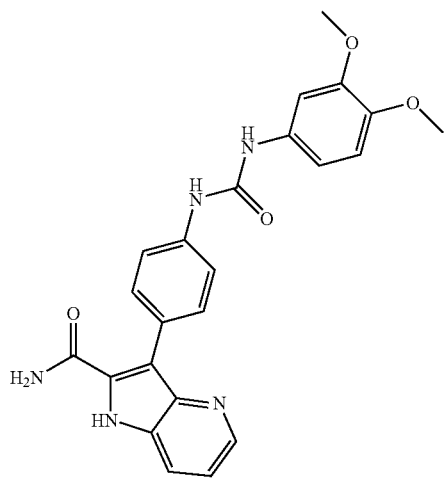

MS: m/z=432 (MH$^+$).
Retention time (min)=2.6

EXAMPLE 99

3-{4-[3-(3,5-dimethoxyphenyl)ureido]-phenyl}-1H-pyrrolo[3,2-b]pyridine-2-carboxamide

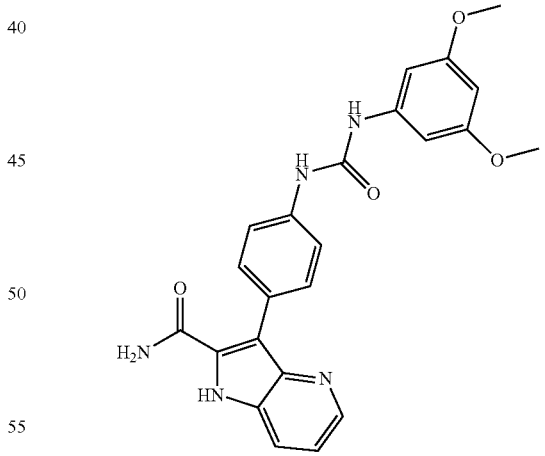

MS: m/z=432 (MH$^+$).
Retention time (min)=2.9

EXAMPLE 100

3-{4-[3-(2,5-dimethylphenyl)ureido]-phenyl}-1H-pyrrolo[3,2-b]pyridine-2-carboxamide

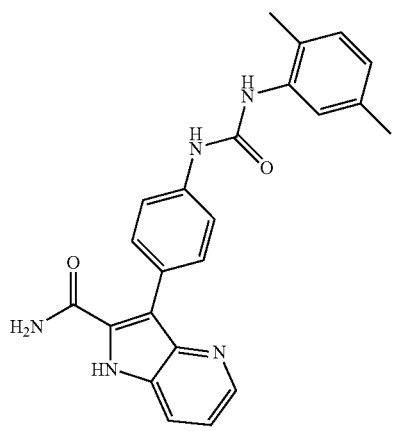

MS: m/z=400 (MH⁺).

Retention time (min)=3.1

EXAMPLE 101

3-{4-[3-(2-methoxy-5-methylphenyl)ureido]-phenyl}1H-pyrrolo[3,2-b]pyridine-2-carboxamide

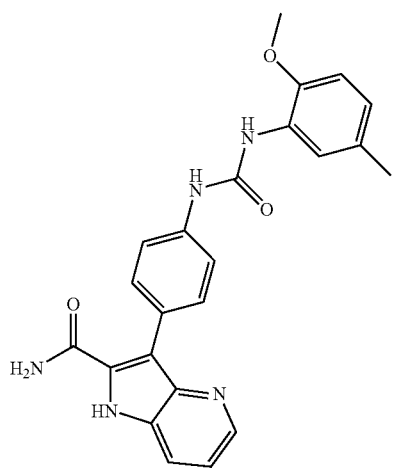

MS: m/z=416 (MH⁺).

Retention time (min)=3.1

EXAMPLE 102

3-{4-[3-(2,5-dimethoxyphenyl)ureido]-phenyl}-1H-pyrrolo[3,2-b]pyridine-2-carboxamide

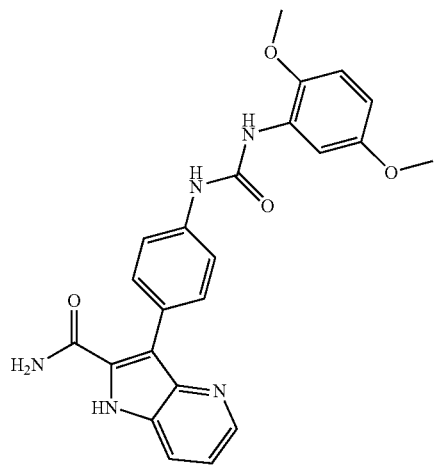

MS: m/z=432 (MH⁺).

Retention time (min)=3

EXAMPLE 103

3-{4-[3-(3-chloro-4-difluoromethoxyphenyl)ureido]-phenyl}-1H-pyrrolo[3,2-b]pyridine-2-carboxamide

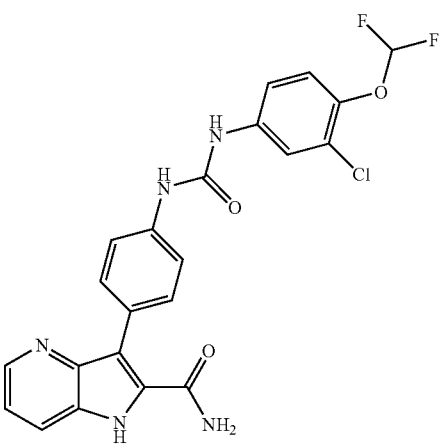

MS: m/z=471 (MH⁺).

EXAMPLE 104

3-{4-[3-(3,5-dimethylphenyl)ureido]-phenyl}-1H-pyrrolo[3,2-b]pyridine-2-carboxamide

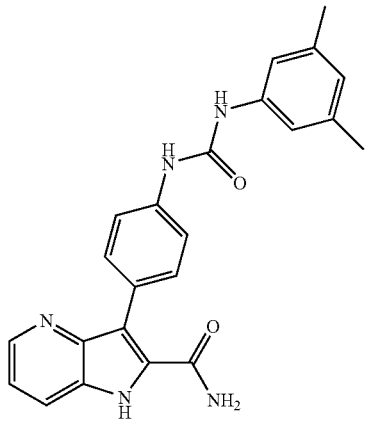

MS: m/z=400 (MH+).

Determination of the Activity of the Compounds—Experimental Protocols

2. KDR

The inhibitory effect of the compounds is determined in an assay for phosphorylation of substrate by the KDR enzyme in vitro using a scintillation technique (96-well plate, NEN).

The cytoplasmic domain of the human KDR enzyme was cloned in the form of a GST fusion into the baculovirus expression vector pFastBac. The protein was expressed in SF21 cells and purified to approximately 60% homogeneity.

The kinase activity of KDR is measured in 20 mM MOPS, 10 mM $MgCl_2$, 10 mM $MnCl_2$, 1 mM DTT, 2.5 mM EGTA, 10 mM β-glycerophosphate, pH=7.2, in the presence of 10 mM $MgCl_2$, 100 μM $Na_3VO_4$, 1 mM NaF. 10 μl of the compound are added to 70 μl of kinase buffer containing 100 ng of KDR enzyme at 4° C. The reaction is initiated by adding 20 μl of solution containing 2 μg of substrate (SH2-SH3 fragment of PLCγ expressed in the form of a GST fusion protein), 2 μCi γ $^{33}$P[ATP] and 2 μM cold ATP. After incubation at 37° C. for 1 hour, the reaction is stopped by adding 1 volume (100 μl) of 200 mM EDTA. The incubation buffer is removed and the wells are washed three times with 300 μl of PBS. The radioactivity is measured in each well using a Top Count NXT radioactivity counter (Packard).

The background noise is determined by measuring the radioactivity in four different wells containing the radioactive ATP and the substrate alone.

A control for total activity is measured in four different wells containing all the reactants (γ$^{33}$P-[ATP], KDR and PLCY substrate) but in the absence of compound.

The inhibition of the KDR activity with the compound of the invention is expressed as percentage inhibition of the control activity determined in the absence of compound.

The compound SU5614 (Calbiochem) (1 μM) is included in each plate as an inhibition control.

2. Tie2

The human Tie2 coding sequence corresponding to the intracellular domain amino acids 776-1124 was generated by PCR using the cDNA isolated from human placenta as a model. This sequence was introduced into a baculovirus expression vector pFastBacGT in the form of a GST fusion protein.

The inhibitory effect of the molecules is determined in an assay for phosphorylation of PLC by Tie2 in the presence of GST-Tie2 purified to approximately 80% homogeneity. The substrate is made up of the SH2-SH3 fragments of PLC expressed in the form of a GST fusion protein.

The kinase activity of Tie2 is measured in a 20 mM MOPS buffer, pH 7.2, containing 10 mM $MgCl_2$, 10 mM $MnCl_2$, 1 mM DTT and 10 mM of glycerophosphate. A reaction mixture made up to 70 μl of kinase buffer containing 100 ng of GST-Tie2 enzyme is deposited into each well of a 96-well FlashPlate kept on ice. 10 μl of the test molecule diluted in DMSO at a maximum concentration of 10% are then added. For a given concentration, each measurement is determined in quadruplicate. The reaction is initiated by adding 20 μl of solution containing 2 μg of GST-PLC, 2 μM of cold ATP and 1 μCi of $^{33}$P [ATP]. After incubation at 37° C. for 1 hour, the reaction is stopped by adding 1 volume (100 μl) of 200 mM EDTA. After the incubation buffer has been removed, the wells are washed three times with 300 μl of PBS. The radioactivity is measured on a Wallac MicroBeta 1450.

The inhibition of the Tie2 activity is calculated and expressed as percentage inhibition with respect to the control activity determined in the absence of compound.

The products according to the present invention have an IC50 for KDR or Tie2 or both, in general, of less than 1 μm, and preferably less than 500 nM, and even more preferably less than 100 nM. Among these products, some have an IC50 for FAK, in general, of less than 1 μm, and preferably less than 500 nM, and even more preferably less than 100 nM. For example, the product of example 10 has an IC50 value of 303 nM for FAK.

TABLE 1

Results:

| Structure | Example | KDR IC 50 (nM) | TIE2 IC 50 (nM) |
|---|---|---|---|
| (structure 1) | 1 | 35 | 3 |
| (structure 2) | 2 | 12 | 4 |
| (structure 3) | 3 | 1519 | 296 |

TABLE 1-continued

Results:

| Structure | Example | KDR IC 50 (nM) | TIE2 IC 50 (nM) |
|---|---|---|---|
| (structure) | 4 | 181 | 19 |
| (structure) | 5 | 50 | 6 |
| (structure) | 6 | 47 | 16 |

TABLE 1-continued

Results:

| Structure | Example | KDR IC 50 (nM) | TIE2 IC 50 (nM) |
|---|---|---|---|
| 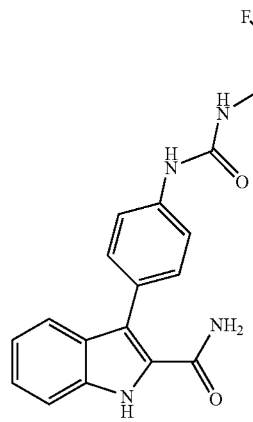 | 7 | 1753 | 142 |
| 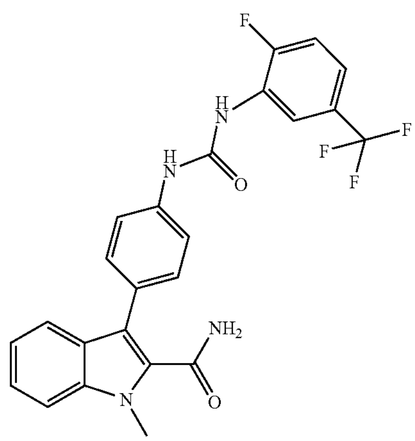 | 8 | 260 | 27 |
| 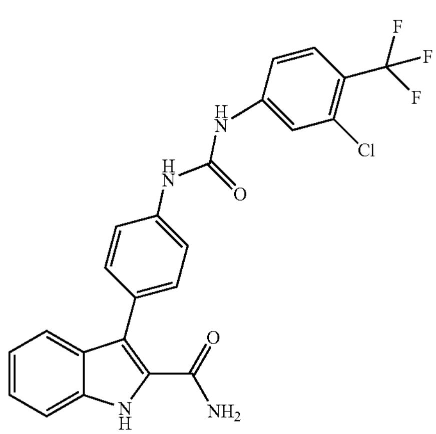 | 9 | 138 | 17 |

TABLE 1-continued
Results:
| Structure | Example | KDR IC 50 (nM) | TIE2 IC 50 (nM) |
|---|---|---|---|
| 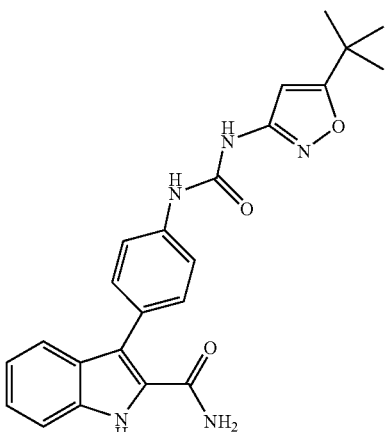 | 10 | 37 | 3 |
| 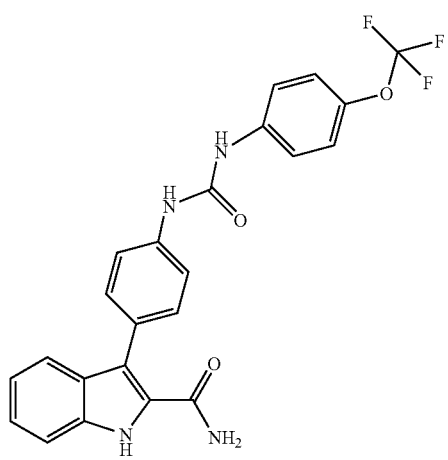 | 11 | 153 | 105 |
| 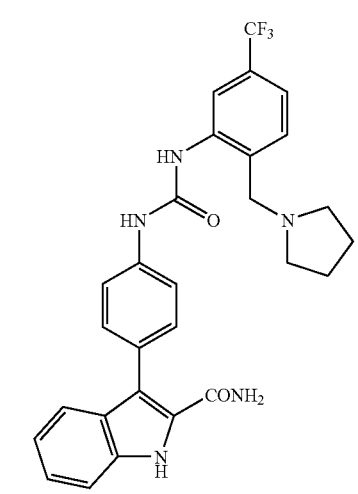 | 19 | 1894 | 220 |

TABLE 1-continued

Results:

| Structure | Example | KDR IC 50 (nM) | TIE2 IC 50 (nM) |
|---|---|---|---|
| (structure) | 20 | 234 | 59 |
| (structure) | 21 | 195 | 32 |
| (structure) | 23 | 90 | 7 |

TABLE 1-continued
Results:
| Structure | Example | KDR IC 50 (nM) | TIE2 IC 50 (nM) |
|---|---|---|---|
| 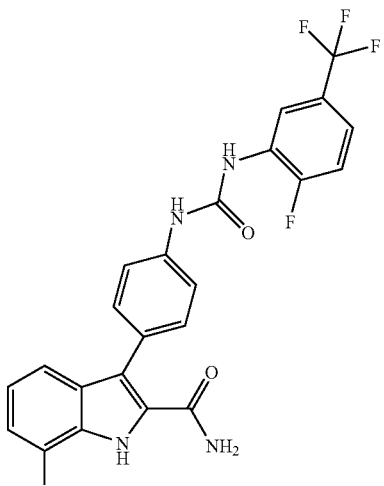 | 30 | 31 | 7 |
| 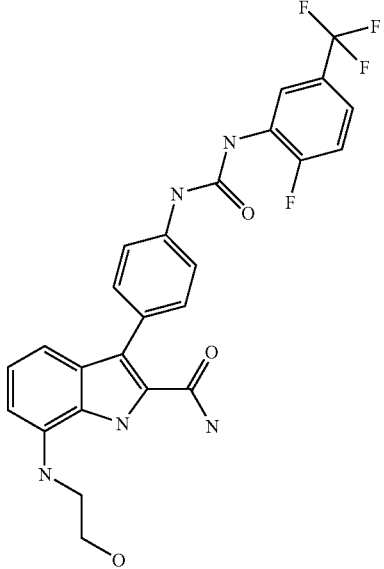 | 31 | 75 | 6 |

TABLE 1-continued

Results:

| Structure | Example | KDR IC 50 (nM) | TIE2 IC 50 (nM) |
|---|---|---|---|
| 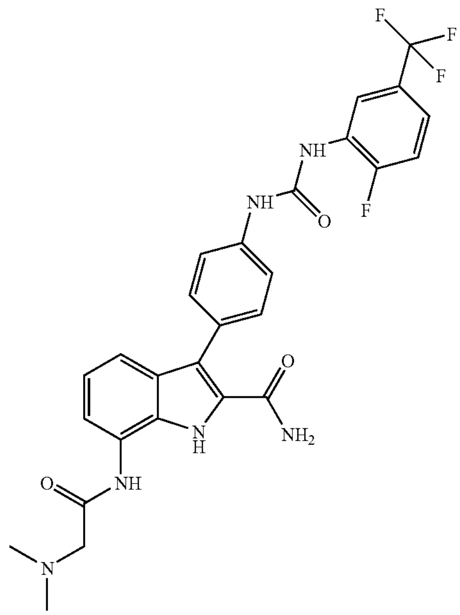 | 32 | 144 | 28 |
| 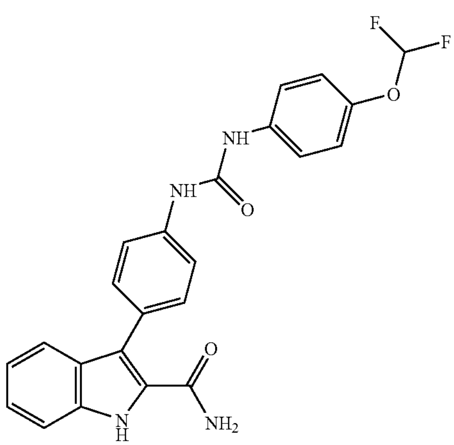 | 37 | 199 | 291 |
| 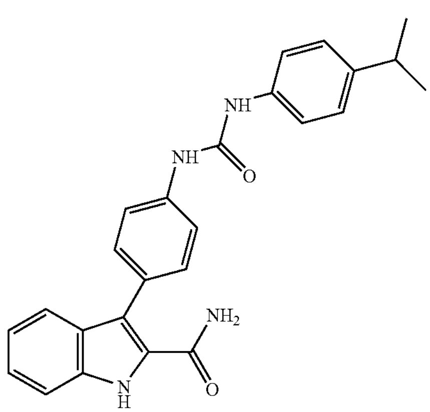 | 53 | 153 | 151 |

What is claimed is:

1. A compound according to formula (I):

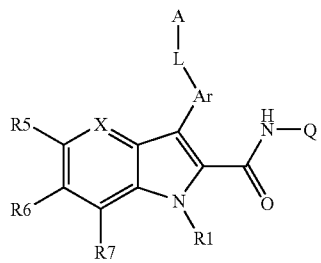

Formula (I)

in which:
a) A and Ar are independently selected from the group consisting of: aryl, and substituted aryl, and are such that Ar-L-A is:

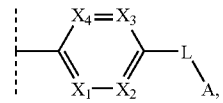

in which each X1, X2, X3 and X4 is independently C—R11, in which R11 is selected from the group consisting of H, halogen, NO₂, R2, CN, O(R2), OC(O)(R2), OC(O)N(R2)(R3), OS(O₂)(R2), N(R2)(R3), N=C(R2)(R3), N(R2)C(O)(R3), N(R2)C(O)O(R3), N(R4)C(O)N(R2)(R3), N(R4)C(S)N(R2)(R3), N(R2)S(O₂)(R3), C(O)(R2), C(O)O(R2), C(O)N(R2)(R3), C(=N(R3))(R2), C(=N(OR3))(R2), S(R2), S(O)(R2), S(O₂)(R2), S(O₂)O(R2), and S(O₂)N(R2)(R3);

b) R1 is H or alkyl, optionally substituted;
c) X is CR12;
d) L is NH—CO—NH;
e) R5, R6, R7 and R12 are each independently selected from the group consisting of: H, halogen, CF₃, NO₂, R2, CN, O(R2), OC(O)(R2), OC(O)N(R2)(R3), OS(O₂)(R2), N(R2)(R3), N=C(R2)(R3), N(R2)C(O)(R3), N(R2)C(O)O(R3), N(R4)C(O)N(R2)(R3), N(R2)C(O)R3N(R4)₂, NHC(O)R2N(R3)(R4), N(R4)C(S)N(R2)(R3), N(R2)C(S)R3N(R4)₂, NHC(S)R2N(R3)(R4), N(R2)S(O₂)(R3), OS(O₂)(R3), C(O)(R2), C(O)O(R2), C(O)N(R2)(R3), C(=N(R3))(R2), C(=N(OR3))(R2), S(R2), S(O)(R2), S(O₂)(R2), S(O₂)O(R2), and S(O₂)N(R2) (R3);

f) each R2, R3, R4 is independently selected from the group consisting of H, alkyl, alkylene, alkynyl, aryl, alkylaryl, heteroaryl, alkylheteroaryl, cycloalkyl, alkylcycloalkyl, heterocyclyl, alkylheterocyclyl, substituted alkyl, substituted alkylene, substituted alkynyl, substituted aryl, substituted heteroaryl, substituted cycloalkyl, and substituted heterocyclyl; in which, when R2 and R3 are simultaneously present on one of R5, R6, R7 and R12, they can be linked to one another so as to form a ring comprising from 0 to 3 hetero atoms chosen from O, N and S;

g) Q is chosen from H, CH₃ and cyclopropyl; or a pharmaceutically acceptable salt thereof.

2. A compound as claimed in claim 1 corresponding to formula (I):

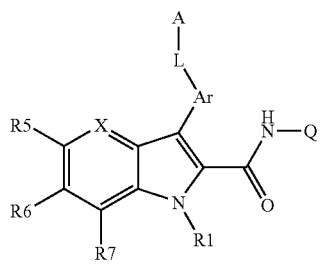

Formula (I)

in which
a) A and Ar are as defined in claim 1;
b) R1 is as defined in claim 1;
c) X is CR12;
d) L is as defined in claim 1;
e) R5, R6, R7 and R12 are each independently selected from the group consisting of: H, halogen, CF₃, NO₂, R2, CN, O(R2), OC(O)(R2), OC(O)N(R2)(R3), OS(O₂)(R2), N(R2)(R3), N=C(R2)(R3), N(R2)C(O)(R3), N(R2)C(O)O(R3), N(R4)C(O)N(R2)(R3), N(R4)C(S)N(R2)(R3), N(R2)S(O₂)(R3), OS(O₂)(R3), C(O)(R2), C(O)O(R2), C(O)N(R2)(R3), C(=N(R3))(R2), C(=N(OR3))(R2), S(R2), S(O)(R2), S(O₂)(R2), S(O₂)O(R2), and S(O₂)N(R2)(R3); in which each R2, R3, R4 is as defined in claim 1;
f) Q is as defined in claim 1; or a pharmaceutically acceptable salt thereof.

3. A compound as claimed in claim 1, wherein Q is H; or a pharmaceutically acceptable salt thereof.

4. A compound as claimed in claim 3, wherein:
a) A and Ar are as defined in claim 1;
b) R1 is H;
c) X is CH; and
d) L is NH—CO—NH; or a pharmaceutically acceptable salt thereof.

5. A compound as claimed in claim 1, wherein R11 is selected from the group consisting of H, F, Cl, methyl, NH₂, OCF₃ and CONH₂; or a pharmaceutically acceptable salt thereof.

6. A compound as claimed in claim 1, wherein R5, R6, R7 and R12 are each independently selected from the group consisting of H, halogen, methyl, OCH₃, OCF₃, OH, NH₂, NH(CH₂)₂OH, NH(CH₂)₂OCH₃, O(CH₂)COOH, O(CH₂)₂COOH, O(CH₂)₂NH(CH₂)₂OCH₃, O(CH₂)₂NH(CH₂)₂OH, pyridin-3-ylcarbonylamino-, 2-(N,N-diethylamino)ethoxy, 3-(N,N-diethylamino)propoxy, 2-(pyrrolidin-1-yl)ethoxy, 3-(pyrrolidin-1-yl)propoxy, 2-(piperidin-1-yl)ethoxy, 3-(piperidin-1-yl)propoxy, 2-(4-methylpiperazin-1-yl)ethoxy, 3-(4-methylpiperazin-1-yl)propoxy, 2-(morpholin-4-yl)ethoxy and 3-(morpholin-4-yl)propoxy; or a pharmaceutically acceptable salt thereof.

7. A compound as claimed in claim 1, wherein R5 and R7 are independently selected from H and F; or a pharmaceutically acceptable salt thereof.

8. A compound as claimed in claim 1, wherein R6 is H; or a pharmaceutically acceptable salt thereof.

9. A compound as claimed in claim 1, wherein A is phenyl optionally substituted; or a pharmaceutically acceptable salt thereof.

10. A compound as claimed in claim 1, wherein A is substituted with a first substituent selected from the group consisting of alkyl, halogenated alkyl, alkylene, alkynyl, aryl, O-alkyl, O-cycloalkyl, O-aryl, O-heteroaryl, S-alkyl, S-cycloalkyl, S-aryl and S-heteroaryl, each being optionally substituted with a substituent chosen from ($C_1$-$C_3$)alkyl, halogen and O—($C_1$-$C_3$)alkyl; or a pharmaceutically acceptable salt thereof.

11. A compound as claimed in claim 1, wherein A is substituted with a second substituent selected from the group consisting of F, Cl, Br, I, OH, $SO_3M$, COOM, CN, $NO_2$, CON(R8)(R9), N(R8) CO(R9), ($C_1$-$C_3$)alkyl-OH, ($C_1$-$C_3$) alkyl-N(R8)(R9), ($C_1$-$C_3$)alkyl-(R10), ($C_1$-$C_3$)alkyl-COOH, N(R8)(R9), and O—($C_2$-$C_4$)alkyl-N(R8)(R9); in which R8 and R9 are independently chosen from H, ($C_1$-$C_3$)alkyl, ($C_1$-$C_3$)alkyl-OH, ($C_1$-$C_3$)alkyl-$NH_2$, ($C_1$-$C_3$)alkyl-COOM and ($C_1$-$C_3$)alkyl-$SO_3M$; in which, when R8 and R9 are simultaneously different from H, they can be linked so as to form a ring comprising from 0 to 3 hetero atoms chosen from O, N and S; in which M is H or an alkali metal cation chosen from Li, Na and K; and in which R10 is H or an optionally substituted nonaromatic heterocycle comprising 2 to 7 carbon atoms and 1 to 3 hetero atoms chosen from N, O and S; or a pharmaceutically acceptable salt thereof.

12. A compound as claimed in claim 1, wherein A is phenyl substituted with halogen, ($C_1$-$C_4$)alkyl, halogenated ($C_1$-$C_3$) alkyl, O—($C_1$-$C_4$)alkyl, O-cycloalkyl, S—($C_1$-$C_4$)alkyl, S-cycloalkyl, halogenated O—($C_1$-$C_4$)alkyl or halogenated S—($C_1$-$C_4$)alkyl; or a pharmaceutically acceptable salt thereof.

13. A compound according to claim 12, wherein the halogen substituent is F; or a pharmaceutically acceptable salt thereof.

14. A compound according to claim 12, wherein the halogenated ($C_1$-$C_3$)alkyl substituent is $CF_3$; or a pharmaceutically acceptable salt thereof.

15. A compound according to claim 1, wherein A is phenyl substituted with 0, 1, 2, 3, 4 or 5 substituents selected from the group consisting of alkyl, halogenated alkyl, alkylene, alkynyl, aryl, O-alkyl, O-cycloalkyl, O-aryl, O-heteroaryl, S-alkyl, S-cycloalykl, S-aryl, and S-heteroaryl; each being optionally substituted with a substituent chosen from ($C_1$-$C_3$)alkyl, halogen, O—($C_1$-$C_3$)alkyl; and F, Cl, Br, I, OH, $SO_3M$, COOM, CN, $NO_2$, CON(R8)(R9), N(R8)CO(R9), ($C_1$-$C_3$) alkyl-OH, ($C_1$-$C_3$)alkyl-N(R8)(R9), ($C_1$-$C_3$)alkyl-(R10), ($C_1$-$C_3$)alkyl-COOH, N(R8)(R9), and O—($C_2$-$C_4$)alkyl-N (R8)(R9); in which R8 and R9 are independently chosen from H, ($C_1$-$C_3$)alkyl, ($C_1$-$C_3$)alkyl-OH, ($C_1$-$C_3$)alkyl-$NH_2$, ($C_1$-$C_3$)alkyl-COOM, and ($C_1$-$C_3$)alkyl-$SO_3M$; in which, when R8 and R9 are simultaneously different from H, they can be linked so as to form a ring comprising from 0 to 3 hetero atoms chosen from O, N and S; in which M is H or an alkali metal cation chosen from Li, Na and K; and in which R10 is H or an optionally substituted nonaromatic heterocycle comprising 2 to 7 carbon atoms and 1 to 3 hetero atoms chosen from N, O and S; or a pharmaceutically acceptable salt thereof.

16. A compound as claimed in claim 1, selected from the group consisting of:
- 3-{4-[3-(2-fluoro-5-trifluoromethylphenyl)ureido]phenyl}-1H-indole-2-carboxamide;
- 3-[4-(3-phenylureido)phenyl]-1H-indole-2-carboxamide;
- 3-[4-(3-m-tolylureido)phenyl]-1H-indole-2-carboxamide;
- 3-[4-(3-trifluoromethylphenylureido)phenyl]-1H-indole-2-carboxamide;
- 3-[4-(3,5-dimethylphenylureido)phenyl]-1H-indole-2-carboxamide;
- 3-[4-(2-fluorophenylureido)phenyl]-1H-indole-2-carboxamide;
- 3-{4-[3-(2-fluoro-5-trifluoromethylphenyl)ureido]-phenyl}-1-methyl-1H-indole-2-carboxamide;
- 3-{4-[3-(3-chloro-4-trifluoromethylphenyl)ureido]phenyl}-1H-indole-2-carboxamide;
- 3-{4-[3-(5-methoxy-2-trifluoromethylphenyl)ureido]phenyl}-1H-indole-2-carboxamide;
- 3-{4-[3-(2-fluoro-5-methylphenyl)ureido]phenyl}1H-indole-2-carboxamide;
- 3-{4-[3-(5-dimethylamino-2-fluorophenyl)ureido]-phenyl}-1H-indole-2-carboxamide;
- 3-{4-[3-(3-dimethylaminophenyl)ureido]phenyl}-1H-indole-2-carboxamide;
- 3-{4-[3-(2-pyrrolidin-1-ylmethyl-5-trifluoromethylphenyl)ureido]phenyl}-1H-indole-2-carboxamide;
- 3-{4-[3-(2-methoxymethyl-5-trifluoromethylphenyl)ureido]phenyl}-1H-indole-2-carboxamide;
- 3-{4-[3-(2-fluoro-5-trifluoromethylphenyl)ureido]-phenyl}-6-(2-methoxyethoxy)-1H-indole-2-carboxamide;
- 3-{4-[3-(2-fluoro-5-trifluoromethylphenyl)ureido]-phenyl}-6-(2-pyrrolidin-1-ylethoxy)-1H-indole-2-carboxamide;
- 3-{4-[3-(2-fluoro-5-trifluoromethylphenyl)ureido]-phenyl}-6-methoxy-1H-indole-2-carboxamide;
- 3-{4-[3-(2-fluoro-5-trifluoromethylphenyl)ureido]-phenyl}-6-hydroxy-1H-indole-2-carboxamide;
- 3-{4-[3-(2-fluoro-5-trifluoromethylphenyl)ureido]phenyl}-6-(2-hydroxyethoxy)-1H H-indole-2-carboxamide-carboxamide;
- 3-{4-[3-(2-fluoro-5-trifluoromethylphenyl)ureido]-phenyl}-7-nitro-1H-indole-2-carboxamide;
- 7-amino-3-{4-[3-(2-fluoro-5-trifluoromethylphenyl)ureido]phenyl}-1H-indole-2-carboxamide;
- 3-{4-[3-(2-fluoro-5-trifluoromethylphenyl)ureido]-phenyl}-7-(2-hydroxyethylamino)-1H-indole-2-carboxamide;
- 7-(2-dimethylaminoacetylamino)-3-{4-[3-(2-fluoro-5-trifluoromethylphenyl)ureido]phenyl}-1H-indole-2-carboxamide;
- 3-{4-[3-(4-tert-butylphenyl)ureido]phenyl}-1H-indole-2-carboxamide;
- 3-{4-[3-(4-trifluoromethylsulfanylphenyl)ureido]-phenyl}-1H-indole-2-carboxamide;
- 3-{4-[3-(4-difluoromethoxyphenyl)ureido]phenyl}-1H-indole-2-carboxamide;
- 3-{4-[3-(3-fluoro-4-methylphenyl)ureido]phenyl}-1H-indole-2-carboxamide;
- 3-{4-[3-(4-chlorophenyl)ureido]phenyl}-1H-indole-2-carboxamide;
- 3-{4-[3-(4-dimethylaminophenyl)ureido]phenyl}-1H-indole-2-carboxamide;
- 3-[4-(3-p-tolylureido)phenyl]-1H-indole-2-carboxamide;
- 3-{4-[3-(4-fluorophenyl)ureido]phenyl}-1H-indole-2-carboxamide;
- 3-{4-[3-(3-chloro-4-fluorophenyl)ureido]phenyl}-1H-indole-2-carboxamide;
- 3-{4-[3-(2-difluoromethoxyphenyl)ureido]phenyl}-1H-indole-2-carboxamide;
- 3-{4-[3-(3-methoxyphenyl)ureido]phenyl}-1H-indole-2-carboxamide;
- 3-{4-[3-(4-methoxyphenyl)ureido]phenyl}-1H-indole-2-carboxamide;
- 3-{4-[3-(3-bromophenyl)ureido]phenyl}-1H-indole-2-carboxamide;
- 3-{4-[3-(3-fluorophenyl)ureido]phenyl}-1H-indole-2-carboxamide;

3-{4-[3-(3-chlorophenyl)ureido]phenyl}-1H-indole-2-carboxamide;

3-{4-[3-(4-trifluoromethylphenyl)ureido]phenyl}-1H-indole-2-carboxamide;

3-{4-[3-(3-ethylphenyl)ureido]phenyl}-1H-indole-2-carboxamide;

3-{4-[3-(4-isopropylphenyl)ureido]phenyl}-1H-indole-2-carboxamide;

5-fluoro-3-{4-[3-(2-fluoro-5-trifluoromethylphenyl)ureido]phenyl}-1H-indole-2-carboxamide;

6-fluoro-3-{4-[3-(2-fluoro-5-trifluoromethylphenyl)ureido]phenyl}-1H-indole-2-carboxamide;

3-{4-[3-(2-fluoro-5-trifluoromethylphenyl)ureido]-3-fluorophenyl}-1H-indole-2-carboxamide;

3-{4-[3-(2-fluoro-5-trifluoromethylphenyl)ureido]-3-methylphenyl}-1H-indole-2-carboxamide;

4-methoxy-3-{4-[3-(2-fluoro-5-trifluoromethylphenyl)ureido]phenyl}-1H-indole-2-carboxamide;

5-methoxy-3-{4-[3-(2-fluoro-5-trifluoromethylphenyl)ureido]phenyl}-1H-indole-2-carboxamide; 5-nitro-3-{4-[3-(2-fluoro-5-trifluoromethylphenyl)ureido]phenyl}-1H-indole-2-carboxamide;

5-trifluoromethoxy-3-{4-[3-(2-fluoro-5-trifluoromethylphenyl)ureido]phenyl}-1H-indole-2-carboxamide;

7-(2-morpholin-1-ylethoxy)-3-{4-[3-(2-fluoro-5-trifluoromethylphenyl)ureido]phenyl}-1H-indole-2-carboxamide;

7-(2-pyrrolidin-1-ylethoxy-3-{4-[3-(2-fluoro-5-trifluoromethylphenyl)ureido]phenyl}-1H-indole-2-carboxamide;

7-(3-pyridin-3-ylcarbonylamino)-3-{4-[3-(2-fluoro-5-trifluoromethylphenyl)ureido]phenyl}-1H-indole-2-carboxamide;

7-(3-methoxyethylamino)-3-{4-[3-(2-fluoro-5-trifluoromethylphenyl)ureido]phenyl}-1H-indole-2-carboxamide;

7-hydroxy-3-{4-[3-(2-fluoro-5-trifluoromethylphenyl)ureido]phenyl}-1H-indole-2-carboxamide;

7-methoxy-3-{4-[3-(2-fluoro-5-trifluoromethylphenyl)ureido]phenyl}-1H-indole-2-carboxamide;

6-(2-morpholin-1-ylethoxy)-3-{4-[3-(2-fluoro-5-trifluoromethylphenyl)ureido]phenyl}-1H-indole-2-carboxamide;

3-{4-[3-(2-fluoro-4-hydroxy-5-trifluoromethylphenyl)ureido]phenyl}-1H-indole-2-carboxamide;

3-{4-[3-(4-chloro-5-trifluoromethylphenyl)ureido]-phenyl}-1H-indole-2-carboxamide;

7-(2-morpholin-1-ylethoxy)-3-{4-[3-(4-fluoro-5-trifluoromethylphenyl)ureido]phenyl}-1H-indole-2-carboxamide;

7-(2-morpholin-1-ylethoxy)-3-{4-[3-(4-methyl-3-trifluoromethylphenyl)ureido]phenyl}-1H-indole-2-carboxamide;

3-{4-[3-(4-(pyrrolidin-1-ylmethoxy)-3-trifluoromethylphenyl)ureido]phenyl}-1H-indole-2-carboxamide; and 3-{4-[3-(4-(4-methylpiperazin-1-ylmethyl)-3-trifluoromethylphenyl)ureido]phenyl}-1H-indole-2-carboxamide;

or a pharmaceutically acceptable salt thereof.

17. A compound as claimed in claim 1, which is:
3-{4-[3-(2-fluoro-5-trifluoromethylphenyl)ureido]-phenyl}-1H-indole-2-carboxamide; or a pharmaceutically acceptable salt thereof.

18. A compound according to claim 1, wherein it is in any one of the following forms:
1) nonchiral, or
2) racemic, or
3) enriched in a stereoisomer, or
4) enriched in an enantiomer;
and which is optionally salified.

19. A pharmaceutical composition comprising a compound according to claim 1 or a pharmaceutically acceptable salt thereof, in combination with a pharmaceutically acceptable excipient.

20. A pharmaceutical composition comprising a compound according to claim 16 or a pharmaceutically acceptable salt thereof, in combination with a pharmaceutically acceptable excipient.

* * * * *

UNITED STATES PATENT AND TRADEMARK OFFICE
CERTIFICATE OF CORRECTION

PATENT NO. : 7,566,736 B2 Page 1 of 1
APPLICATION NO. : 11/757613
DATED : July 28, 2009
INVENTOR(S) : Frank Halley et al.

It is certified that error appears in the above-identified patent and that said Letters Patent is hereby corrected as shown below:

In column 16, line 33, delete "1);" and insert -- 1H); --, therefor.

In column 19, line 11, delete "J 8.5" and insert -- J=8.5 --, therefor.

In column 23, line 27, delete "SH);" and insert -- 5H); --, therefor.

In column 31, line 47, delete "{{" and insert -- { --, therefor.

In column 41, line 10, delete "($C_5H_{10}ON^+$)" and insert -- ($C_5H_{10}N^+$) --, therefor.

In column 48, line 61, delete "J 6.0" and insert -- J=6.0 --, therefor.

In column 74, line 1, delete "($^4$-methyl" and insert -- (4-methyl --, therefor.

In column 74, line 38, delete "($^4$-trifluoromethoxyphenyl)" and insert -- (4-trifluoromethoxyphenyl) --, therefor.

In column 79, line 67, delete "PLCY" and insert -- PLCγ --, therefor.

In column 96, line 63, in Claim 9, delete "phenyl" and insert -- phenyl, --, therefor.

In column 98, line 7-8, in Claim 16, delete "3-{4-[3-(5-methoxy-2-trifluoromethylphenyl)ureido]phenyl}-1H-indole-2-carboxamide;" and insert
-- 3-{4-[3-(4-trifluoromethoxyphenyl)ureido]phenyl} 1H-indole-2-carboxamide;
3-{4-[3-(2-methoxy-5-trifluoromethylphenyl)ureido]phenyl}-1H-indole-2-carboxamide --, therefor.

In column 98, line 29, in Claim 16, delete "1H H" and insert -- 1H --, therefor.

In column 98, line 29-30, in Claim 16, delete "carboxamide-carboxamide;" and insert -- carboxamide; --, therefor.

Signed and Sealed this

Seventeenth Day of August, 2010

David J. Kappos
*Director of the United States Patent and Trademark Office*